US008981092B2

(12) United States Patent
Mirizzi et al.

(10) Patent No.: US 8,981,092 B2
(45) Date of Patent: Mar. 17, 2015

(54) SUBSTITUTED 3,4-DIHYDRO-2H-PYRROLO[1,2-A]PYRAZIN-1-ONES AS MODULATORS OF PROTEIN KINASE ACTIVITY

(71) Applicants: Danilo Mirizzi, Milan (IT); Giovanni Cervi, Como (IT); Matteo D'Anello, Novate Milanese (IT); Gianluca Mariano Enrico Papeo, Cernusco Lombardone (IT); Ron Ferguson, Scotch Plains, NJ (US); Francesco Casuscelli, Dairago (IT)

(72) Inventors: Danilo Mirizzi, Milan (IT); Giovanni Cervi, Como (IT); Matteo D'Anello, Novate Milanese (IT); Gianluca Mariano Enrico Papeo, Cernusco Lombardone (IT); Ron Ferguson, Scotch Plains, NJ (US); Francesco Casuscelli, Dairago (IT)

(73) Assignee: Nerviano Medical Sciences S.r.l., Nerviano (MI) (IT)

( * ) Notice: Subject to any disclaimer, the term of this patent is extended or adjusted under 35 U.S.C. 154(b) by 0 days.

(21) Appl. No.: 13/747,859

(22) Filed: Jan. 23, 2013

(65) Prior Publication Data
US 2013/0137696 A1 May 30, 2013

Related U.S. Application Data

(62) Division of application No. 13/119,849, filed as application No. PCT/EP2009/062061 on Sep. 17, 2009, now Pat. No. 8,394,802.

(30) Foreign Application Priority Data

Sep. 19, 2008 (EP) ..................... 08164714

(51) Int. Cl.
C07D 241/38 (2006.01)
A61K 31/4985 (2006.01)
C07D 487/04 (2006.01)
A61K 45/06 (2006.01)

(52) U.S. Cl.
CPC .......... *A61K 31/4985* (2013.01); *C07D 487/04* (2013.01); *A61K 45/06* (2013.01)
USPC ....................................... 544/349

(58) Field of Classification Search
CPC .................................... C07D 241/38
USPC ....................................... 544/349
See application file for complete search history.

(56) References Cited

U.S. PATENT DOCUMENTS

2011/0251179 A1  10/2011  Mirizzi et al.

FOREIGN PATENT DOCUMENTS

| WO | WO 2004/047725 A2 | 6/2004 |
| WO | WO 2007/042784 A2 | 4/2007 |
| WO | WO 2010/031816 | * 3/2010 |

OTHER PUBLICATIONS

Jordan, V. C. Nature Reviews: Drug Discovery, 2, 2003, 205.*
Hackam, et al. JAMA, 296(14), 2006, 1731-1732.*
U.S. Final Office Action dated Jul. 13, 2012 from parent U.S. Appl. No. 13/119,849.
U.S. Office Action dated Apr. 2, 2012 from parent U.S. Appl. No. 13/119,849.
International Search Report dated Nov. 2, 2009 received from the European Patent Office from related International Application No. PCT/EP2009/062061.

* cited by examiner

*Primary Examiner* — Douglas M Willis
(74) *Attorney, Agent, or Firm* — Scully, Scott, Murphy & Presser, P.C.

(57) ABSTRACT

Compounds which are 4,7-disubstituted derivatives of 3,4-dihydro-2H-pyrrolo[1,2-a]pyrazin-1-one compounds,

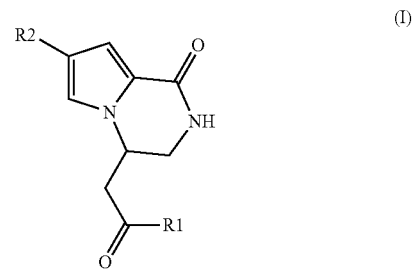

or pharmaceutically acceptable salts thereof, their preparation process and pharmaceutical compositions comprising them are disclosed; these compounds are useful in the treatment of diseases caused by and/or associated with an altered protein kinase activity such as cancer, viral infection, prevention of AIDS development in HIV-infected individuals, cell proliferative disorders, autoimmune and neurodegenerative disorders; also disclosed is a process under Solid Phase Synthesis conditions for preparing the compounds of the invention and chemical libraries comprising a plurality of them.

5 Claims, No Drawings

SUBSTITUTED 3,4-DIHYDRO-2H-PYRROLO[1,2-A]PYRAZIN-1-ONES AS MODULATORS OF PROTEIN KINASE ACTIVITY

CROSS REFERENCE TO RELATED APPLICATIONS

The present application is a divisional of co-pending application having U.S. Ser. No. 13/119,849, filed on Apr. 8, 2011, which is a 371 of International Application having Serial No. PCT/EP2009/062061, filed on Sep. 17, 2009, which claims priority of European Patent Application No. 08164714.1, filed on Sep. 19, 2008, the contents of all of which are incorporated herein by reference.

BACKGROUND

The present invention relates to certain 4,7-disubstituted derivatives of 3,4-dihydro-2H-pyrrolo[1,2-a]pyrazin-1-one compounds, which modulate the activity of protein kinases. The compounds of this invention are therefore useful in treating diseases caused by dysregulated protein kinase activity. The present invention also relates to methods for preparing these compounds, combinatorial libraries thereof, pharmaceutical compositions comprising these compounds, and methods of treating diseases utilizing pharmaceutical compositions comprising these compounds.

The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For general reference to PKs malfunctioning or disregulation see, for instance, Current Opinion in Chemical Biology 1999, 3, 459-465 and Carcinogenesis 2008, 29, 1087-191.

8-Hydroxy-3,4-dihydro-2H-pyrrolo[1,2-a]pyrazin-1-one derivatives for prevention and treatment of infection by HIV and in the prevention, delay in the onset and treatment of AIDS are disclosed in WO 2004/047725 in the name of Merck & Co., Inc., USA. The present inventors have now discovered that the new compounds of formula (I), described below, are kinase inhibitors and are thus useful in therapy as antitumor agents.

BRIEF SUMMARY OF THE DISCLOSURE

Accordingly, a first object of the present invention is to provide a 4,7-disubstituted-3,4-dihydro-2H-pyrrolo[1,2-a]pyrazin-1-one compound represented by formula (I):

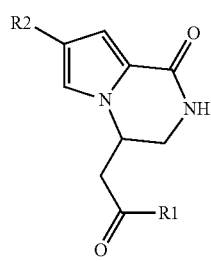

(I)

wherein:
R1 is a group —NR$^a$R$^b$ or —OR$^a$ and

R2 is —NH$_2$, —NHCOR$^c$, —NHCONHR$^c$, —NHSO$_2$R$^c$, —C≡CR$^d$ or R$^d$ wherein R$^a$, R$^b$, R$^c$ and R$^d$, the same or different, are each independently hydrogen or a group optionally further substituted, selected from straight or branched C$_1$-C$_6$ alkyl, C$_2$-C$_6$ alkenyl or C$_2$-C$_6$ alkynyl, C$_3$-C$_6$ cycloalkyl, cycloalkyl C$_1$-C$_6$ alkyl, heterocyclyl, heterocyclyl C$_1$-C$_6$ alkyl, aryl, aryl C$_1$-C$_6$ alkyl, heteroaryl and heteroaryl C$_1$-C$_6$ alkyl, or R$^a$ and R$^b$, taken together with the nitrogen atom to which they are bonded, may form an optionally substituted 3 to 7 membered heterocyclyl or heteroaryl, optionally containing one additional heteroatom or heteroatomic group selected from S, O, N or NH, and pharmaceutically acceptable salts thereof.

The present invention also provides methods of synthesizing the 4,7-disubstituted-3,4-dihydro-2H-pyrrolo[1,2-a]pyrazin-1-one compounds, represented by formula (I), prepared through a process consisting of standard synthetic transformations.

The present invention also provides a method for treating diseases caused by and/or associated with dysregulated protein kinase activity, particularly PLK family, ABL, AKT1, ALK, AUR1, AUR2, BRK, CDC7/DBF4, CDK2/CYCA, CHK1, CK2, EE2FK, EGFR1, ERK2, FAK, FGFR1, FLT3, GSK3beta, IGFR1, IKK2, IR, JAK2, JAK3, KIT, LCK, MAPKAPK2, MET, MPS1, MST4, NEK6, NIM1, P38alpha, PAK-4, PDGFR, PDK1, PERK, PIM1, PIM2, PIM3, PKAalpha, PKCbeta, PLK1, RET, SULU1, SYK, TRKA, VEGFR2, VEGFR3 or ZAP70.

A preferred method of the present invention is to treat a disease caused by and/or associated with dysregulated protein kinase activity selected from the group consisting of cancer, viral infection, prevention of AIDS development in HIV-infected individuals, cell proliferative disorders, autoimmune and neurodegenerative disorders.

Another preferred method of the present invention is to treat specific types of cancer including but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocytic leukaemia, acute lymphoblastic leukaemia, B-cell lymphoma, T-cell-lymphoma, Hodgkin's lymphoma, non-Hodgkin's lymphoma, hairy cell lymphoma and Burkitt's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Another preferred method of the present invention is to treat specific cellular proliferation disorders such as, for example, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

The compounds of this invention may be useful in inhibiting tumour angiogenesis and metastasis, as well as in the treatment of organ transplant rejection and host versus graft disease.

The present invention further provides a method of treatment comprising a compound of formula (I) in combination with radiation therapy or chemotherapy regimen for simultaneous, separate or sequential use in anticancer therapy.

Moreover the invention provides a method for inhibiting protein kinase activity which comprises contacting the said protein kinase with an effective amount of a compound of formula (I).

The present invention also provides a pharmaceutical composition comprising one or more compounds of formula (I) or a pharmaceutically acceptable salt thereof and a pharmaceutically acceptable excipient, carrier or diluent.

The present invention also provides a pharmaceutical composition comprising a compound of formula (I) in combination with known cytostatic or cytotoxic agents, antibiotic-type agents, DNA damaging or intercalating agents, platin-based agents, alkylating agents, antimetabolite agents, hormonal agents, antihormonal agents such as antiestrogens, antiandrogens and aromatase inhibitors, immunological agents, interferon-type agents, cyclooxygenase inhibitors (e.g. COX-2 inhibitors), matrixmetalloprotease inhibitors, tyrosine kinase inhibitors, other kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, inhibitors of kinesins, therapeutic monoclonal antibodies, inhibitors of mTOR, histone deacetylase inhibitors, inhibitors of hypoxic response and the like, for simultaneous, separate or sequential use in anticancer therapy. Additionally, the invention provides a product or kit comprising a compound of formula (I) or a pharmaceutically acceptable salt thereof, as defined above, or pharmaceutical compositions thereof and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament.

Moreover the invention provides the use of a compound of formula (I) or a pharmaceutically acceptable salt thereof, as defined above, in the manufacture of a medicament with antitumor activity.

Finally, the invention provides a compound of formula (I) or a pharmaceutically acceptable salt thereof, as defined above, for use in a method of treating cancer.

DETAILED DESCRIPTION OF THE DISCLOSURE

Unless otherwise specified, when referring to the compounds of formula (I) per se as well as to any pharmaceutical composition thereof or to any therapeutic method of treatment comprising them, the present invention includes all the hydrates, solvates, complexes, metabolites, prodrugs, carriers, N-oxides and pharmaceutically acceptable salts of the compounds of this invention.

A metabolite of a compound of formula (I) is any compound into which this same compound of formula (I) is converted in vivo, for instance upon administration to a mammal in need thereof. Typically, without however representing a limiting example, upon administration of a compound of formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of formula (I).

Prodrugs are any covalently bonded compounds, which release the active parent drug according to formula (I) in vivo.

N-oxides are compounds of formula (I) wherein nitrogen and oxygen are tethered through a dative bond.

All forms of chiral isomers or other forms of isomers including enantiomers and diastereomers, are intended to be covered herein. Compounds containing a chiral center may be used as a racemic mixture or as an enantiomerically enriched mixture, or the racemic mixture may be separated using well-known techniques and an individual enantiomer may be used alone.

In cases wherein compounds may exist in tautomeric forms, such as keto-enol tautomers, each tautomeric form is contemplated as being included within this invention whether existing in equilibrium or predominantly in one form.

In the present description, unless otherwise indicated, with the term "straight or branched $C_1$-$C_6$ alkyl" we intend any group such as, for instance, methyl, ethyl, n-propyl, isopropyl, n-butyl, isobutyl, sec-butyl, tert-butyl, n-pentyl, n-hexyl, and the like.

With the term "straight or branched $C_2$-$C_6$ alkenyl" or "straight or branched $C_2$-$C_6$ alkynyl" we intend any of the unsaturated alkenyl or alkynyl groups with from 2 to 6 carbon atoms for instance including vinyl, allyl, 1-propenyl, isopropenyl, 1-, 2- or 3-butenyl, pentenyl, hexenyl, ethynyl, 1- or 2-propynyl, butynyl, pentynyl, hexynyl, and the like.

With the term "$C_3$-$C_6$ cycloalkyl" we intend, unless otherwise specified, 3- to 6-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene and cyclohexadiene.

With the term "heterocyclyl" we intend a 3- to 7-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

With the term "aryl" we intend a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated π-electron bond system. Non-limiting examples of such aryl groups are phenyl, α- or β-naphthyl or biphenyl groups.

With the term "heteroaryl" we intend aromatic heterocyclic rings, typically 5- to 7-membered heterocycles with from 1 to 3 heteroatoms selected among N, O or S; the heteroaryl ring can be optionally further fused or linked to aromatic and non-aromatic carbocyclic and heterocyclic rings. Not limiting examples of such heteroaryl groups are, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl; benzopyranyl, 2,3-dihydrobenzoxazinyl, 2,3-dihydroquinoxalinyl and the like.

According to the meanings provided to $R^a$, $R^b$, $R^c$ and $R^d$, any of the above groups may be further optionally substituted in any of their free positions by one or more groups, for instance 1 to 6 groups, selected from: halogen, nitro, oxo groups (=O), carboxy, cyano, $C_1$-$C_6$ alkyl, polyfluorinated alkyl, $C_2$-$C_6$ alkenyl, $C_2$-$C_6$ alkynyl, $C_3$-$C_6$ cycloalkyl, heterocyclyl, aryl, heteroaryl; amino groups and derivatives thereof such as, for instance, alkylamino, dialkylamino, arylamino, diarylamino, ureido, alkylureido or arylureido; carbonylamino groups and derivatives thereof such as, for instance, formylamino, alkylcarbonylamino, alkenylcarbonylamino, arylcarbonylamino, alkoxycarbonylamino; hydroxy groups and derivatives thereof such as, for instance, alkoxy, polyfluorinated alkoxy, aryloxy, alkylcarbonyloxy, arylcarbonyloxy, cycloalkenyloxy or alkylideneaminoxy; carbonyl groups and derivatives thereof such as, for instance, alkylcarbonyl, arylcarbonyl, alkoxycarbonyl, aryloxycarbonyl, cycloalkyloxycarbonyl, aminocarbonyl, alkylaminocarbonyl, dialkylaminocarbonyl; sulfurated derivatives such as, for instance, alkylthio, arylthio, alkylsulfonyl, arylsulfonyl, alkylsulfinyl, arylsulfinyl, arylsulfonyloxy, aminosulfonyl, alkylaminosulfonyl or dialkylaminosulfonyl.

In their turn, whenever appropriate, each of the above substituents may be further substituted by one or more of the aforementioned groups.

In the present description, unless otherwise specified, with the term "cyano" we intend a —CN residue.

With the term "nitro" we intend a —NO$_2$ group.

With the term "halogen" we intend a fluorine, chlorine, bromine or iodine atom.

With the term "polyfluorinated alkyl or alkoxy" we intend a straight or branched C$_1$-C$_6$ alkyl or alkoxy group as above defined, wherein more than one hydrogen atom is replaced by fluorine atoms such as, for instance, trifluoromethyl, trifluoromethoxy, 2,2,2-trifluoroethyl, 2,2,2-trifluoroethoxy, 1,2-difluoroethyl, 1,1,1,3,3,3-hexafluoropropyl-2-yl, and the like.

From all of the above, it is clear to the skilled man that any group which name has been identified as a composite name such as, for instance, cycloalkylalkyl, arylalkyl, heterocyclylalkyl, alkoxy, alkylthio, aryloxy, arylalkyloxy, alkylcarbonyloxy and the like, has to be intended as conventionally construed from the parts to which it derives. So far, as an example, the terms heterocyclyl-alkyl and cycloalkyl-alkyl stand for a straight or branched alkyl group being further substituted by a heterocyclic or cycloalkyl group, respectively, as above defined.

The term "pharmaceutically acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of the compounds of the present invention may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic and sulfonic classes of organic acids, examples of which are formic, acetic, trifluoroacetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, hydroxybutyric, galactaric and galacturonic acid. Suitable pharmaceutically acceptable base addition salts of the compounds of the present invention include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methyl-glucamine) and procaine. All of these salts may be prepared by conventional means from the corresponding compounds of the present invention, for instance by reacting them with the appropriate acid or base.

A preferred class of compounds of formula (I) are the compounds wherein: R1 is a group —NR$^a$R$^b$ and R$^a$ and R$^b$ are both hydrogen atoms or one of them is a hydrogen atom and the remaining one of R$^a$ or R$^b$ is a straight or branched C$_1$-C$_6$ alkyl or C$_2$-C$_6$ alkenyl group or it is an optionally substituted aryl or aryl C$_1$-C$_6$ alkyl group.

Another preferred class of compounds of formula (I) are the compounds wherein:
R2 is a group —NHCOR wherein R$^c$ is as defined before.
A further preferred class of compounds of formula (I) are the compounds wherein:
R2 is a group —NHCONHR wherein R$^c$ is as defined before.
A more preferred class of compounds of formula (I) are the compounds wherein:
R2 is a group —NHSO$_2$R$^c$ wherein R$^c$ is as defined before.

For a reference to any specific compound of formula (I) of the invention, optionally in the form of pharmaceutically acceptable salts, see the experimental section.

The present invention also provides a process for the preparation of a compound of formula (I) as defined above, characterized in that the process comprises:

a) nitrating under acidic conditions the compound of formula (II):

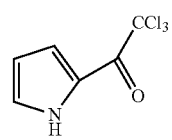

(II)

b) reacting the resultant compound of formula (III):

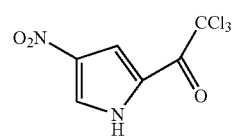

(III)

with an ammonium salt of formula (IV):

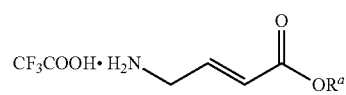

(IV)

wherein R$^a$ is C$_1$-C$_6$ alkyl;
optionally converting the resultant compound of formula (V):

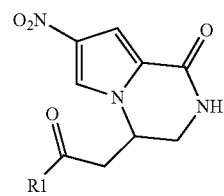

(V)

wherein R1 represents OR$^a$ and R$^a$ is as defined above, into another compound of formula (V) wherein R1 is as above defined by replacing —OR$^a$ group with a different R1 group, c) reducing said compound of formula (V) to give a compound of formula (I) or a salt thereof:

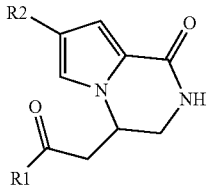

wherein R1 is as defined above, and R2 is $NH_2$;

optionally separating the resultant compound of formula (I) into the single isomers;

converting the resultant compound of formula (I) into a different compound of formula (I) by derivatizing the amino moiety, and/or by replacing the group —$OR^a$ with a different group which R1 represents, and/or converting it into a pharmaceutically acceptable salt if desired.

The present invention further provides a process for the preparation of a compound of formula (I) as defined above, characterized in that the compound of formula (I) is converted into another compound of formula (I), said conversion being carried out by one or more of the following reactions:

d) reacting a compound of formula (I) wherein R1 is —$OR^a$ and $R^a$ is $C_1$-$C_6$ alkyl, and R2 is $NH_2$ according to any one of the alternative steps:

d.1) with an acid or an acyl halide of formula (VI):

wherein $R^c$ is as defined above and Z is a halogen or a group —OH, to give a compound of formula (I):

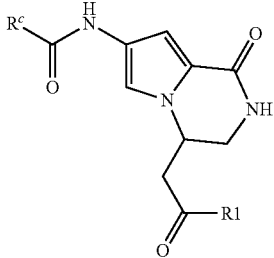

wherein R1 is —$OR^a$ and $R^a$ is $C_1$-$C_6$ alkyl and $R^c$ is as defined above; or d.2) with an isocyanate of formula (VII):

wherein $R^c$ is as defined above, to give a compound of formula (I):

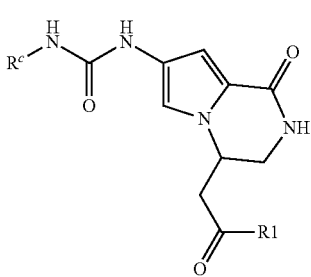

wherein R1 is —$OR^a$ and $R^a$ is $C_1$-$C_6$ alkyl and $R^c$ is as defined above; or d.3) with a sulphonyl halide of formula (VIII):

wherein $R^c$ is as defined above and Z' is a halogen, to give a compound of formula (I):

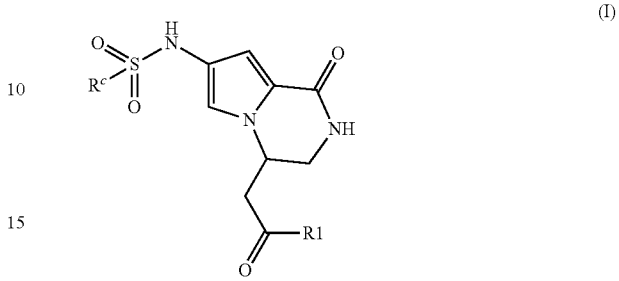

wherein R1 is —$OR^a$ and $R^a$ is $C_1$-$C_6$ alkyl and $R^c$ is as defined above, optionally separating the resultant compound of formula (I) into the single isomers; converting the resultant compound of formula (I) into a different compound of formula (I) by replacing the group —$OR^a$ with a different group which R1 represents, and/or into a pharmaceutically acceptable salt if desired.

The present invention also provides another process for the preparation of a compound of formula (XI), characterized in that the process comprises:

e) iodination of the compound of formula (II):

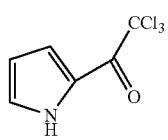

f) reacting the resultant compound of formula (IX):

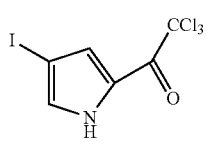

with an ammonium salt of formula (IV):

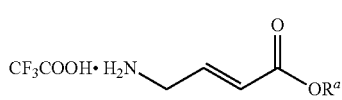

wherein $R^a$ is $C_1$-$C_6$ alkyl;

g) cyclizing under basic conditions the resultant compound of formula (X):

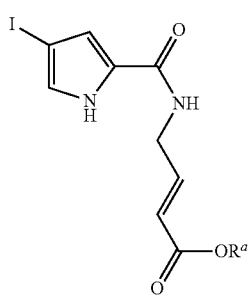

wherein $R^a$ is as defined above, to give the compound of formula (XI):

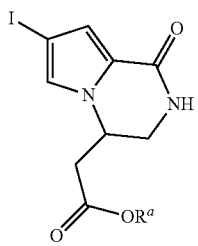

(XI)

wherein $R^a$ is as defined above;

converting it into a different compound of formula (XI) by replacing the Iodo with a different group that R2 represents, optionally separating it into the single isomers, converting it into a different compound of formula (XI) by replacing the —$OR^a$ group with a different group which R1 represents and/or into a pharmaceutically acceptable salt if desired.

The present inventions further provides a process for the preparation of compounds of formula (I) as defined above, characterized in that the process comprises:

h) reacting a compound of formula (XI) wherein R1 is —$OR^a$ and $R^a$ is $C_1$-$C_6$ alkyl, according to any one of the alternative steps:

h.1) with a boronic acid or ester of formula (XII):

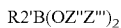

$R2'B(OZ''Z''')_2$ (XII)

wherein R2' is $R^d$ and $R^d$ is as defined above, Z" and Z'" are either H, alkyl or, taken together with the oxygen atoms to which they are bonded, may form an optionally substituted 5 to 6 membered heterocycle, to give a compound of formula (I):

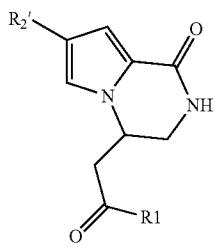

(I)

wherein R1 is —$OR^a$ and $R^a$ is $C_1$-$C_6$ alkyl and R2' is as defined above; or h.2) with a terminal alkyne of formula (XIII):

$R^dC\equiv CH$ (XIII)

wherein $R^d$ is as defined above, to give a compound of formula (I):

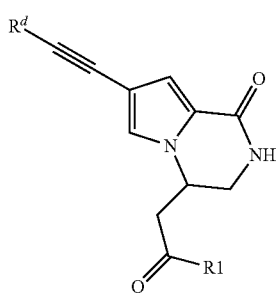

(I)

wherein R1 is —$OR^a$ and $R^a$ is $C_1$-$C_6$ alkyl and $R^d$ is as defined above, optionally separating the resultant compound of formula (I) into the single isomers; converting the resultant compound of formula (I) into a different compound of formula (I) by replacing the group —$OR^a$ with a different group which R1 represents, and/or into a pharmaceutically acceptable salt if desired.

The present invention further provides a process for the preparation of a compound of formula (I) as defined above, characterized in that the compound of formula (I) is converted into another compound of formula (I), said conversion is carried out by one or more of the following reactions:

m.1) acid or basic hydrolysis of a compound of formula (I), wherein R1 is —$OR^a$ and $R^a$ is $C_1$-$C_6$ alkyl, to give the corresponding compound of formula (I) wherein R1 is —$OR^a$ and $R^a$ is hydrogen, or the corresponding salt;

m.2) transesterification of a compound of formula (I) wherein R1 is —$OR^a$ and $R^a$ is $C_1$-$C_6$ alkyl, by reactions with a compound of formula (XIV):

$R^a$—OH (XIV)

to give the corresponding compound of formula (I) wherein R1 is —$OR^a$ and $R^a$ is a different $C_1$-$C_6$ alkyl;

m.3) aminolysis of a compound of formula (I) wherein $R_1$ is —$OR^a$ and $R^a$ is $C_1$-$C_6$ alkyl, by reaction with a compound of formula (XV):

$HNR^aR^b$ (XV)

to give the corresponding compound of formula (I) wherein R1 is —$NR^aR^b$;

m.4) esterification of a compound of formula (I) wherein R1 is a group —OH or its corresponding salt, by reactions with a compound of formula (XIV) as defined above, to give the corresponding compound of formula (I) wherein R1 is —$OR^a$;

m.5) amidation of a compound of formula (I) wherein R1 is a group —OH or its corresponding salt, by reaction with a compound of formula (XV) as defined above, to give the corresponding compound of formula (I) wherein R1 is —$NR^aR^b$.

The present invention further provides a process for the preparation of a compound of formula (I) as defined above, characterized in that the compound of formula (V) as defined above, is converted into another compound of formula (V), said conversions are carried out by one or more of the following reactions:

n.1) acid or basic hydrolysis of a compound of formula (V) wherein R1 is —$OR^a$ and $R^a$ is $C_1$-$C_6$ alkyl, to give a compound of formula (V) wherein R1 is —$OR^a$ and $R^a$ is hydrogen, or the corresponding salt;

n.2) transesterification of a compound of formula (V) wherein R1 is —$OR^a$ and $R^a$ is $C_1$-$C_6$ alkyl, by reaction with a compound of formula (XIV) as defined above, to give a compound of formula (V) wherein R1 is —$OR^a$ and $R^a$ is a different $C_1$-$C_6$ alkyl;

n.3) amidation of a compound of formula (V) wherein R1 is —$OR^a$ and $R^a$ is $C_1$-$C_6$ alkyl, by reaction with a compound of formula (XV) as defined above, to give a compound of formula (V) wherein R1 is —$NR^aR^b$;

n.4) esterification of a compound of formula (V) wherein R1 is —$OR^a$ and $R^a$ is hydrogen, or the corresponding salt, by reaction with a compound of formula (XVI) as defined above, to give a compound of formula (V) wherein R1 is —$OR^a$ and $R^a$ is different from hydrogen;

n.5) amidation of a compound of formula (V) wherein R1 is —$OR^a$ and $R^a$ is hydrogen, by reaction with a compound of formula (XV) as defined above, to give a compound of formula (V) wherein R1 is —$NR^aR^b$ The present invention further provides a process for the preparation of a compound of formula (I) as defined above, characterized in that the compound of formula (XI) as defined above, is converted into another compound of formula (XI), said conversions are carried out by one or more of the following reactions:

o.1) acid or basic hydrolysis of a compound of formula (XI) wherein R1 is —OR$^a$ and R$^a$ is $C_1$-$C_6$ alkyl, to give a compound of formula (XI) wherein R1 is —OR$^a$ and R$^a$ is hydrogen, or the corresponding salt;

o.2) transesterification of a compound of formula (XI) wherein R1 is —OR$^a$ and R$^a$ is $C_1$-$C_6$ alkyl, by reaction with a compound of formula (XIV) as defined above, to give a compound of formula (XI) wherein R1 is —OR$^a$ and R$^a$ is a different $C_1$-$C_6$ alkyl;

o.3) amidation of a compound of formula (XI) wherein R1 is —OR$^a$ and R$^a$ is $C_1$-$C_6$ alkyl, by reaction with a compound of formula (XV) as defined above, to give a compound of formula (XI) wherein R1 is —NR$^a$R$^b$;

o.4) esterification of a compound of formula (XI) wherein R1 is —OR$^a$ and R$^a$ is hydrogen, or the corresponding salt, by reaction with a compound of formula (XVI) as defined above, to give a compound of formula (XI) wherein R1 is —OR$^a$ and R$^a$ is different from hydrogen;

o.5) amidation of a compound of formula (XI) wherein R1 is —OR$^a$ and R$^a$ is hydrogen, by reaction with a compound of formula (XV) as defined above, to give a compound of formula (XI) wherein R1 is —NR$^a$R$^b$.

From all of the above, it is clear to the skilled person that if a compound of formula (I), (V), or (XI) prepared according to the above processes comprehensive of any variant thereof, is obtained as an admixture of isomers, their separation into the single isomers of formula (I), carried out according to conventional techniques, is still within the scope of the present invention.

Likewise, the conversion of a compound of formula (I) into a pharmaceutically acceptable salt thereof or, alternatively, the conversion into the free compound (I) of a corresponding salt, according to procedures well-known in the art, is still within the scope of the invention.

When preparing the compounds of formula (I) according to any variant of the process, which are all to be intended as within the scope of the invention, optional functional groups within the starting materials, the reagents or the intermediates thereof, and which could give rise to unwanted side reactions, need to be properly protected according to conventional techniques.

The starting materials of the process object of the present invention, comprehensive of any possible variant, as well as any reactant thereof, are known compounds and if not commercially available per se may be prepared according to well-known methods. For example, the compound of formula (II) is commercially available.

The compounds of formula (IV) are prepared starting from the corresponding 4-bromocrotonates that in their turn are commercially available or can be prepared according to well-known methods.

For example the 4-amino ethylcrotonate is prepared from the ethyl-4-bromo ethylcrotonate (XVI):

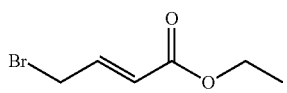

(XVI)

i) reacting it with commercially available diformylimide sodium salt (XVII):

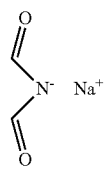

(XVII)

l) hydrolyzing in acidic conditions the resultant compound of formula (XVIII):

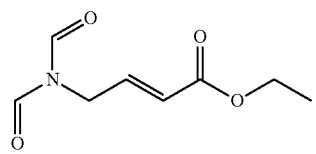

(XVIII)

to give the compound of formula (IV) wherein R$^a$ is ethyl.

The compounds of formula (VI), (VII), (VIII), (XII), (XIII), (XIV) and (XV) are known or easily obtained according to known methods, for a general reference see: Smith, Michael—March's Advanced Organic Chemistry: reactions mechanisms and structure—5$^{th}$ Edition, Michael B. Smith and Jerry March, John Wiley & Sons Inc., New York (NY), 2001.

The intermediate compound of formula (V):

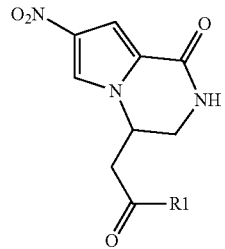

(V)

wherein R1 is as defined above, is novel and hence represents a further object of the invention.

The intermediate compound of formula (XI):

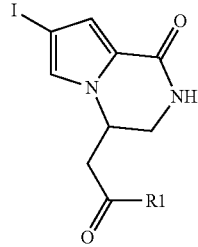

(XI)

wherein R1 is as defined above, is novel and hence represents a further object of the invention.

According to step (a) of the process, the nitration of the compound of formula (II) under acidic conditions can be carried out in a variety of ways according to conventional methods. Preferably, the reaction is carried out in the presence of nitric acid and acetic anhydride, at a temperature ranging from −40° C. to room temperature and for a time from 6 hours to overnight.

According to step (b) of the process, the conversion of the compound of formula (III) into the corresponding amido derivative of formula (V), can be carried out in a variety of ways according to conventional methods for obtaining amido derivatives from the corresponding α,α,α-trichloroketones. Preferably the reaction is carried out by reaction of an ammonium salt of formula (IV) in the presence of N,N-diisopropylethylamine, using dichloromethane as the solvent.

According to step (c) of the process, the reduction of the nitro group of the compound of formula (V) to give a compound of formula (I) can be carried out in a variety of ways, according to conventional methods for reducing nitro group to the corresponding amino derivative. Preferably the reaction is carried out in the presence of palladium on carbon in ethanol and hydrochloric acid, under an atmosphere of hydrogen at room temperature for a time ranging from 6 to 8 hours.

According to any one of steps (d.1) to (d.3) the preparation of functionalized amino derivatives starting from the corresponding amine can be carried out in a variety of ways, according to conventional methods.

Preferably according to step (d.1) and (d.3) of the process, the compound of formula (I) is dissolved in a suitable solvent such as dichloromethane, N,N-dimethylformamide, N,N-dimethylacetamide, tetrahydrofuran, dioxane or the like, and a suitable base such as triethylamine, N,N-diisopropylethylamine or sodium carbonate is added therein. The compounds of general formula (VI) or (VIII) are then added and the mixture stirred for a time of about 2 hours to about 15 hours, at a temperature ranging from about 20° C. to about 80° C. A suitable catalyst such as dimethylamino pyridine may be optionally used. Preferably according to step (d.2) of the process, the reaction conditions are the same as above reported for steps (d.1) and (d.3) except that the base may not be required. The compound of general formula (VII) is then added and the mixture stirred as reported above for steps (d.1) and (d.3).

According to step (e) of the process, the iodination of the compound of formula (II) can be carried out in a variety of ways according to conventional methods. Preferably, the reaction is carried out under neutral conditions in the presence of iodine and silver trifluoroacetate, at a temperature ranging from 0° C. to 180 C and for a time from 5 hours to overnight.

According to step (f) of the process, the conversion of the compound of formula (IX) into the corresponding amido derivative of formula (X), can be carried out in a variety of ways, according to conventional methods for obtaining amido derivatives from the corresponding α,α,α-trichloroketones. Preferably, the reaction is carried out as described under step (b).

According to step (g) of the process, the cyclization of the compound of formula (X) into the corresponding derivative of formula (XIa) can be carried out in a variety of ways according to conventional methods. Preferably, the reaction is carried out using a base such as diaza(1,3)bicyclo[5.4.0]undecane and acetonitrile as the solvent.

According to any one of steps (h.1) and (h.2) the conversion of a compound of formula (XIa) into a compound of formula (I) can be carried out in a variety of ways, according to conventional methods.

Preferably the reaction of step (h.1) is carried out through the Suzuki coupling between an organoboronic derivative of formula (XII) and a compound of formula (XIa), to give the corresponding compound of formula (I) in the presence of a Pd-catalyst and a base such as sodium or cesium carbonate, in a mixture of solvents, such as dimethoxyethane and water, at a temperature varying from room temperature to 80° C. and for a time between 4 hours and overnight.

Preferably the reaction of step (h.2) is carried out through the Sonogashira coupling between an alkyne derivative of formula (XIII) and a compound of formula (XIa), to give the corresponding compound of formula (I) in the presence of a Pd-catalyst, a base such as triethylamine and an additive such as copper(I) iodide, using N,N-dimethylformamide as the solvent, at room temperature and for a time between 4 hours and overnight.

According to step (i) of the process, the substitution reaction of ethyl-4-bromocrotonate of formula (XVI) with diformylimide sodium salt of formula (XVII) to give a product of formula (XVIII) is carried out in refluxing acetonitrile for a time between 10 hours to overnight.

According to step (1) of the process, the acidic hydrolysis of a compound of formula (XVIII) to give a product of formula (IV) is carried out in a refluxing mixture of ethanol-trifluoroacetic acid for a time between 8 hours and overnight.

According to any one of steps (m.1) to (m.5) the conversion of a compound of formula (I) in another compound of formula (I), can be carried out in a variety of ways, according to conventional methods.

Preferably according to step (m.1) of the process, the hydrolysis of a compound of formula (I) wherein R1 is —OCH$_2$CH$_3$, to give the corresponding compound of formula (I) wherein R1 is —OH is carried out under acidic or basic conditions. Preferably, the reaction is carried out as described under step (a). According to the operative conditions being employed, the compound of formula (I) wherein R1 is —OH could be obtained either in its acidic form or, alternatively, as a salt.

Preferably according to step (m.2) of the process, the transesterification of a compound of formula (I) wherein R1 is —OCH$_2$CH$_3$, to give the corresponding compound of formula (I) wherein R1 is —OR$^a$ and R$^a$ is an alkyl different from ethyl, is carried out by reaction with a compound of formula (XV) in an appropriate solvent, such as the compound of formula (XV) itself or dioxane at the refluxing temperature, optionally in the presence of a suitable metal based catalysts, like dibutylin oxide or titanium alkoxides such as, for instance, titanium (IV) ethoxide, titanium (IV) isopropoxide and the like.

Preferably according to step (m.3) of the process, the aminolysis of a compound of formula (I) wherein R1 is —OCH$_2$CH$_3$, to give the corresponding compound of formula (I) wherein R1 is —NR$^a$R$^b$, is carried out in an appropriate solvent such as dioxane or dichloromethane optionally in the presence of a suitable metal based catalysts, like trimethyl aluminium.

Preferably according to step (m.4) of the process, the esterification of a compound of formula (I) wherein R1 is a group —OH to give the corresponding compound of formula (I) wherein R1 is —OR$^a$, is carried out in the presence of a suitable condensing agent, for instance dicyclohexylcarbodiimide (DCC), 1-ethyl-3-(3'-dimethylaminopropyl)carbodiimide (EDC), 3,4-dihydro-3-hydroxy-4-oxo-1,2,3-benzotriazine (DHBT), O-benzotriazolyltetramethylisouronium tetrafluoroborate (TBTU), benzotriazol-1-yloxytripyrrolidinophosphonium hexafluorophosphate (PyBOP), or 2-(1H-Benzotriazole-1-yl)-1,1,3,3-tetramethyluronium hexafluorophosphate (HBTU), in an appropriate solvent such as dichloromethane (DCM), N,N-dimethylformamide (DMF) or N,N-dimethylacetamide (DMA).

Preferably according to step (m.5) of the process, the amidation of a compound of formula (I) wherein R1 is a group —OH to give the corresponding compound of formula (I) wherein R1 is —NR$^a$R$^b$ can be carried out in a variety of ways, according to conventional methods for obtaining amido derivatives from the corresponding acids. Preferably, the reaction is carried out by reaction with compound of formula (XV) after activation of the carboxylic function of the compound of formula (I) by reaction with thionyl chloride, oxalyl chloride or alternatively in the presence of a suitable condensing agent, for instance dicyclohexylcarbodiimide (DCC), 1-ethyl-3-(3'-dimethylaminopropyl)carbodiimide (EDC), 3,4-dihydro-3-hydroxy-4-oxo-1,2,3-benzotriazine (HBTOH), O-benzotriazolyltetramethylisouronium tetrafluoroborate (TBTU) or benzotriazol-1-yloxytripyrrolidinophosphonium hexafluorophosphate (PyBOP), in an appropriate solvent such as dichloromethane, and/or N,N-dimethylformamide or N,N-dimethylacetamide. According to any one of steps (n.1) to (n.5) the conversion of a compound of formula (V) into another compound of formula (V) can be carried out in a variety of ways, according to conventional methods.

Preferably it is carried out as described under the steps from (m.1) to (m.5). According to any one of steps (o.1) to (on.5) the conversion of a compound of formula (XI) into another compound of formula (XI) can be carried out in a variety of ways, according to conventional methods.

Preferably it is carried out as described under the steps from (m.1) to (m.5). In addition to the above, the compounds of formula (I) may be advantageously prepared according to combinatorial chemistry techniques widely known in the art, by accomplishing the aforementioned reactions between the intermediates in a serial manner and by working under solid-phase-synthesis (SPS) conditions.

As an example, the intermediate carboxy ester derivatives of formula (Va) being obtained in step (b) of the above processes, can be first converted into the free carboxy acid derivative by means of hydrolysis carried out according to conventional methods, then easily supported onto a polymeric resin, for instance through the formation of a carboxamido group.

The intermediate thus supported may be subsequently reacted according to the remaining steps of the process.

The above synthetic pathway can be summarized as follows:

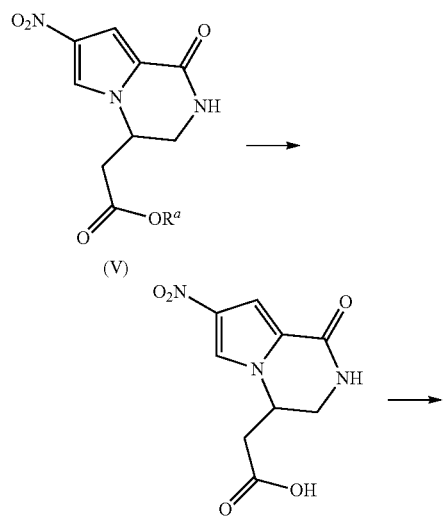

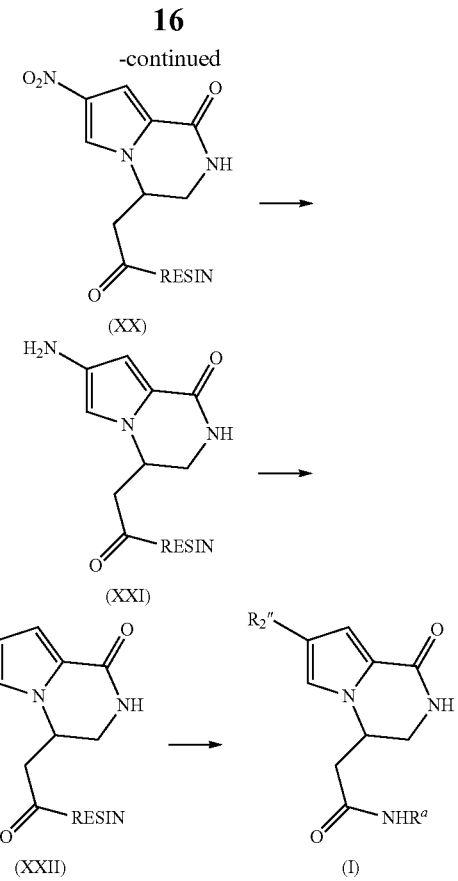

wherein the resin is a commercially available polystyrenic resin including, for instance, Wang resin, Trityl resin, Cl-trityl resin, Rink amide resin, Tentagel OH resin and derivatives thereof, R2″ and R$^a$ are as defined above.

Any of the above reactions is carried out according to known methods, by working as formerly reported, and allows obtaining compounds of formula (I) as set forth above. According to a preferred embodiment of the invention, the polystyrenic resin is a derivatized formyl polystyrenic resin which may be obtained by reacting a commercially available formyl polystyrenic resin, e.g. 4-(4-formyl-3-methoxyphenoxy)butyryl AM resin, with a suitable amino derivative under reductive conditions, for instance in the presence of sodium triacetoxyborohydride and derivatives thereof, substantially as follows:

The reaction may be carried out in a suitable solvent such as tetrahydrofuran and in the presence of acetic acid.

The polymer-supported-amino derivatives thus obtained, particularly those, which are referable to as derivatized formyl polystyrenic resin above, are widely known in the art. In general, amines loaded onto formylpolystyrenic resins also known as Acid Sensitive Methoxyl)enzaldehyde polystyrene resins (AMEBA resin) are prepared by standard reductive amination in the presence of an excess of amine in TMOF/DCE and NaBH(OAc)$_3$ or AcOH/DMF and NaCNBH$_3$, for instance as reported in Tetrahedron Letters (1997), 38, 7151-7154; J. Am. Chem. Soc. (1998), 120, 5441; and Chem. Eur. J. (1999), 5, 2787.

Therefore, it is a further object of the present invention a process for preparing the compounds of formula (I), and the pharmaceutically acceptable salts thereof, which process comprises:

p) hydrolyzing under acid or basic conditions the compound of formula (V) wherein R1 is —OR$^a$ and R$^a$ is C$_1$-C$_6$ alkyl;

r) reacting the resultant acid derivative with a derivatized formyl polystyrenic resin of formula (XIX):

wherein (P) is the resin and R$^a$ is as defined above;

s) reacting of the resultant compound of formula (XX):

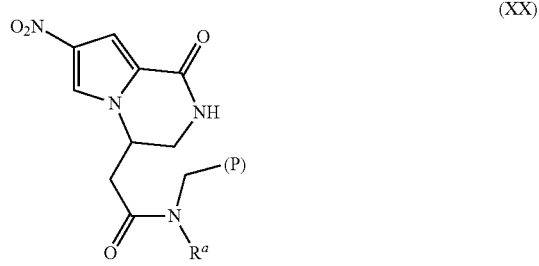

wherein (P) and R$^a$ are as described above, with a suitable reducing agent such as chromium (II) chloride, tetrabutylammonium hydrogen sulfide or tin (II) chloride; and t) reacting the resultant compound of formula (XXI):

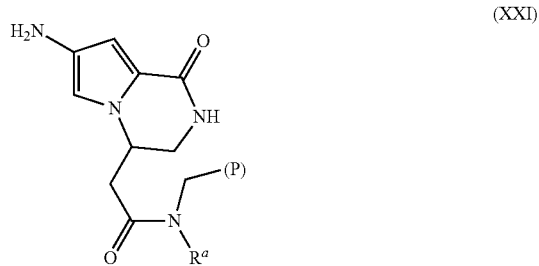

wherein (P) and R$^a$ are as described above, as described under any one of steps (d.1) or (d.2);

u) cleaving the resin under acidic conditions from the resultant compound of formula (XXII):

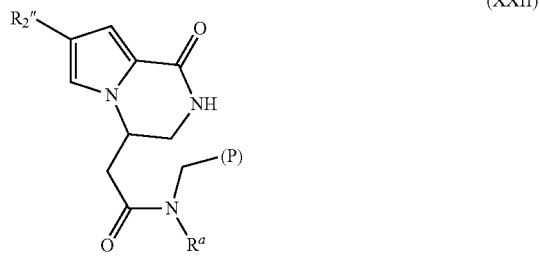

to give a compound of formula (I), wherein R2" is —NHCOR$^c$ or —NHCONHR$^c$, wherein R$^c$ is as defined above, and R1 is —NHR$^a$, wherein R$^a$ is as defined above;

optionally separating the resultant compound of formula (I) into the single isomers; converting the resultant compound of formula (I) into a different compound of formula (I) and/or into a pharmaceutically acceptable salt if desired.

According to step (p) of the process, the hydrolysis of a compound of formula (Va), to give the corresponding compound of formula (V) wherein R1 is —OH is carried out as described under step (m.1).

According to step (r) of the process, the reaction with the polystyrene resin is performed in a suitable solvent, for instance DMF, in the presence of N,N-diisopropylethylamine (DIPEA) and of a suitable condensing agent such as, for instance, benzotriazol-1-yloxytripyrrolidinophosphonium hexafluorophosphate (PyBOP), O-benzotriazolyl tetramethylisouronium tetrafluoroborate (TBTU) or 2-(1H-Benzotriazole-1-yl)-1,1,3,3-tetramethyluronium hexafluorophosphate (HBTU).

According to step (s) of the process, the supported compound of formula (XX) is reduced to obtain the corresponding amino derivative; the reaction is carried out in the presence of tin (II) chloride in dimethylformamide (DMF) at room temperature for a time ranging from 4 to 24 hours.

According to step (t), the supported compound of formula (XXI) is optionally further reacted to give to a variety of compounds functionalised in position 4 of the 3,4-dihydro-2H-pyrrolo[1,2-a]pyrazin-1-one ring, as described under any one of steps from (d.1) and (d.2).

According to step (u), the cleavage of the resin is performed under acidic conditions in the presence of suitable acids such as, for instance, hydrochloric, trifluoroacetic, methanesulfonic or p-toluensulfonic acid. Preferably the reaction is carried out using trifluoroacetic acid in dichloromethane as solvent.

As another example, the intermediate carboxy ester derivatives of formula (XIa) being obtained in step (g) of the above processes, can be first converted into the free carboxy acid derivative by means of hydrolysis carried out according to conventional methods, then easily supported onto a polymeric resin, for instance through the formation of a carboxamido group.

The intermediate thus supported may be subsequently reacted according to the remaining steps of the process.

The above synthetic pathway can be summarized as follows:

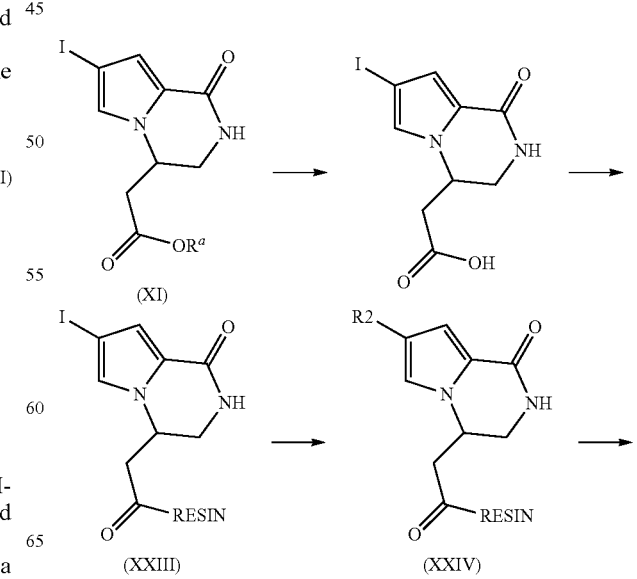

-continued

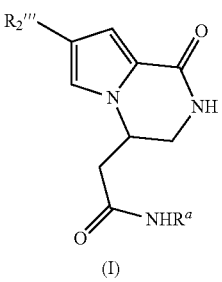

wherein R2, R2''', $R^a$ and the resin are as defined above.

Therefore, it is a further object of the present invention a process for preparing the compounds of formula (I), and the pharmaceutically acceptable salts thereof, which process comprises:

v) hydrolyzing under acid or basic conditions the compound of formula (XI) wherein R1 is —$OR^a$ and $R^a$ is $C_1$-$C_6$ alkyl;

w) reacting the resultant acid derivative with a derivatized formyl polystyrenic resin of formula (XIX):

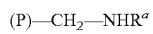

wherein (P) is the resin and $R^a$ is as defined above;

z) reacting of the resultant compound of formula (XXIII):

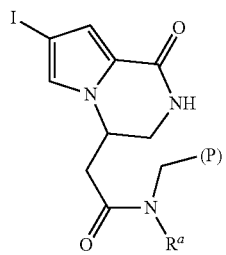

wherein (P) and $R^a$ are as described above, with a boronic acid or ester of formula (XII):

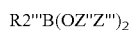

wherein R2''' is $R^d$ and $R^d$ is a group optionally further substituted, selected from straight or branched $C_1$-$C_6$ alkyl, $C_3$-$C_6$ cycloalkyl, cycloalkyl $C_1$-$C_6$ alkyl, heterocyclyl, heterocyclyl $C_1$-$C_6$ alkyl, aryl, aryl $C_1$-$C_6$ alkyl, heteroaryl or heteroaryl $C_1$-$C_6$ alkyl, and Z'' and Z''' are as defined above;

x) cleaving the resin under acidic conditions from the resultant compound of formula (XXVI):

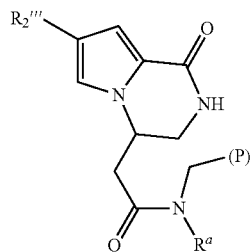

to give a compound of formula (I), wherein R2''' is as defined above and R1 is —$NHR^a$, wherein $R^a$ is as defined above, optionally separating the resultant compound of formula (I) into the single isomers; converting the resultant compound of formula (I) into a different compound of formula (I) and/or into a pharmaceutically acceptable salt if desired.

According to step (v) of the process, the hydrolysis of a compound of formula (XIa) is carried out as described under step (m.1) and step (p).

According to step (w) of the process, the reaction with the polystyrene resin is performed as described under step (r).

According to step (z) of the process, the reaction with the boronic acid or ester of formula (XII) wherein R2''' is aryl or heteroaryl, is performed as described under step (h.1).

According to step (x) of the process, the cleavage of the resin is performed as described under step (u).

Clearly, by working according to combinatorial chemistry techniques as formerly indicated, a plurality of compounds of formula (I) may be obtained.

Hence, it is a further object of the present invention a library of two or more compounds of formula (I)

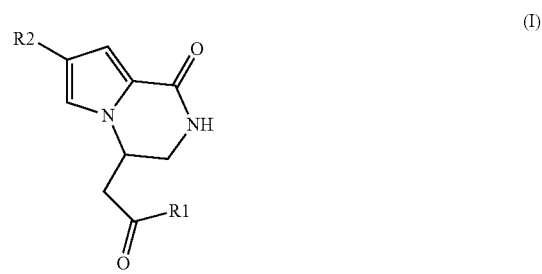

wherein

R1 is a group —$NR^aR^b$ or —$OR^e$;

R2 is —$NH_2$, —$NHCOR^c$, —$NHCONHR^c$, —$NHSO_2R^c$, —C≡$CR^d$ or $R^d$ wherein $R^a$, $R^b$, $R^c$ and $R^d$, the same or different, are each independently hydrogen or a group optionally further substituted, selected from straight or branched $C_1$-$C_6$ alkyl, $C_2$-$C_6$ alkenyl or $C_2$-$C_6$ alkynyl, $C_3$-$C_6$ cycloalkyl, cycloalkyl $C_1$-$C_6$ alkyl, heterocyclyl, heterocyclyl $C_1$-$C_6$ alkyl, aryl, aryl $C_1$-$C_6$ alkyl, heteroaryl and heteroaryl $C_1$-$C_6$ alkyl, or $R^a$ and $R^b$, taken together with the nitrogen atom to which they are bonded, may form an optionally substituted 3 to 7 membered heterocyclyl or heteroaryl, optionally containing one additional heteroatom or heteroatomic group selected from S, O, N or NH, and pharmaceutically acceptable salts thereof.

According to a preferred embodiment of the invention, the aforementioned library comprises the compounds of formula (I) wherein R1 is a group —$NR^aR^b$ and $R^a$ and $R^b$ are both hydrogen atoms or one of them is a hydrogen atom and the remaining one of $R^a$ or $R^b$ is a straight or branched $C_1$-$C_6$ alkyl or $C_2$-$C_6$ alkenyl group or it is an optionally substituted aryl or aryl $C_1$-$C_6$ alkyl group.

Also preferred is a library of compounds of formula (I) wherein R2 is a group —$NHCOR^c$ with $R^cC$ as a straight or branched $C_1$-$C_6$ alkyl, cycloalkyl or optionally substituted aryl or arylalkyl group.

Also preferred is a library of compounds of formula (I) wherein R2 is a group —$NHCONHR^c$ with $R^c$ as a hydrogen atom or as a straight or branched $C_1$-$C_6$ alkyl, optionally substituted aryl or arylalkyl group.

For a general reference to the above libraries of compounds of formula (I) see the experimental section.

From all of the above, it is clear to the skilled person that once a library of 3,4-dihydro-2H-pyrrolo[1,2-a]pyrazin-1-one derivatives is thus prepared, for instance consisting of about a thousands of compounds of formula (I), the said library can be very advantageously used for screening towards given kinases, as formerly reported.

See, for a general reference to libraries of compounds and uses thereof as tools for screening biological activities, J. Med. Chem. 1999, 42, 2373-2382; and Bioorg. Med. Chem. Lett. 10 (2000), 223-226.

Pharmacology

The inhibiting activity of putative kinase inhibitors and the potency of selected compounds is determined through a method of assay based on the use of the Kinase-Glo® Luminescent Kinase Assay (commercially available from Promega corporation and described in Koresawa, M. and Okabe, T. (2004) High-throughput screening with quantitation of ATP consumption: A universal non-radioisotope, homogeneous assay for protein kinase. *Assay Drug Dev. Technol.* 2, 153-60).

The depletion of ATP as a result of kinase activity can be monitored in a highly sensitive manner through the use of Kinase-Glo® or Kinase-Glo® Plus Reagent, which uses luciferin, oxygen and ATP as substrates in a reaction that produces oxyluciferin and light.

The short forms and abbreviations used herein have the following meaning:

BSA bovine serum albumine
Tris 2-Amino-2-(hydroxymethyl)-1,3-propanediol
Hepes N-(2-Hydroxyethyl)piperazine-N'-(2-ethanesulfonic acid)
DTT threo-1,4-Dimercapto-2,3-butanediol
THF tetrahydrofuran
MTBE methyl tertiary butyl ether
DIPEA N,N-diisopropylethylamine
PyBOP benzotriazol-1-yloxytris(pyrrolidino)phosphonium exafluorophosphate
EDC 1-ethyl-3-(3'-dimethylaminopropyl)carbodiimide
DHBT 3,4-dihydro-3-hydroxy-4-oxo-1,2,3-benzotriazine
HBTU 2-(1H-Benzotriazole-1-yl)-1,1,3,3-tetramethyluronium hexafluorophosphate
TFA trifluoroacetic acid
TMOF trimethyl orto formate
DCE dichloroethane
DCM dichloromethane
DMF N,N-dimethylformammide
DMA N,N-dimethylacetamide
DMSO dimethylsulfoxide
KDa kiloDalton
mg milligram
μg microgram
ng nanogram
L liter
mL milliliter
μL microliter
M molar
mM millimolar
IM micromolar
nM nanomolar Kinase reaction conditions are target (enzyme) dependent and thus undergo individual adaptations. The Kinase-Glo® Luminescent Kinase Assay can be used with virtually any kinase and substrate combination.

Also the buffer conditions may vary depending on the kinase of interest (e.g for PKA a composition of 40 mM Tris pH 7.5, 20 mM $MgCl_2$, 0.1 mg/ml BSA, in 50 μl final volume is used). Typically the range of ATP titration is 0.1 μM to 10 μM.

The optimal kinase substrate results in the greatest change in luminescence when comparing kinase reaction wells with no kinase wells.

The optimal amount of kinase is determined by making two fold serial dilutions across plates using the optimal amount of ATP and optimal kinase substrate. The optimal amount of kinase to use in subsequent compound screens and $IC_{50}$ determinations is the amount required for luminescence to be within the linear range of the kinase titration curve (sigmoidal dose response).

Robotized Kinase-Glo® Assay

This assay was set up for the measurement of kinase activity and/or inhibition. It is homogeneous, suitable for all type of protein kinases, quick and radioactivity-free.

We established the assay in 384 well-plates: the test mix consisted of:

1) 3× Enzyme mix (done in Kinase Buffer 3×), 5 μl/well
2) 3× substrate and ATP mix (done in $ddH_2O$), 5 μl/well
3) 3× compound of formula (I) (diluted into $ddH_2O$—3% DMSO)-5 μl/well)

As an outcome, the percentage of inhibition at 10 μM was evaluated for each compound tested: see below for compound dilution and assay scheme. Each enzyme had its own buffer constitution, substrate type and concentration. Incubation time instead was 90 min for all targets.

Test compounds were received as a 1 mM solution in 100% DMSO into 96 well plates. The plates were diluted to 30 μM in $ddH_2O$, 3% DMSO; 4 plates are reorganized in 384 well plate by dispensing 5 μl of each 96 wp into the four quadrants of a 384 wp. In well P23 and P24 the internal standard inhibitor staurosporine was added.

Assay Scheme

Test plates were first added with 5 μl of the compound dilution (30 μM, corresponding to 3× dilution) and then loaded onto a robotized station together with one reservoir for the Enzyme mix (3×) and one for the ATP mix (3×), specific for each target under study.

To start the assay, the robot aspirated 5 μl of ATP/Substrate mix, made an air gap inside the tips (5 μl) and aspirated 5 μl of Enzyme mix. The subsequent dispensation into the test plates allowed the kinase reaction to start after 3 cycles of mixing, done by the robot itself by up and down pipetting. At this point, the correct concentration was restored for all reagents.

The robot incubated the plates for 90 minutes at room temperature, and then stopped the reaction by pipetting 15 μl of Kinase-Glo® reagent into the reaction mix. Three cycles of mixing were done immediately after the addition of the reagent.

The principle of the Kinase-Glo® technique is the presence in the reagent mixture of oxygen, luciferin and luciferase enzyme: in the presence of ATP, remaining from the kinase reaction, oxi-luciferin is produced with the emission of light, directly dependent on the amount of ATP. For optimal performances of this technique, the kinase reaction should utilize at least 15-20% of the available ATP.

After another 60 minutes of incubation to stabilize the luminescent signal, the plates were read on a ViewLux® instrument. Data were analyzed using the software package Assay Explorer® that provided percent inhibition data.

As example herein are reported the assay conditions used for testing the compounds of formula (I) against ALK (the ALK protein was prepared as described in WO2009013126, the substrate ALKtide YFF APCo was obtained in batches of >95% peptide purity from American Peptide Company, Inc. (Sunnyvale, Calif., USA).

Assay Conditions:
ATP concentration: 1 µM
Enzyme concentration: 100 nM
Substrate concentration ALKtide YFF APCo: 80 µM
Reaction buffer: Hepes 50 mM pH 7.5, MgCl2 5 mM, MnCl2 1 mM, DTT 1 mM, NaVO₃ 3 uM, 0.2 mg/ml BSA Assay procedure: add 5 ul compound of formula (I) (3×), add 5 µl ATP/S mix(3×) in buffer 1x; add 5 µl enzyme in buffer 2x+3×BSA; for the blank, add 5 µl buffer 2x+3x BSA without enzyme. After 90 minutes of incubation, add 15 µl/well of Kinase-Glo reagent. After 60-90 minutes of incubation to stabilize the luminescent signal, the plates are read on a ViuwLux instrument.

The compounds of the present invention were found active at a concentration from to 10000 nM.

Biochemical Assay for Inhibitors of PIM-1 Kinase Activity

The inhibitory activity of putative kinase inhibitors and the potency of selected compounds were determined using a trans-phosphorylation assay.

Specific peptide or protein substrates are trans-phosphorylated by their specific ser-thr or tyr kinase in the presence of ATP traced with $^{33}$P-γ-ATP, and in the presence of their own optimal buffer and cofactors.

At the end of the phosphorylation reaction, more than 98% unlabeled ATP and radioactive ATP is captured by an excess of the ion exchange dowex resin; the resin then settles down to the bottom of the reaction plate by gravity.

Supernatant is subsequently withdrawn and transferred into a counting plate, then evaluated by β-counting.

Reagents/Assay Conditions i. Dowex Resin Preparation 500 g of wet resin (SIGMA, custom prepared resin DOWEX 1×8 200-400 mesh, 2.5 Kg) are weighed out and diluted to 2 1 in 150 mM sodium formate, pH 3.00.

The resin is allowed to settle down (some hours) and then the supernatant is discarded.

After three washes as above over a couple of days, the resin is allowed to settle and two volumes (wrt the resin volume) of 150 mM sodium formate buffer are added.

The pH is then measured and should be around 3.00

The washed resin is stable for more than one week; the stock resin is kept at 4° C. before use.

ii. Kinase Buffer (KB)

The buffer for PIM-1 assay was composed of HEPES 50 mM, at pH 7.5, with 10 mM MgCl₂, 1 mM DTT, 3 µM NaVO₃, and 0.2 mg/ml BSA Full-length human PIM-1 was expressed and purified as described in Bullock A N, et Al J. Biol. Chem. 2005, 280, 41675-82.

The enzyme showed a linear kinetic after a step of pre-activation by auto-phosphorylation in the following conditions:

1.7 µM PIM1 was incubated 1 hour RT at 280 C in the presence of 125 µM ATP

Iii. Assay Conditions
ATP concentration: 200 µM
$^{33}$P-µ-ATP: 6 nM
Enzyme concentration: 1 nM
Substrate concentration Aktide (Chemical Abstract Service Registry Number 324029-01-8): 25 µM Robotized Dowex Assay The test mix consisted of:
1) 3× Enzyme mix (done in Kinase Buffer 3×), 5 µL/well
2) 3× substrate and ATP mix (done in ddH₂O), together with $^{33}$P-γ-ATP, 5 µL/well
3) 3× test compounds (diluted into ddH₂O-3% DMSO)-5 µL/well See below for compound dilution and assay scheme
Compound Dilution and Assay Scheme is Defined Below:
i. Dilution of Compounds Test compounds are received as a 1 mM solution in 100% DMSO, distributed into 96 or 384 well plates:

a) for percent inhibition studies (HTS), individual dilution plates at 1 mM are diluted at a 3× concentration (30 µM) in ddH₂O (3% DMSO=final concentration) using a Beckman NX automated pipetting platform. The same instrument is used for distributing the diluted mother plates into the test plates.

b) for IC50 determination (KSS platform), 100 µl of each compound at 1 mM in 100% DMSO are transferred from the original plate into the first column of another 96 well plate (A1 to G1); well H1 is left empty for the internal standard inhibitor, usually staurosporine.

An automated station for serial dilutions (Biomek FX, Beckman) is used for producing 1:3 dilutions in 100% DMSO, from line A1 to A10, and for all the seven compounds in the column. Moreover, 4-5 copies of daughter plates are prepared by reformatting 5 µL of this first set of 100% DMSO dilution plates into 384 deep well-plates: one copy of the daughter plates with the serial dilutions of test compounds will be thaw the day of the experiments, reconstituted at a 3× concentration with water and used in the IC50 determination assays. In a standard experiment, the highest concentration (3×) of all compounds is 30 µM, while the lowest one is 1.5 nM.

Each 384 well-plate will contain reference wells (total enzyme activity vs. no enzymatic activity) for the Z' and signal to background evaluation.

ii. Assay Scheme 384-well plates, V bottom (test plates) are prepared with 5 µL of the compound dilution (3×) and then placed onto a PlateTrak 12 robotized station (Perkin Elmer; the robot has one 384-tips pipetting head for starting the assay plus one 96-tips head for dispensing the resin) together with one reservoir for the Enzyme mix (3×) and one for the ATP mix (3×). At the start of the run, the robot aspirates 5 µL of ATP mix, makes an air gap inside the tips (2 µL) and aspirates 2 µL of PIM mix. The following dispensation into the plates allows the kinase reaction to start upon 3 cycles of mixing, done by the robot itself.

At this point, the correct concentration is restored for all reagents.

The robot incubates the plates for 60 minutes at room temperature, and then stops the reaction by pipetting 70 µL of dowex resin suspension into the reaction mix. Three cycles of mixing are done immediately after the addition of the resin.

The resin suspension is very dense; in order to avoid tip clogging, wide bore tips are used to dispense it.

Another mixing cycle is performed after all the plates are stopped, this time using normal tips: the plates are then allowed to rest for about one hour in order to maximize ATP capture. At this point, 20 µL of the supernatant are transferred into 384-Optiplates (Perkin-Elmer), with 70 µL of Microscint 40 (Perkin-Elmer); after 5 min of orbital shaking the plates are read on a Perkin-Elmer Top Count radioactivity counter.

iii. Data Analysis

Data are analysed by an internally customized version of the SW package "Assay Explorer" that provides either % inhibition for primary assays or sigmoidal fittings of the ten-dilutions curves for IC50 determination in the secondary assays/hit confirmation routines.

Biochemical assay for inhibitors of PIM-2 kinase activity

The inhibitory activity of putative kinase inhibitors and the potency of selected compounds were determined using a trans-phosphorylation assay as described above for PIM-1.

i. Kinase Buffer (KB)

The buffer for PIM-2 assay was composed of HEPES 50 mM, at pH 7.5, with 1 mM $MgCl_2$, 1 mM DTT, 3 μM $NaVO_3$, and 0.2 mg/ml BSA Full-length human PIM-2 was expressed and purified as described in Fedorov O, et al, PNAS 2007 104, 51, 20523-28).

ii. Assay Conditions

ATP concentration: 4 μM $^{33}$P-μ-ATP: 1 nM

Enzyme concentration: 1.5 nM

Substrate concentration Aktide (Chemical Abstract Service Registry Number 324029-01-8): 5 μM The enzyme showed a linear kinetic without the need of any step of pre-activation.

Robotized Dowex Assay

See the same procedure described for PIM-1.

The compounds of the present invention showed IC50 of less 10 μM when tested against PIM-1 and PIM-2, see table A below for some examples.

In Table A, the tested compounds are identified with a code that is explained below. When the diastereoisomers are resolved, the chirality is to be intended on the 3,4-dihydro-2H-pyrrolo[1,2-a]pyrazin-1-one scaffold.

TABLE A

| Compound | PIM-1 IC50 μM | PIM-2 IC50 μM |
|---|---|---|
| A33-M-B22 | 0.46 | 5.03 |
| A33-M-B30 | 0.58 | 1.92 |
| A127-M-B14 | 0.18 | 2.74 |
| A127-M-B22 | 0.07 | 2.46 |
| A127-M-B30 | 0.19 | 1.67 |
| A127-M-B32 | 0.61 | 10 |
| A127-M-B39 | 0.57 | 1.15 |
| A127-M-B40 | 0.23 | 4.81 |
| A127-M-B47 | 0.52 | 2.25 |
| A128-M-B14 | 0.20 | 2.11 |
| A128-M-B22 | 0.12 | 3.12 |
| A128-M-B30 | 0.27 | 2.03 |
| A128-M-B32 | 0.70 | 7.55 |
| A128-M-B39 | 0.54 | 0.87 |
| A128-M-B40 | 0.25 | 4.50 |
| A129-M-B14 | 0.28 | 4.51 |
| A129-M-B22 | 0.13 | 5.92 |
| A129-M-B30 | 0.12 | 1.25 |
| A132-M-B22 | 0.36 | 10 |
| A133-M-B14 | 0.81 | 7.40 |
| A133-M-B22 | 0.38 | 10 |
| A133-M-B28 | 0.84 | 3.13 |
| A133-M-B30 | 0.61 | 3.62 |
| A134-M-B14 | 0.72 | 7.22 |
| A134-M-B28 | 0.36 | 1.50 |
| A134-M-B30 | 0.89 | 5.80 |
| A137-M-B14 | 0.40 | 3.46 |
| A137-M-B39 | 0.92 | 3.56 |
| A139-M-B14 | 0.22 | 3.44 |
| A139-M-B22 | 0.09 | 4.47 |
| A139-M-B30 | 0.41 | 3.37 |
| A139-M-B39 | 0.98 | 3.05 |
| A139-M-B40 | 0.13 | 2.22 |
| A140-M-B30 | 0.49 | 10 |
| A142-M-B14 | 4.83 | 6.62 |
| A142-M-B28 | 3.72 | 4.15 |
| A142-M-B30 | 2.52 | 2.58 |
| A144-M-B14 | 10.00 | 4.92 |
| A144-M-B22 | 0.48 | 0.66 |
| A144-M-B30 | 1.10 | 0.68 |
| A150-M-B14 | 0.14 | 1.52 |
| A150-M-B24 | 0.21 | 4.06 |
| A150-M-B25 | 0.45 | 5.86 |
| A150-M-B26 | 0.24 | 5.51 |
| A150-M-B32 | 0.23 | 4.49 |
| A150-M-B36 | 1.39 | 8.98 |

TABLE A-continued

| Compound | PIM-1 IC50 μM | PIM-2 IC50 μM |
|---|---|---|
| A150-M-B38 | 1.06 | 7.51 |
| A150-M-B39 | 0.22 | 0.60 |
| A150-M-B40 | 0.04 | 0.98 |
| A150-M-B42 | 0.59 | 10 |
| A150-M-B43 | 0.79 | 5.89 |
| A150-M-B45 | 0.58 | 4.65 |
| A150-M-B48 | 0.12 | 2.86 |
| A150-M-B49 | 0.23 | 1.61 |
| A150-M-B52 | 0.43 | 5.17 |
| A151-M-B14 | 0.10 | 2.25 |
| A151-M-B32 | 0.49 | 10 |
| A151-M-B39 | 4.11 | 3.69 |
| A133-M-B61 isomer R | 5.94 | 10 |
| A127-M-B61 isomer R | 0.38 | 3.90 |
| A157-M-B61 isomer R | 0.27 | 2.83 |
| A158-M-B61 isomer R | 0.86 | 5.55 |
| A133-M-B61 isomer S | 0.07 | 4.79 |
| A127-M-B61 isomer S | 0.02 | 0.25 |
| A133-M-B62 isomer R | 4.83 | 10 |
| A127-M-B62 isomer R | 1.84 | 2.62 |
| A157-M-B62 isomer R | 1.14 | 1.05 |
| A158-M-B62 isomer R | 0.55 | 0.66 |
| A133-M-B62 isomer S | 0.13 | 1.33 |
| A127-M-B62 isomer S | 0.09 | 0.52 |
| A133-M-B63 | 2.54 | 10 |
| A127-M-B63 | 0.39 | 2.44 |
| A157-M-B63 | 0.69 | 2.37 |
| A158-M-B63 | 0.40 | 3.05 |
| A133-M-B64 isomer R | 2.04 | 10 |
| A127-M-B64 isomer R | 2.91 | 10 |
| A157-M-B64 isomer R | 0.70 | 2.81 |
| A133-M-B64 isomer S | 0.56 | 2.92 |
| A127-M-B64 isomer S | 0.14 | 0.68 |
| A133-M-B65 isomer S | 0.05 | 0.82 |
| A127-M-B65 isomer S | 0.01 | 0.18 |
| A157-M-B65 isomer S | 0.01 | 0.10 |
| A157-M-B65 isomer R | 0.15 | 0.50 |
| A158-M-B65 isomer S | 0.03 | 0.18 |

From all of the above, the novel compounds of formula (I) of the invention appear to be particularly advantageous in the therapy of diseases caused by dysregulated protein kinase activity such as cancer.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim of better illustrating the present invention, without posing any limitation to it, the following examples are now given.

EXPERIMENTAL SECTION

General Methods

Flash Chromatography was performed on silica gel (Merck grade 9395, 60A). The high-pressure liquid chromatography retention times (HPLC: r.t. values) were determined by:

HPLC Method 1:

A Waters Alliance LC mod. 2795 equipped with a variable UV detector mod 2487, a Chemiluminescence Nitrogen detector (CLND, Antek 8060) and a Waters ZQ2000 mass detector (ESI interface) was used in this application. The total flow was splitted and distributed to the three detectors at a fixed ratio (64:15:21 UV:MS:CLND). The liquid chromatograph was equipped with a 30×3.0 mm I.D. column (Waters xBridge C18, 3.5 um particles), thermostated at 50° C. Two mobile phases were used: phase A was 0.05% w/v formic acid (1 mL/L of 50% formic acid Fluka 09676 in highly purified water) and phase B was 70/25/5 (v/v/v) MeOH/iPrOH/H2O containing 0.035% w/v of formic acid (700 uL/L of 50% formic acid Fluka 09676).

A 5 uL volume of 1 mM nominal sample solution in DMSO was injected (sequential, partial loop mode with no air gaps) and a generic reversed phase gradient analysis (classified as method "#IN63SEQ79") was carried out at 0.8 mL/min from 0% to 100% of phase B (v/v) over 5 min, held 0.7 min at 100% B and steeply reverted to 0% B at 5.71 min, with the run stop time set at 6.3 min. The total analysis time ("between injections") was 7.9 min. The UV detector was operated at 220 nm, 5 Hz sampling rate. The MS device was operated at 3.2 kV capillary voltage, 30 V cone, 2 V extractor, 0.5 V RF lens, 400 L/hr desolvation flow, 100 L/hr cone flow, 100° C. source temperature, 150° C. desolvation temperature, ESI(+) full scan 120-1200 amu acquisition, at 1.7 Hz sampling rate. The CLND detector was operated at 1050° C. furnace temp, 280 mL/min inlet oxygen flow, 80 mL/min inlet argon, mL/min make-up argon, 30 mL/min ozone, 28 torr vacuum, 750 V PMT voltage, PMT chamber at +10° C., sensitivity high, select 5, 4 Hz sampling rate.

HPLC Method 2:

HPLC-MS analyses were performed on a Finnigan MAT mod. LCQ ion trap mass spectrometer, equipped with an ESI (Electrospray) ion source, the mass spectrometer is directly connected to a HPLC SSP4000 (Thermo Separation) equipped with an autosampler Lc Pal (CTC Analytics) and an UV6000LP PDA detector.

HPLC Conditions:

Column: Phenomenex Gemini C18, 3 µm, 50×4.6 mm (default)

Temperature 40° C.

Mobile phase A: Acetate Buffer 5 mM pH 4.5: acetonitrile 95:5 (v:v)

Mobile phase B: Acetate Buffer 5 mM pH 4.5: acetonitrile 5:95 (v:v)

Elution Gradient:

| Time (min) | % Mobile Phase A |
|---|---|
| 0 | 100 |
| 7 | 0 |
| 9 | 0 |
| 11 | 100 |
| 13 | 100 |

Flow rate: 1 mL/min Injection volume: 10 μL
Column temperature: 40° C.

MS conditions: The LCQ mass spectrometer operates with an electrospray ionization (ESI) interface in positive and negative ion mode following the operation parameters reported in table 1. MS/MS experiments are performed on the most intense ion of each scan automatically by Xcalibur software. A 45% collision energy was used for the fragmentation of the precursor ions.

TABLE 1

Mass Spectrometer Instrument parameters

| Parameter | Value |
|---|---|
| Capillary Temperature (° C.) | 255 |
| Source Voltage (kV) | 4.00 |
| Capillary Voltage (V) | 21.0 |
| Tube Lens Offset (V) | −5.0 |
| Multipole RF Amplifier (Vp-p) | 400.0 |
| Multipole 1 Offset (V) | −3.00 |
| Multipole 2 Offset (V) | −6.50 |
| InterMultipole Lens Voltage (V) | −16.00 |
| Trap DC Offset Voltage (V) | −10.00 |
| Full Micro scans | 3 |
| Full AGC Target Ions | $5*10^7$ |
| Full Max Ion Time (ms) | 150 |
| MSn Micro scans | 3 |
| MSn AGC Target Ions | $2*10^7$ |
| MSn Max Ion Time (ms) | 200 |
| Electron Multiplier (V) | −950.0 |

HPLC Method 3:

HPLC-MS analyses were performed on a Finnigan MAT mod. LCQ ion trap mass spectrometer, equipped with an ESI (Electrospray) ion source, the mass spectrometer is directly connected to a HPLC SSP4000 (Thermo Separation) equipped with an autosampler Lc Pal (CTC Analytics) and an UV6000LP PDA detector.

HPLC conditions:
Column: Phenomenex Gemini C18, 3 μm, 50×4.6 mm (default)
Temperature 40° C.
Mobile phase A: Acetate Buffer 5 mM pH 4.5: acetonitrile 95:5 (v:v)
Mobile phase B: Acetate Buffer 5 mM pH 4.5: acetonitrile 5:95 (v:v)
Elution gradient:

| Time (min) | % Mobile Phase A |
|---|---|
| 0 | 100 |
| 2 | 80 |
| 9 | 60 |
| 10 | 0 |
| 12 | 0 |
| 12.10 | 100 |

Flow rate: 1 mL/min
Injection volume: 10 μL
Column temperature: 40° C.

MS Conditions:
The LCQ mass spectrometer operates with an electrospray ionization (ESI) interface in positive and negative ion mode following the operation parameters reported in table 2. MS/MS experiments are performed on the most intense ion of each scan automatically by Xcalibur software. A 45% collision energy was used for the fragmentation of the precursor ions.

TABLE 2

Mass Spectrometer Instrument parameters

| Parameter | Value |
|---|---|
| Capillary Temperature (° C.) | 255 |
| Source Voltage (kV) | 4.00 |
| Capillary Voltage (V) | 21.0 |
| Tube Lens Offset (V) | −5.0 |
| Multipole RF Amplifier (Vp-p) | 400.0 |
| Multipole 1 Offset (V) | −3.00 |
| Multipole 2 Offset (V) | −6.50 |
| InterMultipole Lens Voltage (V) | −16.00 |
| Trap DC Offset Voltage (V) | −10.00 |
| Full Micro scans | 3 |
| Full AGC Target Ions | $5*10^7$ |
| Full Max Ion Time (ms) | 150 |
| MSn Micro scans | 3 |
| MSn AGC Target Ions | $2*10^7$ |
| MSn Max Ion Time (ms) | 200 |
| Electron Multiplier (V) | −950.0 |

HPLC Method 4:

Analyses were performed on a Waters Acquity UPLC™ System equipped with a 2996 PDA (UV-VIS), and Acquity ELSD™ detectors. The LC system was coupled to a Waters Acquity 3100 SQD™ single quadrupole mass spectrometer for atomic mass determinations. A Waters Acquity UPLC™ BEH C18, 1.7 μm, 2.1×50 mm column at 45° C. was used with a flow rate of 0.7 mL/min of the following binary solvent system and gradient.

Mobile Phase A: 0.1% Trifluoroacetic Acid in $H_2O$/Acetonitrile (95:5)
Mobile Phase B: Acetonitrile/$H_2O$ (95:5)

| Time (min) | % Mobile Phase A | % Mobile Phase B |
|---|---|---|
| 0.00 | 95% | 5% |
| 2.00 | 5% | 95% |

MS Conditions:
The LCQ mass spectrometer operates with an electrospray ionization (ESI) interface in positive and negative ion mode following the operation parameters reported in table 3. MS/MS experiments are performed on the most intense ion of each scan automatically by Xcalibur software. A 45% collision energy was used for the fragmentation of the precursor ions.

TABLE 3

Mass Spectrometer Instrument parameters

| Parameter | Value |
|---|---|
| Ionization Mode | ESI+ and ESI− |
| Capillary Voltage | 3 kV (ES+); 3 kV (ES−) |
| Cone Voltage | 30 V (ES+); 30 V (ES−) |
| Extractor Voltage | 1 V |
| RF Lens Voltage | 0.1 V |
| Source Temperature | 120° C. |
| Desolvation Temperature | 350° C. |
| Cone Gas Flow | 100 L/Hr |
| Desolvation Gas Flow | 600 L/Hr |
| LM Resolution | 15.0 |

TABLE 3-continued

| Mass Spectrometer Instrument parameters | |
| --- | --- |
| HM Resolution | 15.0 |
| Ion Energy | 0.3 |
| Gain | 1 |
| Scan Mode | Full Scan (Range = 100-800 m/z) ScanTime = 0.1 s Inter-Scan Delay = 0.02 s |

HPLC Method 5:

Analyses were performed on a Waters Alliance HT 2795 System equipped with a 996 PDA (UV-VIS) detector. The LC system was coupled to a Waters/Micromass ZQ™ single quadrupole mass spectrometer for atomic mass determinations. A Waters Ascentis Express C18, 2.7 µm, 4.6×50 mm column was used with a flow rate of 1.0 mL/min of the following binary solvent system and gradient.

Mobile Phase A: 0.1% Trifluoroacetic Acid in $H_2O$/Acetonitrile (95:5)

Mobile Phase B: Acetonitrile/$H_2O$ (95:5)

| Time (min) | % Mobile Phase A | % Mobile Phase B |
| --- | --- | --- |
| 0.00 | 90% | 10% |
| 4.00 | 10% | 90% |
| 4.10 | 0% | 100% |

MS Conditions:

The LCQ mass spectrometer operates with an electrospray ionization (ESI) interface in positive and negative ion mode following the operation parameters reported in table 4. MS/MS experiments are performed on the most intense ion of each scan automatically by Xcalibur software. A 45% collision energy was used for the fragmentation of the precursor ions.

TABLE 4

| Mass Spectrometer Instrument parameters | |
| --- | --- |
| Ionization Mode | ESI+ and ESI− |
| Capillary Voltage | 3.48 kV (ES+); 2.76 kV (ES−) |
| Cone Voltage | 15 V (ES+); 27 V (ES−) |
| Extractor Voltage | 1 V |
| RF Lens Voltage | 0.1 V |
| Source Temperature | 120° C. |
| Desolvation Temperature | 240° C. |
| Cone Gas Flow | 100 L/Hr |
| Desolvation Gas Flow | 600 L/Hr |
| LM Resolution | 15.0 |
| HM Resolution | 15.0 |
| Ion Energy | 0.5 |
| Multiplier | 600 |
| Scan Mode | Full Scan (Range = 100-800 m/z) ScanTime = 0.5 s; Inter-Scan Delay = 0.3 s |

Retention times (HPLC r.t.) are given in minutes at 220 nm or at 254 nm. Mass is given as m/z ratio.

When necessary, the compounds were purified by preparative HPLC using one of the following two systems. A Waters X-Bridge Prep Shield RP 18 (19×100 mm, 5 µm) column or a Phenomenex Gemini C18 (21.2×250 mm, 10 µm) column, using a Waters FractionLynx Autopurification System equipped with a 996 Waters PDA detector and a Micromass mod. ZQ single quadrupole mass spectrometer, electron spray ionization, positive mode. Mobile phase A was water 0.05% $NH_3$/acetonitrile 95:5, and Mobile phase B was acetonitrile. Gradient from 10 to 90% B in 8 min or 15 min. Flow rate 20 ml/min.

Alternatively, purifications were performed on a Biotage Parallex Flex System, equipped with four independent, binary flow-stream pumps, a UV detector with four-channel flow cell monitoring two wavelengths (220 and 254 nm), and four fraction collectors. Fractionation was performed at 254 nm. Waters XTerra Prep RP18, 5 µm, 100×19 mm columns were used at a flow rate of 20 mL/min. Gradients were applied according to the retention time of the desired product obtained from the analytical HPLC analysis.

Standard Binary Solvent System:

Mobile Phase A: 0.1% Trifluoracetic Acid in $H_2O$/Acetonitrile (95:5)

Mobile Phase B: Acetonitrile

Gradient A:

| Time (min) | % Mobile Phase A | % Mobile Phase B |
| --- | --- | --- |
| 0.0 | 100% | 0% |
| 6.0 | 80% | 20% |
| 8.0 | 80% | 50% |
| 8.5 | 50% | 100% |

Gradient B:

| Time (min) | % Mobile Phase A | % Mobile Phase B |
| --- | --- | --- |
| 0.0 | 100% | 0% |
| 6.0 | 70% | 30% |
| 8.0 | 0% | 100% |

Gradient C:

| Time (min) | % Mobile Phase A | % Mobile Phase B |
| --- | --- | --- |
| 0.0 | 100% | 0% |
| 6.0 | 50% | 50% |
| 8.0 | 0% | 100% |

Gradient D:

| Time (min) | % Mobile Phase A | % Mobile Phase B |
| --- | --- | --- |
| 0.0 | 90% | 10% |
| 6.0 | 30% | 70% |
| 8.0 | 0% | 100% |

$^1$H-NMR spectrometry was performed on a Bruker AVANCE 400 MHz single bay instrument with gradients. It is equipped with a QNP probe (interchangeable 4 nuclei probe—$^1$H, 13C, 19F and 31P) (NMR method 1) or on a Mercury VX 400 operating at 400.45 MHz equipped with a 5 mm double resonance probe [1H (15N-31P) ID_PFG Varian] (NMR method 2).

The compounds of formula (I), having an asymmetric carbon atom and obtained as racemic mixture, were resolved by HPLC separation on chiral columns. In particular, for example, preparative columns CHIRALPACK® AD, CHIRALPACK® AS, CHIRALCELL® OJ can be used.

Alternatively, when R1 contains a chiral center and gives rise to a pair of diastereomers, traditional reversed phase HPLC techniques described above were utilized to resolve the species.

Some compounds prepared according to solution and combinatorial chemistry techniques have been conveniently and unambiguously identified, as per the coding system of tables III together with HPLC retention time (methods 1-5) and mass.

Each code, which identifies a single specific compound of formula (I), consists of three units A-M-B.

A represents any substituent R2—[see formula (I)] and is attached in position 7 of the 3,4-dihydro-2H-pyrrolo[1,2-a]pyrazin-1-one moiety; each A substituent is represented in the following table I.

B represents any substituent R1—[see formula (I)] and is attached to the rest of the 3,4-dihydro-2H-pyrrolo[1,2-a]pyrazin-1-one moiety through the carbon atom of the carbonyl group so as to get 3,4-dihydro-2H-pyrrolo[1,2-a]pyrazin-1-one derivatives; each B substituent is represented in the following table II.

M refers to the central core of the divalent 3,4-dihydro-2H-pyrrolo[1,2-a]pyrazin-1-one moiety being substituted in position 7 by groups A and at the carbonyl group by groups B, substantially as follows:

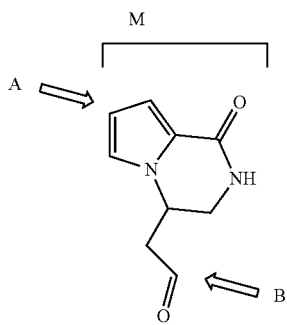

(I)

For ease of reference, each A and B group, in tables I and II respectively, have been identified with the proper chemical formula and an indication of the attachment point with the molecule core M.

To illustrate, compound A3-M-B5 of table III (entry 13) represents the core M, 3,4-dihydro-2H-pyrrolo[1,2-a]pyrazin-1-one, being substituted at 7-position by the group A3 and by the group B5 through the carbonyl group; likewise, compound A24-M-B8 of table III (entry 137) represents the core M, 3,4-dihydro-2H-pyrrolo[1,2-a]pyrazin-1-one, being substituted at 7-position by the group A24 and by the group B8 through the carbonyl group, as follows:

A127-M-B22

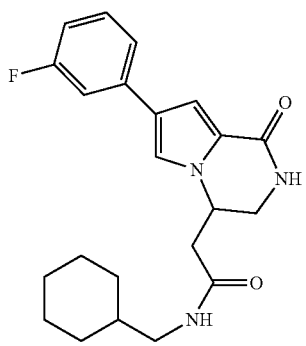

-continued

A150-M-B40

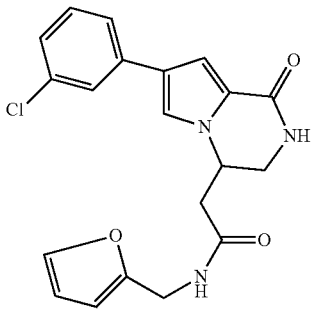

TABLE I

| A groups | |
|---|---|
| Fragment | CODE |
| ⌬—≡—M | A1 |
| MeO—C6H4—M | A2 |
| MeO—C6H4—C(O)—NH—M | A3 |
| Me—C6H4—SO2—NH—M | A4 |
| M—NH—C(O)—NH—C6H5 | A5 |
| M—CH=CH—C(O)—O—Et | A6 |
| F—C6H4—C(O)—NH—M | A7 |

TABLE I-continued

A groups

| Fragment | CODE |
|---|---|
| 4-fluorophenyl sulfonamide-M | A8 |
| 4-fluorophenyl-NH-C(O)-NH-M | A9 |
| HOOC-CH=CH-M (cis) | A10 |
| (CH₃)₂N-CH₂-C(O)-NH-M | A11 |
| cyclopropyl-C(O)-NH-M | A12 |
| M-NH-C(O)-CH₂-CN | A13 |
| 2-oxo-2H-pyran-4-carboxamide-M | A14 |
| 5-methylthiophene-2-carboxamide-M | A15 |
| M-NH-C(O)-NH-cyclohexyl | A16 |
| 4-methoxyphenyl-NH-C(O)-NH-M | A17 |
| piperidin-1-yl-C(O)-CH=CH-M (trans) | A18 |
| M-CH=CH-C(O)-O-butyl | A19 |
| 4-chlorophenyl-M | A20 |
| 4-nitrophenyl-M | A21 |
| 4-methoxyphenyl-CH=CH-M (cis) | A22 |
| pyridin-4-yl-M | A24 |
| cyclopentyl-C≡C-M | A25 |
| 4-methoxyphenyl-C≡C-M | A26 |
| 4-chlorophenyl-C≡C-M | A27 |
| 3-(2,5-dimethylpyrrol-1-yl)phenyl-C≡C-M | A28 |

TABLE I-continued

A groups

| Fragment | CODE |
| --- | --- |
| (propenyl-M) | A29 |
| (cyclohexyl-CH=CH-M) | A30 |
| (M-CH=CH-phenyl) | A31 |
| (4-Cl-phenyl-CH=CH-M) | A32 |
| (3-thienyl-M) | A33 |
| (phenyl-M) | A34 |
| (4-dimethylamino-phenyl-M) | A35 |
| (3,4-dimethyl-benzamide-M) | A36 |
| (thiophene-2-carboxamide-M) | A37 |
| (4-methyl-benzamide-M) | A38 |
| (3-cyano-benzamide-M) | A39 |

TABLE I-continued

A groups

| Fragment | CODE |
| --- | --- |
| (thiophene-3-carboxamide-M) | A40 |
| (3,4-difluoro-benzamide-M) | A41 |
| (2,4-dimethyl-benzamide-M) | A42 |
| (2-fluoro-5-chloro-benzamide-M) | A43 |
| (cyclobutane-carboxamide-M) | A44 |
| (3,3-dimethyl-butanamide-M) | A45 |
| (4-cyano-benzamide-M) | A46 |
| (2-methyl-benzamide-M) | A47 |
| (3-methyl-benzamide-M) | A48 |
| (cyclohexane-carboxamide-M) | A49 |

TABLE I-continued
| A groups | |
|---|---|
| Fragment | CODE |
| 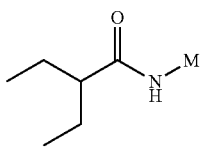 | A50 |
| 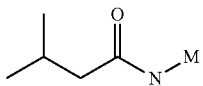 | A51 |
| 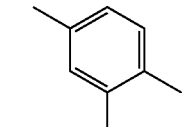 | A52 |
| 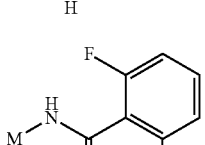 | A53 |
| 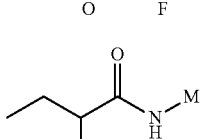 | A54 |
| 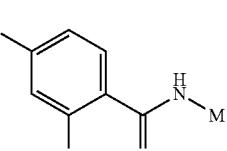 | A55 |
| 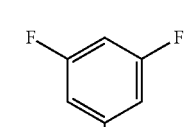 | A56 |
| 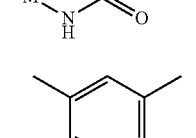 | A57 |
| 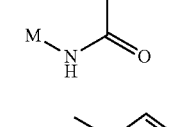 | A58 |
| 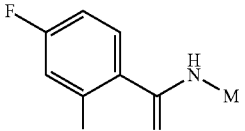 | A59 |
| 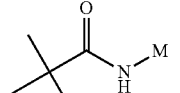 | A60 |
| 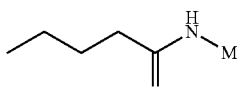 | A61 |
| 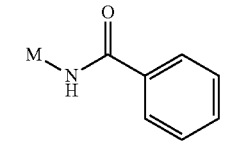 | A62 |
| 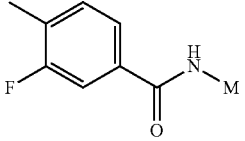 | A63 |
| 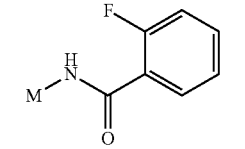 | A64 |
| 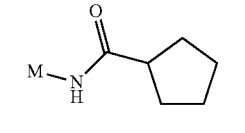 | A65 |
| 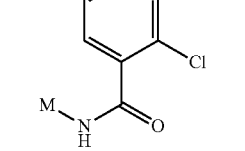 | A66 |
| 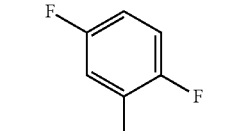 | A67 |
| 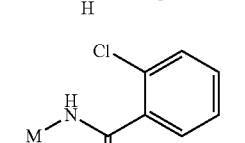 | A68 |

TABLE I-continued

A groups

| Fragment | CODE |
|---|---|
| (butyramide fragment) | A69 |
| (3-fluorobenzamide fragment) | A70 |
| (isobutyramide fragment) | A71 |
| (1-ethyl-1H-pyrazole-3-carboxamide fragment) | A72 |
| (N-(2-fluorophenyl)urea fragment) | A73 |
| (benzenesulfonamide fragment) | A74 |
| (furan-2-carboxamide fragment) | A75 |
| (nicotinamide fragment) | A76 |
| (1-ethyl-1H-pyrazole-5-carboxamide fragment) | A77 |
| (N-(2-methoxyphenyl)urea fragment) | A78 |
| (N-(5-chloro-2-methylphenyl)urea fragment) | A79 |
| (N-(3-chloro-4-fluorophenyl)urea fragment) | A80 |
| (N-(3-chloro-2-methylphenyl)urea fragment) | A81 |
| (N-(2-ethylphenyl)urea fragment) | A82 |
| (N-(2,4-dimethylphenyl)urea fragment) | A83 |
| (N-benzylurea fragment) | A84 |
| (N-(3-fluoro-4-methylphenyl)urea fragment) | A85 |
| (N-cyclopentylurea fragment) | A86 |
| (N-(4-methylbenzyl)urea fragment) | A87 |

TABLE I-continued
A groups
| Fragment | CODE |
|---|---|
| 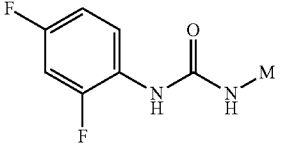 | A88 |
| 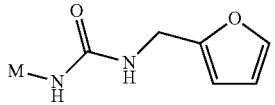 | A89 |
| 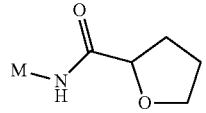 | A90 |
| 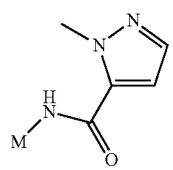 | A91 |
| 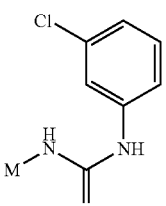 | A92 |
| 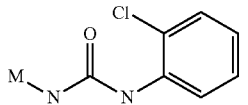 | A93 |
| 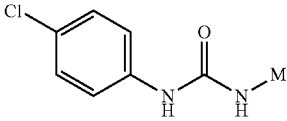 | A94 |
| 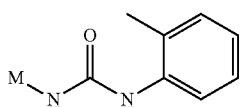 | A95 |
| 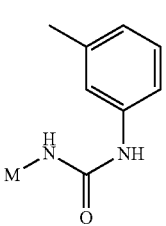 | A96 |
| 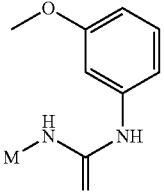 | A97 |
| 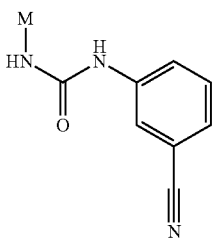 | A98 |
| 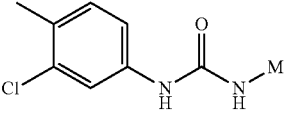 | A99 |
| 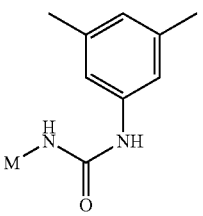 | A100 |
| 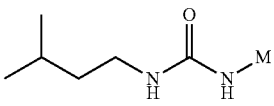 | A101 |
| 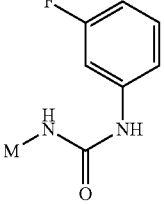 | A102 |
| 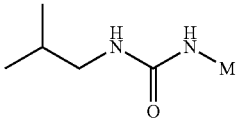 | A103 |
| 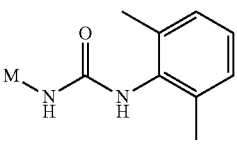 | A104 |

TABLE I-continued
| A groups | |
|---|---|
| Fragment | CODE |
| 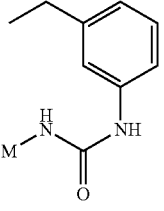 | A105 |
| 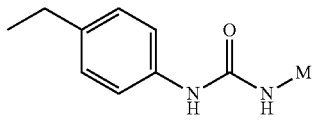 | A106 |
| 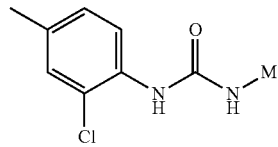 | A107 |
| 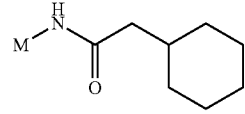 | A108 |
| 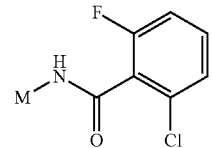 | A109 |
| 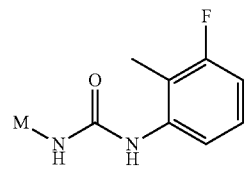 | A110 |
| 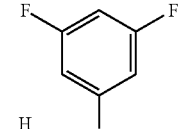 | A111 |
| 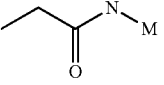 | A112 |
| 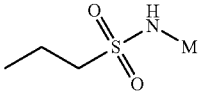 | A113 |
| 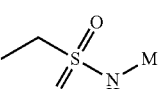 | A114 |
| 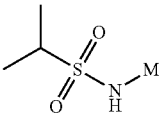 | A115 |
| 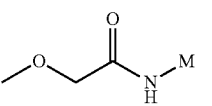 | A116 |
| 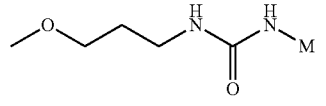 | A117 |
| 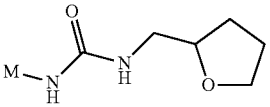 | A118 |
| 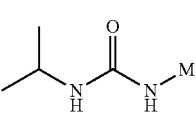 | A119 |
| 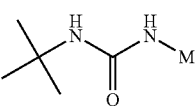 | A120 |
| 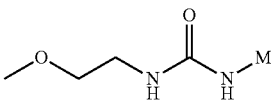 | A121 |
| 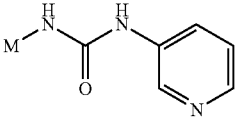 | A122 |
| 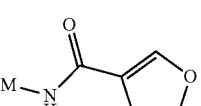 | A123 |
| 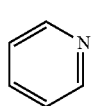 | A124 |
| 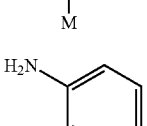 | A125 |
| 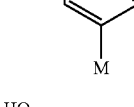 | A126 |

TABLE I-continued

A groups

| Fragment | CODE |
|---|---|
| 3-fluorophenyl-M | A127 |
| 2-fluorophenyl-M | A128 |
| 4-fluorophenyl-M | A129 |
| 5-cyanopyridin-3-yl-M | A130 |
| 3-acetylphenyl-M | A131 |
| benzo[d][1,3]dioxol-5-yl-M | A132 |
| 3-(trifluoromethyl)phenyl-M | A133 |
| 3-(trifluoromethoxy)phenyl-M | A134 |
| 4-(trifluoromethoxy)phenyl-M | A135 |
| 4-aminophenyl-M | A136 |
| 3-methylphenyl-M | A137 |
| 3-methoxyphenyl-M | A138 |
| 3,4-difluorophenyl-M | A139 |
| 3-(methylthio)phenyl-M | A140 |
| methyl 4-benzoate-M | A141 |
| methyl 3-benzoate-M | A142 |
| 4-(trifluoromethyl)phenyl-M | A143 |
| 1H-pyrazol-4-yl-M | A144 |
| 5-bromo-1H-indol-2-yl-M | A145 |

TABLE I-continued

A groups

| Fragment | CODE |
|---|---|
| 2-methoxy-4-fluorophenyl (M on ring) | A146 |
| 4-methylphenyl (M) | A147 |
| 2-methoxy-5-fluorophenyl (M) | A148 |
| 3,5-difluorophenyl (M) | A149 |
| 3-chlorophenyl (M) | A150 |
| 2,4-difluorophenyl (M) | A151 |
| cis-pent-2-enyl (M) | A152 |
| 1-phenylvinyl (M) | A153 |
| propenyl (M) | A154 |
| 2-pyridyl-ethynyl (M) | A155 |
| quinolin-8-yl (M) | A156 |

TABLE I-continued

A groups

| Fragment | CODE |
|---|---|
| 2-fluoropyridin-4-yl (M) | A157 |
| 2,5-difluorophenyl (M) | A158 |

TABLE II

B groups

| Fragment | CODE |
|---|---|
| ethoxy (M) | B1 |
| hydroxy (M) | B2 |
| butoxy (M) | B3 |
| 2,6-dimethylmorpholin-4-yl (M) | B4 |
| piperidin-1-yl (M) | B5 |
| N-(2-phenylethyl)amino (M) | B6 |
| N-(2-methoxyethyl)amino (M) | B7 |
| N-(3-dimethylaminopropyl)amino (M) | B8 |
| N-(2,2-dimethylpropyl)amino (M) | B9 |
| (2R,6S)-2,6-dimethylmorpholin-4-yl (M) | B10 |

TABLE II-continued

B groups

| Fragment | CODE |
|---|---|
| (2,6-dimethylmorpholin-4-yl)-M | B11 |
| tetrahydrofuran-2-ylmethyl-NH-M | B12 |
| isopropyl-NH-M | B13 |
| benzyl-NH-M | B14 |
| sec-butyl-NH-M | B15 |
| (1-phenylethyl)-NH-M | B16 |
| ethyl-NH-M | B17 |
| (4-methylcyclohexyl)-NH-M | B18 |
| cyclopropyl-NH-M | B19 |
| (2-methylbenzyl)-NH-M | B20 |
| (4-methylbenzyl)-NH-M | B21 |
| cyclohexylmethyl-NH-M | B22 |
| isobutyl-NH-M | B23 |
| cyclohexyl-NH-M | B24 |
| propyl-NH-M | B25 |
| cyclopentyl-NH-M | B26 |
| allyl-NH-M | B27 |
| (tetrahydropyran-4-yl)-NH-M | B28 |
| (pyridin-3-ylmethyl)-NH-M | B29 |
| (3-fluorobenzyl)-NH-M | B30 |
| dimethylamino-M | B31 |
| isopentyl-NH-M | B32 |
| 4-methyl-1-(pyridin-2-yl)piperazine-M | B33 |
| thiomorpholin-4-yl-M | B34 |
| methyl-NH-M | B35 |
| (2-methylphenyl)-NH-M | B36 |

TABLE II-continued

| B groups | |
|---|---|
| Fragment | CODE |
| (3-methylphenyl)amino- | B37 |
| morpholinoethylamino- | B38 |
| (pyridin-4-ylmethyl)amino- | B39 |
| (furan-2-ylmethyl)amino- | B40 |
| 4-carbamoylpiperidin-1-yl | B41 |
| (3-methoxypropyl)amino- | B42 |
| tert-butylamino- | B43 |
| (2-(pyrrolidin-1-yl)ethyl)amino- | B44 |
| azepan-1-yl | B45 |
| N-methyl-N-propylamino- | B46 |
| ((5-methylfuran-2-yl)methyl)amino- | B47 |
| (cyclopropylmethyl)amino- | B48 |
| 4-allylpiperazin-1-yl | B49 |
| pyrrolidin-1-yl | B50 |
| morpholino | B51 |
| phenylamino- | B52 |
| (2-(1-methylpiperidin-4-yl)ethyl)amino- | B53 |
| ((1,3-dimethyl-1H-pyrazol-4-yl)methyl)(methyl)amino- | B54 |
| (2-(1,3,5-trimethyl-1H-pyrazol-4-yl)ethyl)(methyl)amino- | B55 |
| 4-methylpiperazin-1-yl | B56 |
| 4-(1-methylpiperidin-4-yl)piperazin-1-yl | B57 |
| 4-(methylsulfonyl)piperazin-1-yl | B58 |
| 4-methyl-1,4-diazepan-1-yl | B59 |

TABLE II-continued

B groups

| Fragment | CODE |
|---|---|
| (1-methyl-1,4-diazepane attached via N) | B60 |
| (N,N-dimethylaminoethyl-NH-) | B61 |
| (NH-CH(cyclohexyl)-CH2OH) | B62 |
| (NH-CH(Ph)-CH2OH, stereo) | B63 |
| (4-methyl-2-phenylpiperazine attached via N) | B64 |
| (NH-CH(CH2Ph)-CH2OH) | B65 |
| (NH-CH(Ph)-CH2NH2) | |

Preparation of 2,2,2-trichloro-1-(4-nitro-1H-pyrrol-2-yl)ethanone (III)

Nitric acid (90%, 2 mL) was added dropwise over a period of 30 minutes to a solution of 2,2,2-trichloro-1-(1H-pyrrol-2-yl)ethanone (II) (1 g, 4.7 mmol) in acetic anhydride (10 ml), cooled to −40° C. The reaction mixture was allowed to warm up slowly to room temperature and stirred for 6 h. The solvent was evaporated under vacuum and the residue purified by flash chromatography (hexane-EtOAc 9:1) to obtain the compound of formula (III) as a yellow solid (670 mg, 55% yield). 2,2,2-Trichloro-1-(5-nitro-1H-pyrrol-2-yl)ethanone was also obtained as side product (349 mg, 29% yield).

LCMS (HPLC Method 2): m/z 256 [M−H]− @ r.t. 5.44 min. $^1$H NMR (400 MHz, DMSO-d$_6$) δ=13.65 (br. s., 1 H), 8.39 (dd, J=1.4, 3.6 Hz, 1 H), 7.73 (t, J=1.8 Hz, 1 H)

Preparation of ethyl(7-nitro-1-oxo-1,2,3,4-tetrahydropyrrolo[1,2-a]pyrazin-4-yl)acetate (V, where R1=OCH$_2$CH$_3$)

Ethyl (2E)-4-aminobut-2-enoate trifluoroacetate (IV) (5.99 g, 24.6 mmol) was added to a solution of 2,2,2-trichloro-1-(4-nitro-1H-pyrrol-2-yl)ethanone (III) (3.17 g, 12.3 mmol) and DIPEA (12.6 mL, 73.8 mmol) in dry CH$_2$Cl$_2$ (120 mL) and the reaction mixture was stirred at room temperature overnight. The solvent was evaporated under vacuum and the residue purified by flash chromatography (hexane-EtOAc 2:3), to obtain the compound of formula (V) (where R1=OCH$_2$CH$_3$) as a light-yellow solid (3.19 g, 97% yield).

LCMS (HPLC Method 2): m/z 268 [M+H]+ @ r.t. 3.48 min. $^1$H NMR (400 MHz, DMSO-d$_6$)) δ=8.13 (br. s., 1 H), 8.12 (d, J=1.7 Hz, 1 H), 7.14 (d, J=1.8 Hz, 1 H), 4.74-4.84 (m, 1 H), 4.11 (q, J=7.2 Hz, 2 H), 3.75 (ddd, J=1.8, 4.2, 13.4 Hz, 1 H), 3.44 (dt, J=4.2, 13.4 Hz, 1 H), 2.96 (dd, J=1.6, 6.8 Hz, 2 H), 1.19 (t, J=7.1 Hz, 3 H)

Example 1

Preparation of ethyl(7-amino-1-oxo-1,2,3,4-tetrahydropyrrolo[1,2-a]pyrazin-4-yl)acetate hydrochloride (I)

To a solution of ethyl(7-nitro-1-oxo-1,2,3,4-tetrahydropyrrolo[1,2-a]pyrazin-4-yl)acetate (V, where R1=OCH$_2$CH$_3$) (0.55 g, 2.1 mmol) in ethanol 100% (20 mL) was added hydrochloric acid (4 M solution in 1,4-dioxane, 0.52 mL, 2.1 mmol). The reaction mixture was stirred at room temperature in the presence of Pd—C (10%) (0.11 g), under hydrogen atmosphere (50 psi). After 7 h the solid was filtered through celite (washed with ethanol) and the solvent evaporated under vacuum, to obtain compound ethyl(7-amino-1-oxo-1,2,3,4-tetrahydropyrrolo[1,2-a]pyrazin-4-yl)acetate hydrochloride (I) as a light-brown solid (0.56 g, 98% yield), used without further purification in the next steps. Very hygroscopic product. To be stored for a short time and under inert gas atmosphere.

LCMS (HPLC Method 2): m/z 238 [M−H]− @ r.t. 1.89 min (broad peak). $^1$H NMR (400 MHz, DMSO-d$_6$) δ=9.75 (br. s., 2 H), 7.84 (br. s., 1 H), 7.10 (d, J=1.8 Hz, 1 H), 6.62 (d, J=1.8 Hz, 1 H), 4.64-4.75 (m, 1 H), 4.05-4.15 (m, 2 H), 3.64-3.75 (m, 1 H), 3.34-3.44 (m, 1 H), 2.83-2.94 (m, 1 H), 2.73-2.82 (m, 1 H), 1.20 (t, J=7.1 Hz, 3 H).

Example 2

Preparation A7-M-B1 (Entry 34, Table III)

A solution of 4-fluorobenzoic acid (0.29 g, 2.1 mmol), 1-ethyl-3-(3'-dimethylaminopropyl)carbodiimide (EDC) (0.4 g, 2.1 mmol), 3,4-dihydro-3-hydroxy-4-oxo-1,2,3-benzotriazine (DHBT) (0.34 g, 2.1 mmol) and N,N-diisopropylethylamine (DIPEA) (0.75 mL, 4.2 mmol) in dry acetonitrile (10 mL) was stirred at room temperature for 10 min, before adding ethyl(7-amino-1-oxo-1,2,3,4-tetrahydropyrrolo[1,2-a]pyrazin-4-yl)acetate hydrochloride (I) (0.52 g, 1.9 mmol). The reaction mixture was stirred overnight at the same temperature. The solvent was evaporated under vacuum and the residue purified by flash chromatography (EtOAc+5%

MeOH), to obtain compound A7-M-B1 (entry 34, table III) as an off-white solid (0.49 g, 71% yield).

LCMS (HPLC Method 2): m/z 361 [M+H]$^+$ @ r.t. 3.99 min. $^1$H NMR (500 MHz, DMSO-d$_6$) δ=10.37 (s, 1 H), 7.97-8.02 (m, 2 H), 7.66 (br. s., 1 H), 7.44 (d, J=1.6 Hz, 1H), 7.31-7.38 (m, 2 H), 6.73 (d, J=1.6 Hz, 1 H), 4.63 (ddd, J=3.2, 3.3, 6.8 Hz, 1 H), 4.09 (q, J=7.0 Hz, 2 H), 3.66-3.72 (m, 1 H), 3.34-3.39 (m, 1 H), 2.81-2.89 (m, 1 H), 2.68-2.77 (m, 1 H), 1.19 (t, J=7.1 Hz, 3 H).

Example 3

Preparation A9-M-B1 (Entry 54, Table III)

N,N-diisopropylethylamine (DIPEA)(0.19 mL, 1.1 mmol) was added to a solution of 1-fluoro-4-isocyanatobenzene (0.15 mL, 1.2 mmol) and (a suspension of) ethyl(7-amino-1-oxo-1,2,3,4-tetrahydropyrrolo[1,2-a]pyrazin-4-yl)acetate hydrochloride (I) (0.30 g, 1.1 mmol) in dry dichloromethane (10 mL). The reaction mixture was stirred at room temperature overnight, the solvent was evaporated under vacuum and the residue purified by flash chromatography (EtOAc+5% MeOH), to obtain compound A9-M-B1 (entry 54, table III) as an off-white solid (0.33 g, 80% yield).

LCMS (HPLC Method 2): m/z 376 [M+H]$^+$ @ r.t. 4.04 min. $^1$H NMR (500 MHz, DMSO-d$_6$) δ=8.56 (s, 1 H), 8.37 (s, 1 H), 7.59 (d, J=2.6 Hz, 1 H), 7.38-7.46 (m, 2 H), 7.10-7.11 (m, 1 H), 7.05-7.12 (m, 2 H), 6.48 (d, J=1.8 Hz, 1 H), 4.53-4.59 (m, 1 H), 4.06-4.12 (m, 2 H), 3.64-3.70 (m, 1 H), 3.29-3.36 (m, 1 H), 2.79-2.85 (m, 1 H), 2.69-2.74 (m, 1 H), 1.19 (t, J=7.1 Hz, 3 H).

Example 4

Preparation A8-M-B1 (Entry 52, Table III)

N-methylmorpholine (0.28 mL, 2.6 mmol) was added to a solution of 4-fluorobenzenesulfonyl chloride (0.25 g, 1.3 mmol) and (a suspension of) ethyl(7-amino-1-oxo-1,2,3,4-tetrahydropyrrolo[1,2-a]pyrazin-4-yl)acetate hydrochloride (I) (0.32 g, 1.2 mmol) in dry dichloromethane (10 mL) and the reaction mixture was stirred at room temperature overnight. The solvent was evaporated under vacuum and the residue purified by flash chromatography (EtOAc), to obtain compound A8-M-B1 (entry 52, table III) as an off-white solid (0.30 g, 64% yield).

LCMS (HPLC Method 2): m/z 397 [M+H]$^+$ @ r.t. 3.96 min. $^1$H NMR (500 MHz, DMSO-d$_6$) δ=9.75 (s, 1 H), 7.70-7.77 (m, 2 H), 7.65 (d, J=2.9 Hz, 1 H), 7.35-7.42 (m, 2 H), 6.67 (d, J=1.8 Hz, 1 H), 6.20 (d, J=1.8 Hz, 1 H), 4.50-4.56 (m, 1 H), 3.99-4.10 (m, J=3.5, 3.7, 7.1, 7.1, 10.6 Hz, 2 H), 3.58-3.64 (m, 1 H), 3.26-3.32 (m, 1 H), 2.78 (dd, J=6.4, 16.0 Hz, 1 H), 2.58-2.68 (m, 1 H), 1.16 (t, J=7.1 Hz, 3 H).

Preparation of 2,2,2-trichloro-1-(4-iodo-1H-pyrrol-2-yl)ethanone (IX)

Iodine (1.2 g, 4.7 mmol) was added portion wise to a solution of 2,2,2-trichloro-1-(1H-pyrrol-2-yl)ethanone (1 g, 4.7 mmol) and silver trifluoroacetate (1.1 g, 5 mmol) in dry dichloromethane (24 mL), cooled to 0° C. The reaction mixture was allowed to warm up slowly to 18° C. (water bath) and stirred at the same temperature for 5 h. The solid was filtered, the organic phase washed with Na$_2$S$_2$O$_5$ (5% aq. solution) until decoloration occurs and finally washed with H$_2$O (1×20 mL). The organic phase was dried over Na$_2$SO$_4$ and filtered through a plough of SiO$_2$ (hexane-EtOAc 4:1), to obtain compound 2,2,2-trichloro-1-(4-iodo-1H-pyrrol-2-yl)ethanone (IX) as an off-white solid (1.49 g, 94% yield).

LCMS (HPLC Method 2): m/z 336 [M–H]$^-$ @ r.t. 6.3 min. $^1$H NMR (400 MHz, DMSO-d$_6$) δ=12.76 (br. s., 1 H), 7.52 (dd, J=1.3, 3.3 Hz, 1 H), 7.39 (dd, J=1.3, 2.6 Hz, 1 H).

Preparation of ethyl (2E)-4-{[(4-iodo-1H-pyrrol-2-yl)carbonyl]amino}but-2-enoate (X, where R1=OCH$_2$CH$_3$)

Ethyl (2E)-4-aminobut-2-enoate trifluoroacetate (IV) (0.97 g, 4 mmol) was added to a solution of 2,2,2-trichloro-1-(4-iodo-1H-pyrrol-2-yl)ethanone (IX) (0.68 g, 2 mmol) and N,N-diisopropylethylamine (DIPEA) (2.7 mL, 16 mmol) in dichloromethane (20 mL) and the reaction mixture was stirred at room temperature overnight. The solvent was evaporated under vacuum and the residue purified by flash chromatography (SiO$_2$, hexane-EtOAc 1:1) to obtain compound ethyl (2E)-4-{[(4-iodo-1H-pyrrol-2-yl)carbonyl]amino}but-2-enoate (X, where R1=OCH$_2$CH$_3$) as an off-white solid (0.48 g, 68% yield).

LCMS (HPLC Method 2): m/z 349 [M+H]$^+$ @αr.t. 4.7 min. $^1$H NMR (400 MHz, DMSO-d$_6$) δ=11.82 (br. s., 1 H), 8.39 (t, J=5.8 Hz, 1 H), 7.01 (dd, J=1.5, 2.9 Hz, 1 H), 6.96 (dd, J=1.5, 2.5 Hz, 1 H), 6.90 (dt, J=4.7, 15.7 Hz, 1 H), 5.87 (dt, J=1.8, 15.7 Hz, 1H), 4.12 (q, J=7.1 Hz, 2 H), 3.99-4.06 (m, 2 H), 1.21 (t, J=7.1 Hz, 3 H).

Preparation of ethyl (7-iodo-1-oxo-1,2,3,4-tetrahydropyrrolo[1,2-a]pyrazin-4-yl)acetate (XI, where R1=OCH$_2$CH$_3$)

Diaza(1,3)bicyclo[5.4.0]undecane (DBU) (0.04 mL, 0.3 mmol) was added to a solution of ethyl (2E)-4-{[(4-iodo-1H-pyrrol-2-yl)carbonyl]amino}but-2-enoate (X, where R1=OCH$_2$CH$_3$) (0.45 g, 1.3 mmol) in acetonitrile (8 mL) and the reaction mixture was stirred at room temperature for 30 min. The solvent was evaporated under vacuum and the residue purified by flash chromatography (SiO$_2$, hexane-EtOAc 1:1) to obtain compound ethyl (7-iodo-1-oxo-1,2,3,4-tetrahydropyrrolo[1,2-a]pyrazin-4-yl)acetate (XII, where R1=OCH$_2$CH$_3$) as an off-white solid (0.35 g, 79% yield).

LCMS (HPLC Method 2): m/z 349 [M+H]$^+$ @ r.t. 4.15 min. $^1$H NMR (400 MHz, DMSO-d$_6$) δ=7.72 (br. s., 1 H), 7.13 (d, J=1.7 Hz, 1 H), 6.72 (d, J=1.6 Hz, 1 H), 4.59-4.71 (m, 1 H), 4.10 (qd, J=1.8, 7.1 Hz, 2 H), 3.66 (ddd, J=1.7, 4.2, 13.1 Hz, 1 H), 3.30-3.38 (m, 1 H), 2.83 (d, J=6.7 Hz, 2 H), 1.19 (t, J=7.1 Hz, 3 H).

Example 5

Preparation A21-M-B1 (entry 127, table III)

A mixture of ethyl (7-iodo-1-oxo-1,2,3,4-tetrahydropyrrolo[1,2-a]pyrazin-4-yl)acetate (XI, where R1=OCH$_2$CH$_3$) (50 mg, 0.14 mmol), 1,1'-bis(diphenylphosphino)ferrocene-palladium(II)dichloride, complex with dichloromethane (1:1) (12 mg, 0.015 mmol) and 4-nitrophenylboronic acid (47 mg, 0.28 mmol) in dimethoxyethane (DME) (1 mL) was degassed before addition of sodium carbonate (45 mg, 0.42 mmol in 0.5 mL of H$_2$O) and the reaction mixture was stirred at 80° C. for 3 h, under an argon atmosphere. The reaction mixture was filtered through silica (washed with EtOAc) and the solvent evaporated under vacuum. The residue was purified by flash chromatography (EtOAc-hex), to obtain compound A21-M-B1 (entry 127, table III) (29 mg, 60% yield).

LCMS (HPLC Method 2): m/z 345 [M+H]$^+$ @ r.t. 4.61 min. $^1$H NMR (400 MHz, DMSO-d$_6$) δ=8.19 (d, J=9.0 Hz, 2 H), 7.87 (d, J=9.0 Hz, 2 H), 7.80 (d, J=1.7 Hz, 1 H), 7.76 (d, J=1.8 Hz, 1 H), 7.24 (d, J=1.8 Hz, 1 H), 4.71 (ddd, J=3.4, 3.6, 6.6 Hz, 1 H), 4.04-4.17 (m, 2 H), 3.74 (ddd, J=1.8, 4.1, 13.3 Hz, 1 H), 3.35-3.45 (m, 1 H), 2.88-2.99 (m, 2H), 1.15-1.22 (m, 3 H).

Example 6

Preparation A22-M-B1 (entry 128, table III)

A mixture of ethyl (7-iodo-1-oxo-1,2,3,4-tetrahydropyrrolo[1,2-a]pyrazin-4-yl)acetate (XI, where R1=OCH$_2$CH$_3$) (50 mg, 0.14 mmol), 1,1'-bis(diphenylphosphino)ferrocene-palladium(II)dichloride, complex with dichloromethane (1:1) (12 mg, 0.015 mmol) and trans-2-(4-methoxyphenyl)vinylboronic acid (50 mg, 0.28 mmol) in dimethoxyethane (DME) (1 mL) was degassed before addition of sodium carbonate (45 mg, 0.42 mmol in 0.5 mL of H$_2$O) and the reaction mixture was stirred at 80° C. for 6 h, under an argon atmosphere. The reaction mixture was filtered through silica (washed with EtOAc) and the solvent evaporated under vacuum. The residue was purified by flash chromatography (EtOAc-Hex), to obtain compound A22-M-B1 (entry 128, table III) (31 mg, 62% yield).

LCMS (HPLC Method 2): m/z 356 [M+H]$^+$ @ r.t. 5.12 min. $^1$H NMR (400 MHz, DMSO-d$_6$) δ=7.66 (d, J=3.2 Hz, 1 H), 7.38-7.45 (m, 2 H), 7.13 (d, J=1.6 Hz, 1 H), 6.87-6.93 (m, 4 H), 6.79-6.85 (m, 1 H), 4.58-4.66 (m, 1 H), 4.12 (q, J=7.1 Hz, 2 H), 3.76 (s, 3 H), 3.65-3.73 (m, 1 H), 3.32-3.39 (m, 1 H), 2.76-2.91 (m, 2 H), 1.20 (t, J=7.1 Hz, 3H).

Example 7

Preparation A27-M-B1 (Entry 151, Table III)

A mixture of ethyl (7-iodo-1-oxo-1,2,3,4-tetrahydropyrrolo[1,2-a]pyrazin-4-yl)acetate (XI, where R1=OCH$_2$CH$_3$) (500 mg, 1.44 mmol), bis(triphenylphosphine)palladium(II)dichloride (50 mg, 0.07 mmol), copper(I) iodide (41 mg, 0.22 mmol), 1-chloro-4-ethynylbenzene (0.29 g, 2.15 mmol) and triethylamine (0.58 mL, 5.74 mmol) in dry dimethylformamide (14 mL) was degassed and the reaction mixture was stirred at room temperature overnight, under an argon atmosphere. The solvent was evaporated under vacuum and the residue purified by flash chromatography (EtOAc-CH$_2$Cl$_2$), to obtain compound A27-M-B1 (entry 151, table III) (0.51 g, 99% yield).

LCMS (HPLC Method 2): m/z 358 [M+H]$^+$ @ r.t. 6.48 min. $^1$H NMR (400 MHz, DMSO-d$_6$) δ=7.82 (br. s., 1 H), 7.42-7.50 (m, 4 H), 7.37 (d, J=1.6 Hz, 1 H), 6.78 (d, J=1.6 Hz, 1 H), 4.63-4.70 (m, 1 H), 4.11 (q, J=7.1 Hz, 2 H), 3.65-3.74 (m, 1 H), 3.33-3.41 (m, 1 H), 2.81-2.91 (m, 2 H), 1.19 (t, J=7.1 Hz, 3 H).

Preparation of ethyl (2E)-4-(diformylamino)but-2-enoate (XV)

A solution of ethyl-4-bromo-crotonate (1 g, 5.18 mmol), diformylimide sodium salt (0.59 g, 6.22 mmol) and sodium iodide (0.78 g, 5.18 mmol) in dry acetonitrile (25 mL) was stirred under reflux overnight. The solvent was evaporated under vacuum and the residue partitioned between dichloromethane and water (1:1, 40 mL). The aqueous phase was back-extracted with dichloromethane (3×15 mL) and the combined organic layers were dried over Na$_2$SO$_4$. The solvent was evaporated under vacuum and the residue purified by flash chromatography (hexane-EtOAc 6:4) to obtain compound ethyl (2E)-4-(diformylamino)but-2-enoate (XV) as a light-brown solid (0.92 g, 96% yield). In alternative, Et$_2$O was added to the deep brown oil residue to obtain the product as a crystalline solid.

LCMS (HPLC Method 2): m/z 186 [M–H]$^-$ @ r.t. 3.36 min. $^1$H NMR (400 MHz, DMSO-d$_6$) δ=9.01 (s, 2 H), 6.78 (dt, J=4.6, 15.9 Hz, 1 H), 5.88 (dt, J=2.0, 15.8 Hz, 1 H), 4.26 (dd, J=2.0, 4.5 Hz, 2 H), 4.12 (q, J=7.1 Hz, 2 H), 1.21 (t, J=7.1 Hz, 3 H)

Preparation of ethyl (2E)-4-aminobut-2-enoate trifluoroacetate (IV)

A solution of ethyl (2E)-4-(diformylamino)but-2-enoate (XV) (0.89 mg, 4.8 mmol) in a mixture trifluoroacetic acid-ethanol (absolute) (2:1, 10 mL) was stirred under reflux overnight (the reaction was followed by LC-MS and stopped when complete conversion was achieved). The solvent was evaporated under vacuum to obtain compound ethyl (2E)-4-aminobut-2-enoate trifluoroacetate (IV) as brown oil (undetermined yield), which was used without further purification in the next step.

Example 8

Preparation A2-M-B2 (Entry 8, Table III)

To a solution of derivative A2-M-B1 (entry 7, table III) (24 mg, 0.07 mmol) in a mixture tetrahydrofuran-water (1:1, 2 mL) was added lithium hydroxide (6 mg, 0.04 mmol) and the reaction mixture was stirred at room temperature for 3 h. The organic phase was washed with dichloromethane (2×5 mL). The aqueous phase was acidified with hydrochloric acid (1 M) until pH<1 and extracted with EtOAc (4×10 mL). The combined organic layers were dried over Na$_2$SO$_4$ and the solvent was evaporated under vacuum to obtain compound A2-M-B2 (entry 8, table III) as an off-white solid (21 mg, 100% yield).

LCMS (HPLC Method 2): m/z 302 [M+H]$^+$ @ r.t. 3.06 min. $^1$H NMR (400 MHz, DMSO-d$_6$) δ=7.64 (br. s., 1 H), 7.45-7.50 (m, 2 H), 7.37 (d, J=1.8 Hz, 1 H), 6.96 (d, J=1.8 Hz, 1 H), 6.88-6.94 (m, 2 H), 4.57-4.63 (m, 1 H), 3.76 (s, 3 H), 3.67-3.73 (m, 1 H), 3.37-3.42 (m, 1 H), 2.74-2.86 (m, 2 H).

Example 9

Preparation A5-M-B5 (Entry 29, Table III)

To a solution of derivative A5-M-B2 (entry 23, table III) (45 mg, 0.14 mmol) in a dry mixture acetonitrile-dimethylformamide (3:1, 4 mL), 1-ethyl-3-(3'-dimethylaminopropyl)carbodiimide (EDC) (32 mg, 0.17 mmol), 3,4-dihydro-3-hydroxy-4-oxo-1,2,3-benzotriazine (DHBT) (28 mg, 0.17 mmol) and N,N-diisopropylethylamine (DIPEA) (0.024 mL, 0.14 mmol) were added and the reaction mixture was stirred at room temperature for 10 min before adding piperidine (0.028 mL, 0.28 mmol). The reaction mixture was stirred at the same temperature overnight. The reaction mixture was then diluted with water and extracted with EtOAc (4×5 mL). The combined organic layers were dried over Na$_2$SO$_4$, the solvent evaporated under vacuum and the residue purified by prep-HPLC to obtain compound A5-M-B5 (Entry 29, Table III) as a white solid (13 mg, 23% yield).

LCMS (HPLC Method 2): m/z 397 [M+H]$^+$ @ r.t. 3.74 min. $^1$H NMR (400 MHz, DMSO-d$_6$) δ=8.50 (s, 1 H), 8.34 (s, 1 H), 7.51 (d, J=2.9 Hz, 1 H), 7.42 (d, J=7.6 Hz, 2H), 7.24 (t, J=8.0 Hz, 2 H), 7.12 (d, J=1.7 Hz, 1 H), 6.92 (t, J=7.3 Hz, 1 H), 6.48 (d, J=1.7 Hz, 1 H), 4.58 (tt, J=3.9, 6.7 Hz, 1 H), 3.67 (ddd, J=1.1, 4.3, 12.9 Hz, 1 H), 2.79 (dd, J=5.7, 16.1 Hz, 1 H), 2.74 (dd, J=7.1, 16.1 Hz, 1 H), 1.55 (quin, J=5.6 Hz, 2 H), 1.37-1.48 (m, 4 H).

Preparation of 7-nitro-1-oxo-1,2,3,4-tetrahydropyr-rolo[1,2-a]pyrazine-4-carboxylic acid (V, where R1=OH)

LiOH.H$_2$O (27 mg, 1.12 mmol) was added to a solution of ethyl(7-nitro-1-oxo-1,2,3,4-tetrahydropyrrolo[1,2-a]pyrazin-4-yl)acetate (V, where R1=OCH$_2$CH$_3$) (0.15 g, 0.56 mmol) in a mixture tetrahydrofuran-water (1:1, 9 mL) and the reaction mixture was stirred at room temperature for 3 h. The organic phase was washed with dichloromethane (2×10 mL). The aqueous phase was acidified with hydrochloric acid (1 M) to reach pH<1 and extracted with EtOAc (3×10 mL). The combined organic layers were dried over Na$_2$SO$_4$ and the solvent was evaporated under vacuum to obtain compound 7-nitro-1-oxo-1,2,3,4-tetrahydropyrrolo[1,2-a]pyrazine-4-carboxylic acid (V, where R1=OH) as an off-white solid (101 mg, 75% yield).

LCMS (HPLC Method 2): m/z 240 [M+H]$^+$ @ r.t. 1.05 min. $^1$H NMR (400 MHz, DMSO-d$_6$) δ=8.13 (d, J=1.7 Hz, 1 H), 8.11 (d, J=1.7 Hz, 1 H), 7.14 (d, J=1.8 Hz, 1 H), 4.70-4.79 (m, 1 H), 3.71-3.77 (m, 1 H), 3.44 (dt, J=4.3, 13.4 Hz, 1 H), 2.80-2.96 (m, 2H).

General procedure: loading of phenethylamine (corresponding to fragment B6 of Table I) onto Acid Sensitive Methoxy Benzaldehyde polystyrene resin (AMEBA II resin).

4-(4-formyl-3-methoxyphenoxy)butyryl aminomethyl resin (copolystyrene-1% DVB) (6.0 g, 5.88 mmol, 0.98 mmol/g, 1 eq.) was suspended in dry THF (60 ml) and phenethylamine (29.4 mmol, 5 eq.) was added. The resultant suspension was shaken at 25° C. for 2 h. Then acetic acid (1.68 ml, 29.4 mmol, 5 eq.) and NaBH(AcO)$_3$ (3.12 g, 14.7 mmol, 3 eq.) were added and the final suspension was shaken for 16 h at 25° C. The resin was rinsed with THF (2 cycles), MeOH (2 cycles), DCM (2 cycles), MeOH (2 cycles), DMF (2 cycles) and DCM (3 cycles) then dried in nitrogen flux.

Loading of the 3,4-dihydro-2H-pyrrolo[1,2-a]pyrazin-1-one scaffold onto the resin prepared as described above.

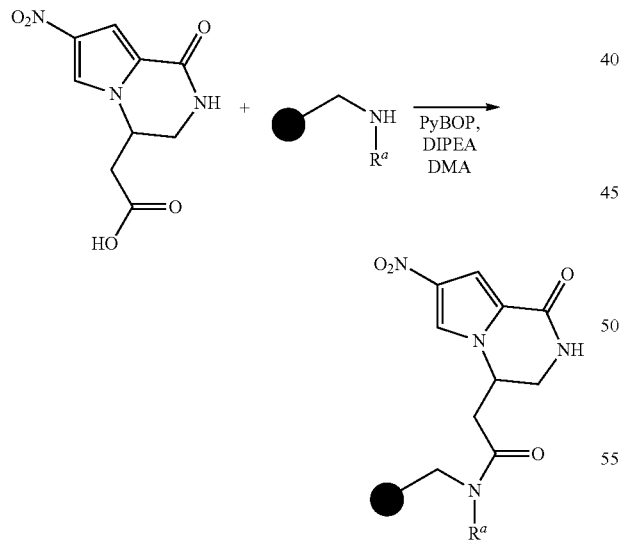

A solution of 7-nitro-1-oxo-1,2,3,4-tetrahydropyrrolo[1,2-a]pyrazine-4-carboxylic acid (V, where R1=OH) (0.24 g, 1 mmol), N,N-diisopropylethylamine (DIPEA) (0.34 ml, 2 mmol) and benzotriazol-1-yloxytripyrrolidinophosphonium hexafluorophosphate (PyBOP) (0.52 g, 1 mmol) in dry N,N-dimethylacetamide (7.5 ml) was stirred for 30 min, then was added to resin of example 17 (0.67 mmol, 1 eq) and the final suspension was shaken for 24 h at room temperature. The resin was rinsed with a cycle of DMF, MeOH, DCM (3 times), DCM (3 times) and 1,4-dioxane (once) and dried under nitrogen flux. The resin was then used in the next step.

Reduction of the nitro group:

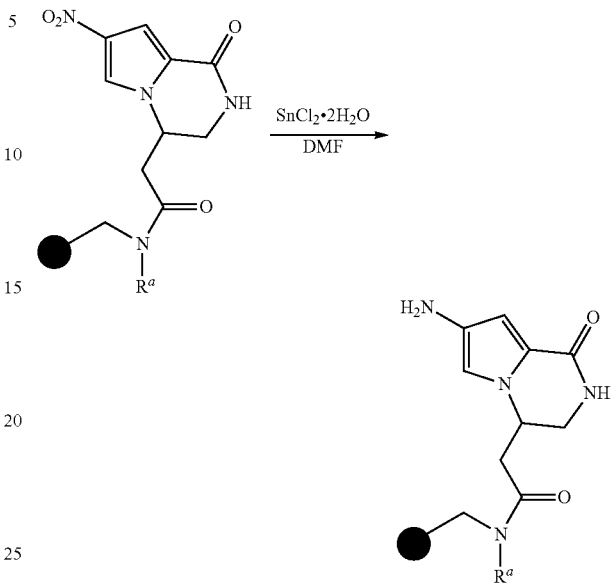

The resin of formula (XVIII) (0.67 mmol, 1 eq) was suspended in a 2M solution of SnCl$_2$.2H$_2$O in N,N-dimethylformamide (10 ml). The final suspension was shaken for 48 hours at room temperature. The resin was rinsed with a cycle of DMF, MeOH, DCM (3 times), DCM (3 times) and 1,4-dioxane (once) and dried under nitrogen flux. The resin was then used in the next step.

The above resin bound 3,4-dihydro-2H-pyrrolo[1,2-a]pyrazin-1-one was further reacted according to the alternative steps below so as to get carboxamido and ureido derivatives.

Example 10

Preparation of A11-M-B6 (Entry 71, Table III)

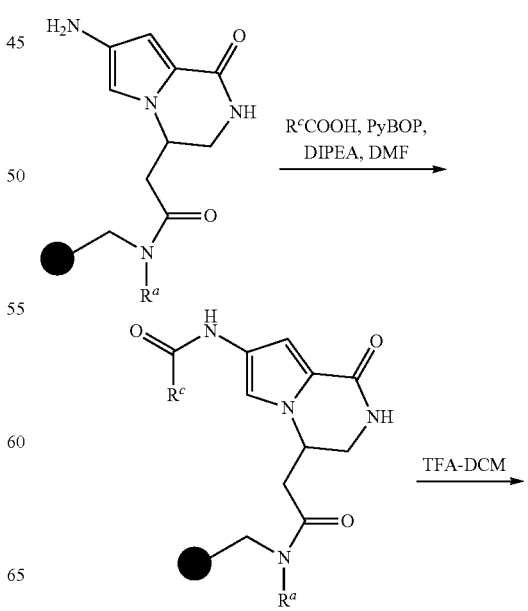

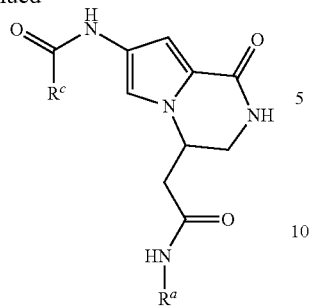

A carboxylic acid of formula (VI), wherein $R^c$ corresponds to the fragment A11 of table II (1.35 mmol, 15 eq.) was added to a solution of 1-ethyl-3-(3'-dimethylaminopropyl)carbodiimide (EDC) (0.26 g, 1.35 mmol, 15 eq) and 3,4-dihydro-3-hydroxy-4-oxo-1,2,3-benzotriazine (DHBT) (0.22 g, 1.35 mmol, 15 eq) in dried N-methylpyrrolidone (NMP) (1 ml) and the solution was stirred for 30 min, then was added to resin of example 19 (0.09 mmol, 1 eq.) and shaken overnight at room temperature in a reactor (Quest 210™ or Miniblocks™). The resin was rinsed with a cycle of DMF, MeOH, DCM (3 times), DCM (3 times) and 1,4-dioxane (once) and dried under nitrogen flux. The resin was suspended in a solution of TFA-DCM (1:1, 2 ml) and shaken for 2 h at room temperature. The solution was collected and the resin was rinsed with DCM (collected as well), and a second cycle was performed. The final washing was performed with MeOH. All the collected organic layers were dried under reduced pressure affording compound A11-M-B6 (see entry 71 of table III below).

LCMS (HPLC Method 2): m/z 399 [M+H]$^+$ @ r.t. 2.7 min. $^1$H NMR (400 MHz, DMSO-d$_6$) δ=10.53 (s, 1 H), 9.74 (br. s., 1 H), 8.07 (t, J=5.6 Hz, 1 H), 7.67 (d, J=3.5 Hz, 1 H), 7.12-7.32 (m, 6 H), 6.60 (d, J=1.7 Hz, 1 H), 4.48-4.67 (m, 1 H), 3.94-4.09 (m, 2H), 3.66 (dd, J=4.6, 13.3 Hz, 1 H), 2.81 (s, 6 H), 2.63-2.75 (m, 2 H).

Example 11

Preparation of A17-M-B6 (Entry 117, Table III)

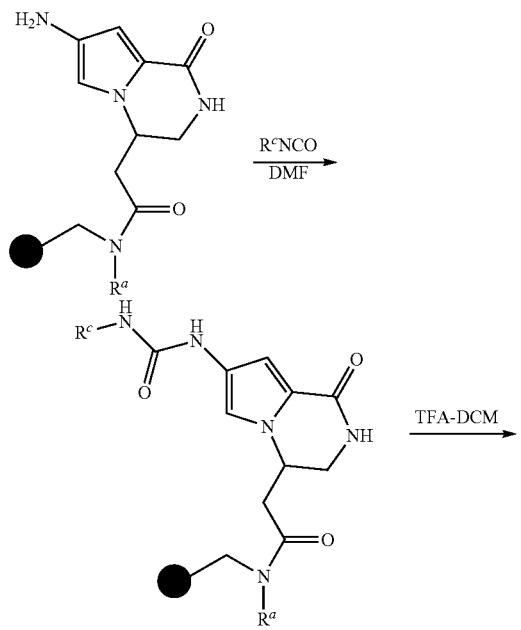

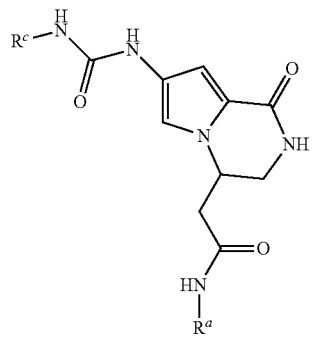

An isocyanate of formula (VII) wherein $R^c$ corresponds to fragment A17 of table II (1.35 mmol, 15 eq) was added to a suspension of the resin of example 19 (0.09 mmol, 1 eq) in dry dichloromethane (1 ml). The final suspension was shaken overnight at room temperature in a reactor (Quest 210™ or Miniblocks™). The resin was rinsed with a cycle of DMF, MeOH, DCM (3 times), DCM (3 times) and 1,4-dioxane (once) and dried under nitrogen flux. The resin was suspended in a solution of TFA-DCM (1:1, 2 ml) and shaken for 2 h at room temperature. The solution was collected and the resin was rinsed with DCM (collected as well), and a second cycle was performed. The final washing was performed with MeOH. All the collected organic layers were dried under reduced pressure affording compound A17-M-B6 (see entry 117 of table III below).

LCMS (HPLC Method 2): m/z 463 [M+H]$^+$ @ r.t. 4.02 min. $^1$H NMR (400 MHz, DMSO-d$_6$) δ=8.29 (s, 1 H), 8.26 (s, 1 H), 8.07 (t, J=5.7 Hz, 1 H), 7.52 (d, J=3.0 Hz, 1H), 7.28-7.33 (m, 2 H), 7.10 (d, J=1.8 Hz, 1 H), 6.77-6.85 (m, 2 H), 6.46 (d, J=1.7 Hz, 1 H), 4.50 (tt, J=3.9, 6.9 Hz, 0 H), 3.70 (s, 4 H), 3.63 (ddd, J=1.3, 4.2, 12.8 Hz, 1 H).

Preparation of 7-iodo-1-oxo-1,2,3,4-tetrahydropyrrolo[1,2-a]pyrazine-4-carboxylic acid (XI, where R1=OH)

LiOH.H$_2$O (63 mg, 1.5 mmol) was added to a solution of ethyl(7-iodo-1-oxo-1,2,3,4-tetrahydropyrrolo[1,2-a]pyrazin-4-yl)acetate (XII, where R1=OCH$_2$CH$_3$) (0.26 g, 0.75 mmol) in a mixture tetrahydrofuran-water (1:1, 8 mL) and the reaction mixture was stirred at room temperature for 3 h. The organic phase was washed with dichloromethane (2×10 mL). The aqueous phase was acidified with hydrochloric acid (1 M) to reach pH<1 and extracted with EtOAc (3×10 mL). The combined organic layers were dried over Na$_2$SO$_4$ and the solvent was evaporated under vacuum to obtain compound 7-iodo-1-oxo-1,2,3,4-tetrahydropyrrolo[1,2-a]pyrazine-4-carboxylic acid (XII, where R1=OH) as an off-white solid (0.23 g, 75% yield).

LCMS (HPLC Method 2): m/z 321 [M+H]$^+$ @ r.t. 2.52 min. $^1$H NMR (400 MHz, DMSO-d$_6$) δ=12.63 (br. s., 1 H), 7.71 (br. s., 1 H), 7.14 (d, J=1.7 Hz, 1 H), 6.72 (d, J=1.7 Hz, 1 H), 4.54-4.66 (m, 1 H), 3.59-3.70 (m, 1 H), 3.32-3.38 (m, 1 H), 2.76 (d, J=7.0 Hz, 2 H).

Loading of the 3,4-dihydro-2H-pyrrolo[1,2-a]pyrazin-1-one scaffold onto the resin prepared as described previously.

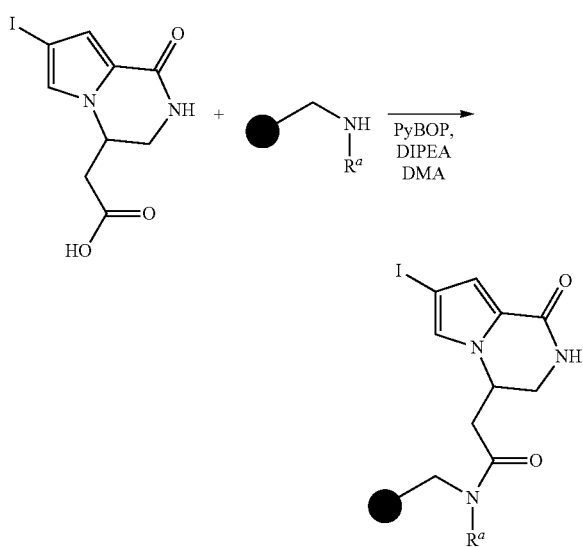

A solution of 7-iodo-1-oxo-1,2,3,4-tetrahydropyrrolo[1,2-a]pyrazine-4-carboxylic acid (XI, where R1=OH) (0.92 g, 2.87 mmol), N,N-diisopropylethylamine (DIPEA) (0.99 ml, 5.76 mmol) and benzotriazol-1-yloxytripyrrolidinophosphonium hexafluorophosphate (PyBOP) (1.5 g, 2.87 mmol) in dry N,N-dimethylacetamide (9 ml) was stirred for 30 min, then was added to resin of example 17 (1.44 mmol, 1 eq) and the final suspension was shaken for 24 h at room temperature. The resin was rinsed with a cycle of DMF, MeOH, DCM (3 times), DCM (3 times) and 1,4-dioxane (once) and dried under nitrogen flux. The resin was then used in the next step.

Example 12

Preparation of A24-M-B6 (Entry 135, Table III)

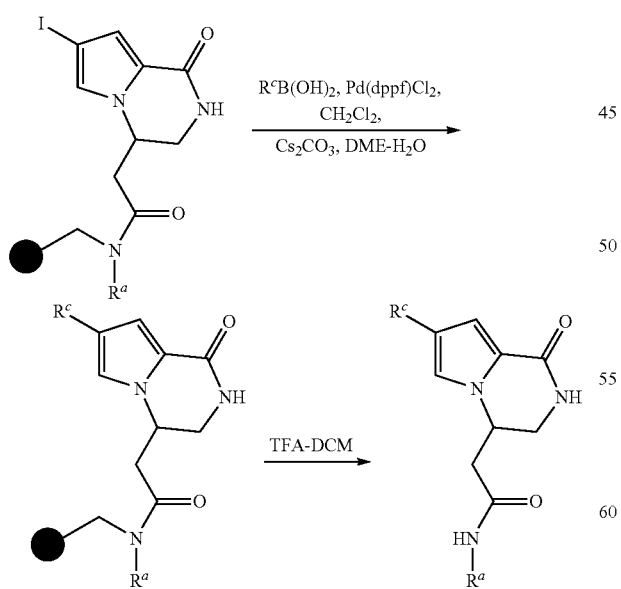

A mixture of boronic acid of formula (XII), wherein $R^c$ corresponds to the fragment A24 of table II (0.37 g, 3 mmol*), 1,1'-bis(diphenylphosphino)ferrocenepalladium(II)dichloride complex with dichloromethane (1:1) (PdCl$_2$(dppf).CH$_2$Cl$_2$) (65 mg, 0.08 mmol), cesium carbonate (0.52 g, 1.6 mmol) and the resin from example 23 (0.2 mmol, 1 eq.) in a mixture dimethoxyethane-water (3:1, 2 mL) was shaken overnight at 80° C. in a reactor (Quest 210™). The resin was rinsed with a cycle of DMF, MeOH, DCM (3 times), DCM (3 times) and 1,4-dioxane (once) and dried under nitrogen flux. The resin was suspended in a solution of TFA-DCM (1:1, 2 ml) and shaken for 2 h at room temperature. The solution was collected and the resin was rinsed with DCM (collected as well), and a second cycle was performed. The final washing was performed with MeOH. All the collected organic layers were dried under reduced pressure affording compound A24-M-B6 (see entry 135 of table III below).

LCMS (HPLC Method 2): m/z 376 [M+H]$^+$ @ r.t. 4.17 min. $^1$H NMR (400 MHz, DMSO-d$_6$) δ=8.64 (d, J=6.3 Hz, 2 H), 8.11 (s, 1 H), 8.05 (d, J=6.5 Hz, 2 H), 7.95 (d, J=1.6 Hz, 1 H), 7.88 (d, 1 H), 7.47 (d, J=1.7 Hz, 1 H), 7.23 (t, J=7.4 Hz, 2 H), 7.15 (t, J=7.3 Hz, 1 H), 7.10 (dd, J=1.5, 7.4 Hz, 2 H), 4.73 (tt, J=3.7, 7.1 Hz, 1 H), 3.68 (ddd, 1 H).

Following the procedure described in examples 4-6, 9-11, 14-15 and 16-24 and by using any proper reactant as per the process of the invention, the following compounds of table III were also prepared.

TABLE III

| Entry | Compound | HPLC Method | HPLC Rt (min) | [M + H]$^+$ |
|---|---|---|---|---|
| 1 | A1-M-B1 | 2 | 5.17 | 323.2 |
| 2 | A1-M-B2 | 2 | 4.49 | 295.2 |
| 3 | A1-M-B6 | 2 | 6.04 | 398.3 |
| 4 | A1-M-B7 | 2 | 5.06 | 352.3 |
| 5 | A1-M-B8 | 2 | 4.27 | 380.3 |
| 6 | A1-M-B9 | 2 | 6.05 | 364.3 |
| 7 | A2-M-B1 | 2 | 4.53 | 329.2 |
| 8 | A2-M-B2 | 2 | 3.06 | 301.2 |
| 9 | A2-M-B3 | 2 | 5.31 | 357.3 |
| 10 | A2-M-B4 | 2 | 4.15 | 398.3 |
| 11 | A3-M-B1 | 2 | 3.92 | 372.2 |
| 12 | A3-M-B2 | 2 | 2.8 | 344.2 |
| 13 | A3-M-B5 | 2 | 3.77 | 411.3 |
| 14 | A4-M-B1 | 2 | 4.08 | 392.2 |
| 15 | A4-M-B10 | 2 | 3.72 | 461.3 |
| 16 | A4-M-B11 | 2 | 3.8 | 461.3 |
| 17 | A4-M-B2 | 2 | 2.86 | 364.2 |
| 18 | A5-M-B1 | 2 | 3.95 | 357.2 |
| 19 | A5-M-B12 | 1 | 2.54 | 412.3 |
| 20 | A5-M-B16 | 1 | 3.19 | 432.3 |
| 21 | A5-M-B17 | 1 | 2.38 | 356.3 |
| 22 | A5-M-B18 | 1 | 3.6 | 424.3 |
| 23 | A5-M-B2 | 2 | 2.72 | 329.2 |
| 24 | A5-M-B21 | 1 | 3.34 | 432.3 |
| 25 | A5-M-B22 | 1 | 3.55 | 424.3 |
| 26 | A5-M-B23 | 1 | 2.94 | 384.3 |
| 27 | A5-M-B24 | 1 | 3.28 | 410.3 |
| 28 | A5-M-B26 | 1 | 2.99 | 396.3 |
| 29 | A5-M-B5 | 2 | 3.74 | 396.3 |
| 30 | A5-M-B7 | 2 | 3.11 | 386.3 |
| 31 | A5-M-B7 | 1 | 2.34 | 386.3 |
| 32 | A5-M-B8 | 2 | 2.72 | 413.3 |
| 33 | A6-M-B1 | 2 | 4.18 | 321.2 |
| 34 | A7-M-B1 | 2 | 3.99 | 360.2 |
| 35 | A7-M-B12 | 1 | 2.62 | 415.3 |
| 36 | A7-M-B13 | 1 | 2.7 | 373.3 |
| 37 | A7-M-B14 | 1 | 3.11 | 421.3 |
| 38 | A7-M-B16 | 1 | 3.33 | 435.3 |
| 39 | A7-M-B17 | 1 | 2.48 | 359.2 |
| 40 | A7-M-B18 | 1 | 3.64 | 427.3 |
| 41 | A7-M-B19 | 1 | 2.49 | 371.2 |
| 42 | A7-M-B2 | 2 | 3.7 | 332.2 |
| 43 | A7-M-B20 | 1 | 3.35 | 435.3 |
| 44 | A7-M-B21 | 1 | 3.38 | 435.3 |
| 45 | A7-M-B22 | 1 | 3.59 | 427.3 |
| 46 | A7-M-B23 | 1 | 3 | 387.3 |

TABLE III-continued

| Entry | Compound | HPLC Method | HPLC Rt (min) | [M + H]+ |
|---|---|---|---|---|
| 47 | A7-M-B24 | 1 | 3.33 | 413.3 |
| 48 | A7-M-B25 | 1 | 2.73 | 373.3 |
| 49 | A7-M-B26 | 1 | 3.06 | 399.3 |
| 50 | A7-M-B27 | 1 | 2.61 | 371.2 |
| 51 | A7-M-B7 | 1 | 2.43 | 389.3 |
| 52 | A8-M-B1 | 2 | 3.96 | 396.2 |
| 53 | A8-M-B2 | 2 | 3.5 | 368.2 |
| 54 | A9-M-B1 | 2 | 4.04 | 375.2 |
| 55 | A9-M-B14 | 1 | 3.19 | 436.3 |
| 56 | A9-M-B15 | 1 | 3.04 | 402.3 |
| 57 | A9-M-B16 | 1 | 3.38 | 450.3 |
| 58 | A9-M-B17 | 1 | 2.53 | 374.3 |
| 59 | A9-M-B18 | 1 | 3.69 | 442.3 |
| 60 | A9-M-B19 | 1 | 2.56 | 386.3 |
| 61 | A9-M-B2 | 2 | 3.68 | 347.2 |
| 62 | A9-M-B20 | 1 | 3.43 | 450.3 |
| 63 | A9-M-B21 | 1 | 3.47 | 450.3 |
| 64 | A9-M-B22 | 1 | 3.66 | 442.3 |
| 65 | A9-M-B23 | 1 | 3.08 | 402.3 |
| 66 | A9-M-B24 | 1 | 3.41 | 428.3 |
| 67 | A9-M-B26 | 1 | 3.13 | 414.3 |
| 68 | A9-M-B27 | 1 | 2.67 | 386.3 |
| 69 | A9-M-B7 | 1 | 2.48 | 404.3 |
| 70 | A10-M-B2 | 2 | 1.34 | 265.2 |
| 71 | A11-M-B6 | 2 | 2.7 | 398.3 |
| 72 | A11-M-B7 | 2 | 1.06 | 352.3 |
| 73 | A11-M-B8 | 2 | 3.32 | 379.3 |
| 74 | A11-M-B9 | 2 | 2.52 | 364.3 |
| 75 | A12-M-B13 | 1 | 1.99 | 319.3 |
| 76 | A12-M-B14 | 1 | 2.43 | 367.3 |
| 77 | A12-M-B16 | 1 | 2.71 | 381.3 |
| 78 | A12-M-B20 | 1 | 2.73 | 381.3 |
| 79 | A12-M-B21 | 1 | 2.79 | 381.3 |
| 80 | A12-M-B22 | 1 | 3.03 | 373.3 |
| 81 | A12-M-B7 | 2 | 3.29 | 335.3 |
| 82 | A12-M-B8 | 2 | 2.69 | 362.3 |
| 83 | A13-M-B7 | 2 | 2.81 | 334.2 |
| 84 | A13-M-B8 | 2 | 1.26 | 361.3 |
| 85 | A13-M-B9 | 2 | 3.12 | 346.3 |
| 86 | A14-M-B7 | 2 | 3.84 | 389.2 |
| 87 | A14-M-B8 | 2 | 3.03 | 416.3 |
| 88 | A15-M-B12 | 1 | 2.61 | 417.3 |
| 89 | A15-M-B13 | 1 | 2.68 | 375.2 |
| 90 | A15-M-B14 | 1 | 3.07 | 423.2 |
| 91 | A15-M-B15 | 1 | 2.92 | 389.3 |
| 92 | A15-M-B16 | 1 | 3.28 | 437.3 |
| 93 | A15-M-B18 | 1 | 3.59 | 429.3 |
| 94 | A15-M-B19 | 1 | 2.52 | 373.2 |
| 95 | A15-M-B20 | 1 | 3.3 | 437.3 |
| 96 | A15-M-B21 | 1 | 3.32 | 437.3 |
| 97 | A15-M-B22 | 1 | 3.52 | 429.3 |
| 98 | A15-M-B23 | 1 | 2.97 | 389.3 |
| 99 | A15-M-B24 | 1 | 3.28 | 415.3 |
| 100 | A15-M-B25 | 1 | 2.72 | 375.2 |
| 101 | A15-M-B26 | 1 | 3.02 | 401.3 |
| 102 | A15-M-B27 | 1 | 2.6 | 373.2 |
| 103 | A15-M-B7 | 1 | 2.44 | 391.2 |
| 104 | A15-M-B8 | 2 | 2.85 | 418.3 |
| 105 | A16-M-B14 | 1 | 3.32 | 424.3 |
| 106 | A16-M-B18 | 1 | 3.83 | 430.4 |
| 107 | A16-M-B20 | 1 | 3.56 | 438.3 |
| 108 | A16-M-B21 | 1 | 3.6 | 438.3 |
| 109 | A16-M-B22 | 1 | 3.81 | 430.4 |
| 110 | A16-M-B23 | 1 | 3.23 | 390.3 |
| 111 | A16-M-B24 | 1 | 3.54 | 416.4 |
| 112 | A16-M-B27 | 1 | 2.82 | 374.3 |
| 113 | A16-M-B8 | 2 | 2.89 | 419.4 |
| 114 | A17-M-B14 | 1 | 2.89 | 448.3 |
| 115 | A17-M-B21 | 1 | 3.17 | 462.3 |
| 116 | A17-M-B24 | 1 | 3.11 | 440.3 |
| 117 | A17-M-B6 | 2 | 4.02 | 462.3 |
| 118 | A17-M-B8 | 2 | 2.72 | 443.3 |
| 119 | A17-M-B9 | 2 | 3.97 | 428.3 |
| 120 | A18-M-B5 | 2 | 3.62 | 399.3 |
| 121 | A19-M-B5 | 2 | 4.38 | 388.3 |
| 122 | A20-M-B1 | 2 | 5.13 | 333.2 |
| 123 | A20-M-B6 | 2 | 5.98 | 408.2 |
| 124 | A20-M-B7 | 2 | 4.99 | 362.2 |
| 125 | A20-M-B8 | 2 | 3.33 | 389.2 |
| 126 | A20-M-B9 | 2 | 5.99 | 374.3 |
| 127 | A21-M-B1 | 2 | 4.61 | 344.2 |
| 128 | A22-M-B1 | 2 | 5.12 | 355.3 |
| 129 | A22-M-B2 | 2 | 4.4 | 327.2 |
| 130 | A22-M-B6 | 2 | 5.87 | 430.3 |
| 131 | A22-M-B7 | 2 | 4.94 | 384.3 |
| 132 | A22-M-B8 | 2 | 4.14 | 411.3 |
| 133 | A22-M-B9 | 2 | 5.88 | 396.3 |
| 135 | A24-M-B6 | 2 | 4.17 | 375.3 |
| 136 | A24-M-B7 | 2 | 2.45 | 329.3 |
| 137 | A24-M-B8 | 2 | 1.97 | 356.3 |
| 138 | A24-M-B9 | 2 | 4.07 | 341.3 |
| 139 | A25-M-B1 | 2 | 6.16 | 315.3 |
| 140 | A25-M-B2 | 2 | 4.58 | 287.2 |
| 141 | A25-M-B6 | 2 | 6.23 | 390.3 |
| 142 | A25-M-B7 | 2 | 5.2 | 344.3 |
| 143 | A25-M-B8 | 2 | 4.3 | 371.3 |
| 144 | A25-M-B9 | 2 | 6.24 | 356.3 |
| 145 | A26-M-B1 | 2 | 5.9 | 353.2 |
| 146 | A26-M-B2 | 2 | 4.48 | 325.2 |
| 147 | A26-M-B6 | 2 | 5.96 | 428.3 |
| 148 | A26-M-B7 | 2 | 5.04 | 382.3 |
| 149 | A26-M-B8 | 2 | 4.22 | 409.3 |
| 150 | A26-M-B9 | 2 | 5.98 | 394.3 |
| 151 | A27-M-B1 | 2 | 6.48 | 357.2 |
| 152 | A27-M-B2 | 2 | 4.98 | 329.2 |
| 153 | A27-M-B6 | 2 | 6.5 | 432.2 |
| 154 | A27-M-B7 | 2 | 5.57 | 386.2 |
| 155 | A27-M-B8 | 2 | 4.72 | 413.2 |
| 156 | A27-M-B9 | 2 | 6.54 | 398.2 |
| 157 | A28-M-B1 | 2 | 6.92 | 416.3 |
| 158 | A28-M-B2 | 2 | 5.52 | 388.3 |
| 159 | A28-M-B6 | 2 | 6.9 | 491.3 |
| 160 | A28-M-B7 | 2 | 6.07 | 445.3 |
| 161 | A28-M-B8 | 2 | 5.16 | 472.4 |
| 162 | A28-M-B9 | 2 | 6.95 | 457.4 |
| 163 | A29-M-B1 | 2 | 5.12 | 263.2 |
| 164 | A29-M-B2 | 2 | 3.51 | 235.2 |
| 165 | A29-M-B6 | 2 | 5.35 | 338.3 |
| 166 | A29-M-B7 | 2 | 4.14 | 292.3 |
| 167 | A29-M-B8 | 2 | 3.35 | 319.3 |
| 168 | A29-M-B9 | 2 | 5.31 | 304.3 |
| 169 | A30-M-B1 | 2 | 6.8 | 331.3 |
| 170 | A30-M-B2 | 2 | 5.11 | 303.3 |
| 171 | A30-M-B6 | 2 | 6.76 | 406.3 |
| 172 | A30-M-B7 | 2 | 5.76 | 360.3 |
| 173 | A30-M-B8 | 2 | 4.78 | 387.4 |
| 174 | A30-M-B9 | 2 | 6.82 | 372.4 |
| 175 | A31-M-B1 | 2 | 5.92 | 325.2 |
| 176 | A31-M-B2 | 2 | 4.45 | 297.2 |
| 177 | A31-M-B6 | 2 | 5.98 | 400.3 |
| 178 | A31-M-B7 | 2 | 5.02 | 354.3 |
| 179 | A31-M-B8 | 2 | 4.17 | 381.3 |
| 180 | A31-M-B9 | 2 | 5.99 | 366.3 |
| 181 | A32-M-B1 | 2 | 6.4 | 359.2 |
| 182 | A32-M-B2 | 2 | 4.92 | 331.2 |
| 183 | A32-M-B6 | 2 | 6.41 | 434.3 |
| 184 | A32-M-B7 | 2 | 5.5 | 388.2 |
| 185 | A32-M-B8 | 2 | 4.7 | 415.3 |
| 186 | A32-M-B9 | 2 | 6.45 | 400.3 |
| 187 | A33-M-B6 | 2 | 5.42 | 380.2 |
| 188 | A33-M-B7 | 2 | 4.33 | 334.2 |
| 189 | A33-M-B8 | 3 | 3.88 | 361.2 |
| 190 | A33-M-B9 | 2 | 5.39 | 346.3 |
| 191 | A34-M-B6 | 2 | 5.55 | 374.3 |
| 192 | A34-M-B7 | 2 | 4.48 | 328.3 |
| 193 | A34-M-B8 | 3 | 4.11 | 355.3 |
| 194 | A34-M-B9 | 2 | 5.49 | 340.3 |
| 195 | A35-M-B7 | 2 | 4.62 | 371.3 |
| 196 | A36-M-B12 | 1 | 3.02 | 425.3 |
| 197 | A36-M-B14 | 1 | 3.44 | 431.3 |
| 198 | A36-M-B15 | 1 | 3.33 | 397.3 |
| 199 | A36-M-B16 | 1 | 3.63 | 445.3 |
| 200 | A36-M-B17 | 1 | 2.91 | 369.3 |
| 201 | A36-M-B20 | 1 | 3.65 | 445.3 |

TABLE III-continued

| Entry | Compound | HPLC Method | HPLC Rt (min) | [M + H]+ |
|---|---|---|---|---|
| 202 | A36-M-B21 | 1 | 3.65 | 445.3 |
| 203 | A36-M-B22 | 1 | 3.85 | 437.3 |
| 204 | A36-M-B26 | 1 | 3.4 | 409.3 |
| 205 | A36-M-B7 | 1 | 2.86 | 399.3 |
| 206 | A37-M-B12 | 1 | 2.3 | 403.2 |
| 207 | A37-M-B13 | 1 | 2.34 | 361.2 |
| 208 | A37-M-B14 | 1 | 2.77 | 409.2 |
| 209 | A37-M-B15 | 1 | 2.61 | 375.2 |
| 210 | A37-M-B16 | 1 | 3 | 423.2 |
| 211 | A37-M-B17 | 1 | 2.14 | 347.2 |
| 212 | A37-M-B18 | 1 | 3.33 | 415.3 |
| 213 | A37-M-B19 | 1 | 2.17 | 359.2 |
| 214 | A37-M-B20 | 1 | 3.02 | 423.2 |
| 215 | A37-M-B21 | 1 | 3.05 | 423.2 |
| 216 | A37-M-B22 | 1 | 3.26 | 415.3 |
| 217 | A37-M-B23 | 1 | 2.65 | 375.2 |
| 218 | A37-M-B24 | 1 | 2.98 | 401.3 |
| 219 | A37-M-B25 | 1 | 2.37 | 361.2 |
| 220 | A37-M-B26 | 1 | 2.7 | 387.2 |
| 221 | A37-M-B27 | 1 | 2.26 | 359.2 |
| 222 | A37-M-B7 | 1 | 2.11 | 377.2 |
| 223 | A38-M-B12 | 1 | 2.75 | 411.3 |
| 224 | A38-M-B13 | 1 | 2.84 | 369.3 |
| 225 | A38-M-B14 | 1 | 3.21 | 417.3 |
| 226 | A38-M-B15 | 1 | 3.07 | 383.3 |
| 227 | A38-M-B16 | 1 | 3.41 | 431.3 |
| 228 | A38-M-B17 | 1 | 2.63 | 355.3 |
| 229 | A38-M-B18 | 1 | 3.7 | 423.3 |
| 230 | A38-M-B19 | 1 | 2.66 | 367.3 |
| 231 | A38-M-B20 | 1 | 3.43 | 431.3 |
| 232 | A38-M-B21 | 1 | 3.46 | 431.3 |
| 233 | A38-M-B22 | 1 | 3.65 | 423.3 |
| 234 | A38-M-B23 | 1 | 3.1 | 383.3 |
| 235 | A38-M-B24 | 1 | 3.41 | 409.3 |
| 236 | A38-M-B25 | 1 | 2.87 | 369.3 |
| 237 | A38-M-B26 | 1 | 3.16 | 395.3 |
| 238 | A38-M-B27 | 1 | 2.74 | 367.3 |
| 239 | A38-M-B7 | 1 | 2.58 | 385.3 |
| 240 | A39-M-B12 | 1 | 2.33 | 422.3 |
| 241 | A39-M-B13 | 1 | 2.39 | 380.3 |
| 242 | A39-M-B14 | 1 | 2.79 | 428.3 |
| 243 | A39-M-B15 | 1 | 2.64 | 394.3 |
| 244 | A39-M-B16 | 1 | 3.02 | 442.3 |
| 245 | A39-M-B18 | 1 | 3.32 | 434.3 |
| 246 | A39-M-B19 | 1 | 2.22 | 378.2 |
| 247 | A39-M-B20 | 1 | 3.02 | 442.3 |
| 248 | A39-M-B21 | 1 | 3.04 | 442.3 |
| 249 | A39-M-B22 | 1 | 3.24 | 434.3 |
| 250 | A39-M-B23 | 1 | 2.67 | 394.3 |
| 251 | A39-M-B24 | 1 | 2.98 | 420.3 |
| 252 | A39-M-B25 | 1 | 2.42 | 380.3 |
| 253 | A39-M-B26 | 1 | 2.72 | 406.3 |
| 254 | A39-M-B27 | 1 | 2.32 | 378.2 |
| 255 | A39-M-B7 | 1 | 2.18 | 396.3 |
| 256 | A40-M-B12 | 1 | 2.31 | 403.2 |
| 257 | A40-M-B13 | 1 | 2.36 | 361.2 |
| 258 | A40-M-B14 | 1 | 2.8 | 409.2 |
| 259 | A40-M-B15 | 1 | 2.63 | 375.2 |
| 260 | A40-M-B16 | 1 | 3.04 | 423.2 |
| 261 | A40-M-B18 | 1 | 3.38 | 415.3 |
| 262 | A40-M-B19 | 1 | 2.17 | 359.2 |
| 263 | A40-M-B20 | 1 | 3.06 | 423.2 |
| 264 | A40-M-B21 | 1 | 3.1 | 423.2 |
| 265 | A40-M-B22 | 1 | 3.31 | 415.3 |
| 266 | A40-M-B23 | 1 | 2.67 | 375.2 |
| 267 | A40-M-B24 | 1 | 3.03 | 401.3 |
| 268 | A40-M-B25 | 1 | 2.39 | 361.2 |
| 269 | A40-M-B26 | 1 | 2.73 | 387.2 |
| 270 | A40-M-B27 | 1 | 2.27 | 359.2 |
| 271 | A40-M-B7 | 1 | 2.13 | 377.2 |
| 272 | A41-M-B12 | 1 | 2.88 | 433.3 |
| 273 | A41-M-B13 | 1 | 2.97 | 391.3 |
| 274 | A41-M-B14 | 1 | 3.36 | 439.3 |
| 275 | A41-M-B15 | 1 | 3.22 | 405.3 |
| 276 | A41-M-B16 | 1 | 3.56 | 453.3 |
| 277 | A41-M-B18 | 1 | 3.8 | 445.3 |
| 278 | A41-M-B19 | 1 | 2.78 | 389.2 |
| 279 | A41-M-B20 | 1 | 3.59 | 453.3 |
| 280 | A41-M-B21 | 1 | 3.6 | 453.3 |
| 281 | A41-M-B22 | 1 | 3.8 | 445.3 |
| 282 | A41-M-B23 | 1 | 3.26 | 405.3 |
| 283 | A41-M-B24 | 1 | 3.57 | 431.3 |
| 284 | A41-M-B25 | 1 | 3 | 391.3 |
| 285 | A41-M-B26 | 1 | 3.31 | 417.3 |
| 286 | A41-M-B27 | 1 | 2.87 | 389.2 |
| 287 | A41-M-B7 | 1 | 2.68 | 407.2 |
| 288 | A42-M-B12 | 1 | 2.89 | 425.3 |
| 289 | A42-M-B13 | 1 | 2.99 | 383.3 |
| 290 | A42-M-B14 | 1 | 3.38 | 431.3 |
| 291 | A42-M-B15 | 1 | 3.23 | 397.3 |
| 292 | A42-M-B16 | 1 | 3.56 | 445.3 |
| 293 | A42-M-B18 | 1 | 3.84 | 437.3 |
| 294 | A42-M-B19 | 1 | 2.8 | 381.3 |
| 295 | A42-M-B20 | 1 | 3.59 | 445.3 |
| 296 | A42-M-B21 | 1 | 3.63 | 445.3 |
| 297 | A42-M-B22 | 1 | 3.82 | 437.3 |
| 298 | A42-M-B23 | 1 | 3.27 | 397.3 |
| 299 | A42-M-B24 | 1 | 3.57 | 423.3 |
| 300 | A42-M-B25 | 1 | 3.02 | 383.3 |
| 301 | A42-M-B26 | 1 | 3.33 | 409.3 |
| 302 | A42-M-B27 | 1 | 2.9 | 381.3 |
| 303 | A42-M-B7 | 1 | 2.73 | 399.3 |
| 304 | A43-M-B12 | 1 | 2.84 | 449.2 |
| 305 | A43-M-B14 | 1 | 3.3 | 455.2 |
| 306 | A43-M-B15 | 1 | 3.16 | 421.2 |
| 307 | A43-M-B16 | 1 | 3.5 | 469.2 |
| 308 | A43-M-B18 | 1 | 3.76 | 461.3 |
| 309 | A43-M-B19 | 1 | 2.74 | 405.2 |
| 310 | A43-M-B20 | 1 | 3.53 | 469.2 |
| 311 | A43-M-B21 | 1 | 3.55 | 469.2 |
| 312 | A43-M-B22 | 1 | 3.75 | 461.3 |
| 313 | A43-M-B23 | 1 | 3.21 | 421.2 |
| 314 | A43-M-B24 | 1 | 3.5 | 447.3 |
| 315 | A43-M-B25 | 1 | 2.95 | 407.2 |
| 316 | A43-M-B26 | 1 | 3.25 | 433.2 |
| 317 | A43-M-B27 | 1 | 2.83 | 405.2 |
| 318 | A43-M-B7 | 1 | 2.66 | 423.2 |
| 319 | A44-M-B13 | 1 | 2.26 | 429.3 |
| 320 | A44-M-B14 | 1 | 2.74 | 381.3 |
| 321 | A44-M-B15 | 1 | 2.54 | 347.3 |
| 322 | A44-M-B16 | 1 | 2.98 | 395.3 |
| 323 | A44-M-B17 | 1 | 2.04 | 319.3 |
| 324 | A44-M-B20 | 1 | 3.02 | 395.3 |
| 325 | A44-M-B21 | 1 | 3.08 | 395.3 |
| 326 | A44-M-B22 | 1 | 3.3 | 387.3 |
| 327 | A44-M-B25 | 1 | 2.29 | 333.3 |
| 328 | A44-M-B26 | 1 | 2.65 | 359.3 |
| 329 | A45-M-B12 | 1 | 2.66 | 391.3 |
| 330 | A45-M-B13 | 1 | 2.77 | 349.3 |
| 331 | A45-M-B14 | 1 | 3.21 | 397.3 |
| 332 | A45-M-B15 | 1 | 3.05 | 363.3 |
| 333 | A45-M-B17 | 1 | 2.52 | 335.3 |
| 334 | A45-M-B20 | 1 | 3.45 | 411.3 |
| 335 | A45-M-B21 | 1 | 3.5 | 411.3 |
| 336 | A45-M-B22 | 1 | 3.72 | 403.4 |
| 337 | A45-M-B25 | 1 | 2.81 | 349.3 |
| 338 | A45-M-B26 | 1 | 3.15 | 375.3 |
| 339 | A45-M-B7 | 1 | 2.46 | 365.3 |
| 340 | A46-M-B12 | 1 | 2.34 | 422.3 |
| 341 | A46-M-B13 | 1 | 2.4 | 380.3 |
| 342 | A46-M-B14 | 1 | 2.8 | 428.3 |
| 343 | A46-M-B15 | 1 | 2.65 | 394.3 |
| 344 | A46-M-B16 | 1 | 3.03 | 442.3 |
| 345 | A46-M-B17 | 1 | 2.21 | 366.2 |
| 346 | A46-M-B18 | 1 | 3.25 | 434.3 |
| 347 | A46-M-B19 | 1 | 2.23 | 378.2 |
| 348 | A46-M-B20 | 1 | 3.04 | 442.3 |
| 349 | A46-M-B25 | 1 | 2.42 | 380.3 |
| 350 | A46-M-B26 | 1 | 2.73 | 406.3 |
| 351 | A46-M-B27 | 1 | 2.32 | 378.2 |
| 352 | A46-M-B7 | 1 | 2.18 | 396.3 |
| 353 | A47-M-B13 | 1 | 2.61 | 369.3 |
| 354 | A47-M-B14 | 1 | 3.06 | 417.3 |
| 355 | A47-M-B15 | 1 | 2.89 | 383.3 |

TABLE III-continued

| Entry | Compound | HPLC Method | HPLC Rt (min) | [M + H]+ |
|---|---|---|---|---|
| 356 | A47-M-B16 | 1 | 3.26 | 431.3 |
| 357 | A47-M-B17 | 1 | 2.38 | 355.3 |
| 358 | A47-M-B18 | 1 | 3.58 | 423.3 |
| 359 | A47-M-B19 | 1 | 2.4 | 367.3 |
| 360 | A47-M-B20 | 1 | 3.31 | 431.3 |
| 361 | A47-M-B21 | 1 | 3.35 | 431.3 |
| 362 | A47-M-B22 | 1 | 3.55 | 423.3 |
| 363 | A47-M-B23 | 1 | 2.92 | 383.3 |
| 364 | A47-M-B24 | 1 | 3.27 | 409.3 |
| 365 | A47-M-B25 | 1 | 2.64 | 369.3 |
| 366 | A47-M-B26 | 1 | 2.99 | 395.3 |
| 367 | A47-M-B27 | 1 | 2.52 | 367.3 |
| 368 | A47-M-B7 | 1 | 2.35 | 385.3 |
| 369 | A48-M-B12 | 1 | 2.77 | 411.3 |
| 370 | A48-M-B13 | 1 | 2.84 | 369.3 |
| 371 | A48-M-B14 | 1 | 3.23 | 417.3 |
| 372 | A48-M-B15 | 1 | 3.09 | 383.3 |
| 373 | A48-M-B16 | 1 | 3.44 | 431.3 |
| 374 | A48-M-B17 | 1 | 2.64 | 355.3 |
| 375 | A48-M-B19 | 1 | 2.67 | 367.3 |
| 376 | A48-M-B20 | 1 | 3.45 | 431.3 |
| 377 | A48-M-B21 | 1 | 3.48 | 431.3 |
| 378 | A48-M-B22 | 1 | 3.67 | 423.3 |
| 379 | A48-M-B26 | 1 | 3.16 | 395.3 |
| 380 | A48-M-B7 | 1 | 2.6 | 385.3 |
| 381 | A49-M-B12 | 1 | 2.78 | 403.3 |
| 382 | A49-M-B13 | 1 | 2.89 | 361.3 |
| 383 | A49-M-B14 | 1 | 3.31 | 409.3 |
| 384 | A49-M-B15 | 1 | 3.16 | 375.3 |
| 385 | A49-M-B16 | 1 | 3.51 | 423.3 |
| 386 | A49-M-B17 | 1 | 2.66 | 347.3 |
| 387 | A49-M-B18 | 1 | 3.82 | 415.4 |
| 388 | A49-M-B19 | 1 | 2.68 | 359.3 |
| 389 | A49-M-B20 | 1 | 3.56 | 423.3 |
| 390 | A49-M-B21 | 1 | 3.59 | 423.3 |
| 391 | A49-M-B22 | 1 | 3.79 | 415.4 |
| 392 | A49-M-B23 | 1 | 3.2 | 375.3 |
| 393 | A49-M-B24 | 1 | 3.53 | 401.3 |
| 394 | A49-M-B25 | 1 | 2.92 | 361.3 |
| 395 | A49-M-B26 | 1 | 3.26 | 387.3 |
| 396 | A49-M-B27 | 1 | 2.8 | 359.3 |
| 397 | A49-M-B7 | 1 | 2.6 | 377.3 |
| 398 | A50-M-B12 | 1 | 2.58 | 391.3 |
| 399 | A50-M-B13 | 1 | 2.66 | 349.3 |
| 400 | A50-M-B14 | 1 | 3.15 | 397.3 |
| 401 | A50-M-B15 | 1 | 2.95 | 363.3 |
| 402 | A50-M-B16 | 1 | 3.33 | 411.3 |
| 403 | A50-M-B17 | 1 | 2.4 | 335.3 |
| 404 | A50-M-B20 | 1 | 3.39 | 411.3 |
| 405 | A50-M-B21 | 1 | 3.44 | 411.3 |
| 406 | A50-M-B22 | 1 | 3.66 | 403.4 |
| 407 | A50-M-B25 | 1 | 2.72 | 349.3 |
| 408 | A50-M-B26 | 1 | 3.06 | 375.3 |
| 409 | A51-M-B12 | 1 | 2.37 | 377.3 |
| 410 | A51-M-B13 | 1 | 2.44 | 335.3 |
| 411 | A51-M-B14 | 1 | 2.91 | 383.3 |
| 412 | A51-M-B15 | 1 | 2.73 | 349.3 |
| 413 | A51-M-B16 | 1 | 3.15 | 397.3 |
| 414 | A51-M-B17 | 1 | 2.2 | 321.3 |
| 415 | A51-M-B22 | 1 | 3.48 | 389.3 |
| 416 | A51-M-B25 | 1 | 2.47 | 335.3 |
| 417 | A51-M-B26 | 1 | 2.83 | 361.3 |
| 418 | A51-M-B27 | 1 | 2.34 | 333.3 |
| 419 | A52-M-B12 | 1 | 2.89 | 425.3 |
| 420 | A52-M-B13 | 1 | 2.99 | 383.3 |
| 421 | A52-M-B14 | 1 | 3.38 | 431.3 |
| 422 | A52-M-B15 | 1 | 3.24 | 397.3 |
| 423 | A52-M-B16 | 1 | 3.56 | 445.3 |
| 424 | A52-M-B18 | 1 | 3.83 | 437.3 |
| 425 | A52-M-B19 | 1 | 2.8 | 381.3 |
| 426 | A52-M-B20 | 1 | 3.59 | 445.3 |
| 427 | A52-M-B21 | 1 | 3.62 | 445.3 |
| 428 | A52-M-B22 | 1 | 3.82 | 437.3 |
| 429 | A52-M-B23 | 1 | 3.28 | 397.3 |
| 430 | A52-M-B24 | 1 | 3.57 | 423.3 |
| 431 | A52-M-B25 | 1 | 3.03 | 383.3 |
| 432 | A52-M-B26 | 1 | 3.33 | 409.3 |
| 433 | A52-M-B27 | 1 | 2.91 | 381.3 |
| 434 | A52-M-B7 | 1 | 2.72 | 399.3 |
| 435 | A53-M-B12 | 1 | 2.26 | 433.3 |
| 436 | A53-M-B13 | 1 | 2.31 | 391.3 |
| 437 | A53-M-B14 | 1 | 2.75 | 439.3 |
| 438 | A53-M-B15 | 1 | 2.57 | 405.3 |
| 439 | A53-M-B16 | 1 | 2.98 | 453.3 |
| 440 | A53-M-B20 | 1 | 3.01 | 453.3 |
| 441 | A53-M-B21 | 1 | 3 | 453.3 |
| 442 | A53-M-B26 | 1 | 2.65 | 417.3 |
| 443 | A53-M-B7 | 1 | 2.08 | 407.2 |
| 444 | A54-M-B13 | 1 | 2.38 | 335.3 |
| 445 | A54-M-B14 | 1 | 2.88 | 383.3 |
| 446 | A54-M-B15 | 1 | 2.67 | 349.3 |
| 447 | A54-M-B20 | 1 | 3.15 | 397.3 |
| 448 | A54-M-B21 | 1 | 3.2 | 397.3 |
| 449 | A54-M-B26 | 1 | 2.78 | 361.3 |
| 450 | A55-M-B12 | 1 | 2.55 | 433.3 |
| 451 | A55-M-B13 | 1 | 2.62 | 391.3 |
| 452 | A55-M-B14 | 1 | 3.06 | 439.3 |
| 453 | A55-M-B15 | 1 | 2.88 | 405.3 |
| 454 | A55-M-B16 | 1 | 3.26 | 453.3 |
| 455 | A55-M-B17 | 1 | 2.4 | 377.2 |
| 456 | A55-M-B18 | 1 | 3.51 | 445.3 |
| 457 | A55-M-B19 | 1 | 2.43 | 389.2 |
| 458 | A55-M-B20 | 1 | 3.29 | 453.3 |
| 459 | A55-M-B21 | 1 | 3.33 | 453.3 |
| 460 | A55-M-B22 | 1 | 3.53 | 445.3 |
| 461 | A55-M-B23 | 1 | 2.93 | 405.3 |
| 462 | A55-M-B25 | 1 | 2.65 | 391.3 |
| 463 | A55-M-B26 | 1 | 2.98 | 417.3 |
| 464 | A55-M-B27 | 1 | 2.53 | 389.2 |
| 465 | A55-M-B7 | 1 | 2.36 | 407.2 |
| 466 | A56-M-B13 | 1 | 2.99 | 391.3 |
| 467 | A56-M-B14 | 1 | 3.38 | 439.3 |
| 468 | A56-M-B15 | 1 | 3.23 | 405.3 |
| 469 | A56-M-B16 | 1 | 3.58 | 453.3 |
| 470 | A56-M-B18 | 1 | 3.86 | 445.3 |
| 471 | A56-M-B19 | 1 | 2.79 | 389.2 |
| 472 | A56-M-B20 | 1 | 3.61 | 453.3 |
| 473 | A56-M-B21 | 1 | 3.62 | 453.3 |
| 474 | A56-M-B22 | 1 | 3.81 | 445.3 |
| 475 | A56-M-B23 | 1 | 3.28 | 405.3 |
| 476 | A56-M-B24 | 1 | 3.59 | 431.3 |
| 477 | A56-M-B25 | 1 | 3.01 | 391.3 |
| 478 | A56-M-B26 | 1 | 3.33 | 417.3 |
| 479 | A56-M-B27 | 1 | 2.89 | 389.2 |
| 480 | A56-M-B7 | 1 | 2.7 | 407.2 |
| 481 | A57-M-B12 | 1 | 3.09 | 425.3 |
| 482 | A57-M-B13 | 1 | 3.2 | 383.3 |
| 483 | A57-M-B14 | 1 | 3.53 | 431.3 |
| 484 | A57-M-B15 | 1 | 3.42 | 397.3 |
| 485 | A57-M-B16 | 1 | 3.71 | 445.3 |
| 486 | A57-M-B18 | 1 | 3.97 | 437.3 |
| 487 | A57-M-B19 | 1 | 3.05 | 381.3 |
| 488 | A57-M-B20 | 1 | 3.73 | 445.3 |
| 489 | A57-M-B21 | 1 | 3.74 | 445.3 |
| 490 | A57-M-B22 | 2 | 5.77 | 437.3 |
| 491 | A57-M-B23 | 1 | 3.45 | 397.3 |
| 492 | A57-M-B24 | 1 | 3.72 | 423.3 |
| 493 | A57-M-B25 | 1 | 3.23 | 383.3 |
| 494 | A57-M-B26 | 1 | 3.49 | 409.3 |
| 495 | A57-M-B27 | 1 | 3.13 | 381.3 |
| 496 | A57-M-B7 | 1 | 2.95 | 399.3 |
| 497 | A58-M-B13 | 1 | 2.53 | 375.2 |
| 498 | A58-M-B15 | 1 | 2.8 | 389.3 |
| 499 | A58-M-B16 | 1 | 3.16 | 437.3 |
| 500 | A58-M-B17 | 1 | 2.32 | 361.3 |
| 501 | A58-M-B20 | 1 | 3.19 | 437.3 |
| 502 | A58-M-B21 | 1 | 3.21 | 437.3 |
| 503 | A58-M-B25 | 1 | 2.56 | 375.2 |
| 504 | A58-M-B26 | 1 | 2.88 | 401.3 |
| 505 | A59-M-B12 | 1 | 2.67 | 449.2 |
| 506 | A59-M-B13 | 1 | 2.75 | 407.2 |
| 507 | A59-M-B14 | 1 | 3.19 | 455.2 |
| 508 | A59-M-B15 | 1 | 3.01 | 421.2 |
| 509 | A59-M-B16 | 1 | 3.38 | 469.2 |

TABLE III-continued

| Entry | Compound | HPLC Method | HPLC Rt (min) | [M + H]+ |
|---|---|---|---|---|
| 510 | A59-M-B18 | 1 | 3.69 | 461.3 |
| 511 | A59-M-B19 | 1 | 2.55 | 405.2 |
| 512 | A59-M-B20 | 1 | 3.41 | 469.2 |
| 513 | A59-M-B21 | 1 | 3.46 | 469.2 |
| 514 | A59-M-B22 | 1 | 3.65 | 461.3 |
| 515 | A59-M-B23 | 1 | 3.06 | 421.2 |
| 516 | A59-M-B25 | 1 | 2.78 | 407.2 |
| 517 | A59-M-B26 | 1 | 3.12 | 433.2 |
| 518 | A59-M-B27 | 1 | 2.65 | 405.2 |
| 519 | A59-M-B7 | 1 | 2.47 | 423.2 |
| 520 | A60-M-B12 | 1 | 2.34 | 377.3 |
| 521 | A60-M-B13 | 1 | 2.4 | 335.3 |
| 522 | A60-M-B14 | 1 | 2.88 | 383.3 |
| 523 | A60-M-B15 | 1 | 2.69 | 349.3 |
| 524 | A60-M-B16 | 1 | 3.1 | 397.3 |
| 525 | A60-M-B20 | 1 | 3.15 | 397.3 |
| 526 | A60-M-B21 | 1 | 3.21 | 397.3 |
| 527 | A60-M-B22 | 1 | 3.44 | 389.3 |
| 528 | A60-M-B23 | 1 | 2.73 | 349.3 |
| 529 | A60-M-B25 | 1 | 2.43 | 335.3 |
| 530 | A60-M-B26 | 1 | 2.81 | 361.3 |
| 531 | A60-M-B27 | 1 | 2.3 | 333.3 |
| 532 | A61-M-B13 | 1 | 2.52 | 335.3 |
| 533 | A61-M-B14 | 1 | 2.98 | 383.3 |
| 534 | A61-M-B15 | 1 | 2.8 | 349.3 |
| 535 | A61-M-B16 | 1 | 3.2 | 397.3 |
| 536 | A61-M-B17 | 1 | 2.27 | 321.3 |
| 537 | A61-M-B19 | 1 | 2.31 | 333.3 |
| 538 | A61-M-B20 | 1 | 3.25 | 397.3 |
| 539 | A61-M-B21 | 1 | 3.3 | 397.3 |
| 540 | A61-M-B26 | 1 | 2.9 | 361.3 |
| 541 | A62-M-B12 | 1 | 2.42 | 397.3 |
| 542 | A62-M-B13 | 1 | 2.49 | 355.3 |
| 543 | A62-M-B14 | 1 | 2.91 | 403.3 |
| 544 | A62-M-B15 | 1 | 2.75 | 369.3 |
| 545 | A62-M-B16 | 1 | 3.13 | 417.3 |
| 546 | A62-M-B17 | 1 | 2.26 | 341.3 |
| 547 | A62-M-B18 | 1 | 3.46 | 409.3 |
| 548 | A62-M-B19 | 1 | 2.29 | 353.3 |
| 549 | A62-M-B20 | 1 | 3.16 | 417.3 |
| 550 | A62-M-B21 | 1 | 3.2 | 417.3 |
| 551 | A62-M-B22 | 1 | 3.39 | 409.3 |
| 552 | A62-M-B23 | 1 | 2.78 | 369.3 |
| 553 | A62-M-B24 | 1 | 3.12 | 395.3 |
| 554 | A62-M-B25 | 1 | 2.51 | 355.3 |
| 555 | A62-M-B26 | 1 | 2.83 | 381.3 |
| 556 | A62-M-B27 | 1 | 2.38 | 353.3 |
| 557 | A62-M-B7 | 1 | 2.24 | 371.3 |
| 558 | A63-M-B12 | 1 | 2.96 | 429.3 |
| 559 | A63-M-B13 | 1 | 3.07 | 387.3 |
| 560 | A63-M-B14 | 1 | 3.41 | 435.3 |
| 561 | A63-M-B15 | 1 | 3.3 | 401.3 |
| 562 | A63-M-B16 | 1 | 3.6 | 449.3 |
| 563 | A63-M-B17 | 1 | 2.86 | 373.3 |
| 564 | A63-M-B18 | 1 | 3.88 | 441.3 |
| 565 | A63-M-B19 | 1 | 2.89 | 385.3 |
| 566 | A63-M-B20 | 1 | 3.63 | 449.3 |
| 567 | A63-M-B21 | 1 | 3.64 | 449.3 |
| 568 | A63-M-B22 | 1 | 3.83 | 441.3 |
| 569 | A63-M-B26 | 1 | 3.38 | 413.3 |
| 570 | A63-M-B27 | 1 | 2.99 | 385.3 |
| 571 | A63-M-B7 | 1 | 2.82 | 403.3 |
| 572 | A64-M-B12 | 1 | 2.34 | 415.3 |
| 573 | A64-M-B14 | 1 | 2.84 | 421.3 |
| 574 | A64-M-B15 | 1 | 2.67 | 387.3 |
| 575 | A64-M-B16 | 1 | 3.06 | 435.3 |
| 576 | A64-M-B17 | 1 | 2.22 | 359.2 |
| 577 | A64-M-B20 | 1 | 3.09 | 435.3 |
| 578 | A64-M-B21 | 1 | 3.13 | 435.3 |
| 579 | A64-M-B22 | 1 | 3.33 | 427.3 |
| 580 | A64-M-B26 | 1 | 2.75 | 399.3 |
| 581 | A64-M-B27 | 1 | 2.34 | 371.2 |
| 582 | A64-M-B7 | 1 | 2.19 | 389.3 |
| 583 | A65-M-B12 | 1 | 2.51 | 389.3 |
| 584 | A65-M-B14 | 1 | 3.05 | 395.3 |
| 585 | A65-M-B15 | 1 | 2.86 | 361.3 |
| 586 | A65-M-B16 | 1 | 3.26 | 409.3 |
| 587 | A65-M-B17 | 1 | 2.34 | 333.3 |
| 588 | A65-M-B18 | 1 | 3.59 | 401.3 |
| 589 | A65-M-B19 | 1 | 2.37 | 345.3 |
| 590 | A65-M-B20 | 1 | 3.3 | 409.3 |
| 591 | A65-M-B21 | 1 | 3.34 | 409.3 |
| 592 | A65-M-B22 | 1 | 3.57 | 401.3 |
| 593 | A65-M-B26 | 1 | 2.97 | 373.3 |
| 594 | A65-M-B7 | 1 | 2.3 | 363.3 |
| 595 | A66-M-B12 | 1 | 2.56 | 449.2 |
| 596 | A66-M-B14 | 1 | 3.08 | 455.2 |
| 597 | A66-M-B15 | 1 | 2.9 | 421.2 |
| 598 | A66-M-B16 | 1 | 3.29 | 469.2 |
| 599 | A66-M-B20 | 1 | 3.32 | 469.2 |
| 600 | A66-M-B21 | 1 | 3.35 | 469.2 |
| 601 | A66-M-B25 | 1 | 2.66 | 407.2 |
| 602 | A66-M-B26 | 1 | 3.02 | 433.2 |
| 603 | A67-M-B12 | 1 | 2.5 | 433.3 |
| 604 | A67-M-B14 | 1 | 3 | 439.3 |
| 605 | A67-M-B15 | 1 | 2.84 | 405.3 |
| 606 | A67-M-B16 | 1 | 3.21 | 453.3 |
| 607 | A67-M-B18 | 1 | 3.45 | 445.3 |
| 608 | A67-M-B19 | 1 | 2.37 | 389.2 |
| 609 | A67-M-B20 | 1 | 3.24 | 453.3 |
| 610 | A67-M-B21 | 1 | 3.28 | 453.3 |
| 611 | A67-M-B26 | 1 | 2.92 | 417.3 |
| 612 | A67-M-B27 | 1 | 2.49 | 389.2 |
| 613 | A67-M-B7 | 1 | 2.32 | 407.2 |
| 614 | A68-M-B12 | 1 | 2.43 | 431.2 |
| 615 | A68-M-B14 | 1 | 2.95 | 437.2 |
| 616 | A68-M-B15 | 1 | 2.78 | 403.2 |
| 617 | A68-M-B16 | 1 | 3.17 | 451.2 |
| 618 | A68-M-B17 | 1 | 2.29 | 375.2 |
| 619 | A68-M-B18 | 1 | 3.47 | 443.3 |
| 620 | A68-M-B19 | 1 | 2.31 | 387.2 |
| 621 | A68-M-B20 | 1 | 3.19 | 451.2 |
| 622 | A68-M-B21 | 1 | 3.24 | 451.2 |
| 623 | A68-M-B26 | 1 | 2.87 | 415.2 |
| 624 | A68-M-B27 | 1 | 2.41 | 387.2 |
| 625 | A68-M-B7 | 1 | 2.25 | 405.2 |
| 626 | A69-M-B14 | 1 | 2.61 | 369.3 |
| 627 | A69-M-B15 | 1 | 2.38 | 335.3 |
| 628 | A69-M-B16 | 1 | 2.85 | 383.3 |
| 629 | A69-M-B20 | 1 | 2.9 | 383.3 |
| 630 | A69-M-B21 | 1 | 2.95 | 383.3 |
| 631 | A69-M-B25 | 1 | 2.15 | 321.3 |
| 632 | A69-M-B26 | 1 | 2.5 | 347.3 |
| 633 | A70-M-B12 | 1 | 2.62 | 415.3 |
| 634 | A70-M-B14 | 1 | 3.12 | 421.3 |
| 635 | A70-M-B15 | 1 | 2.97 | 387.3 |
| 636 | A70-M-B16 | 1 | 3.33 | 435.3 |
| 637 | A70-M-B17 | 1 | 2.48 | 359.2 |
| 638 | A70-M-B18 | 1 | 3.63 | 427.3 |
| 639 | A70-M-B19 | 1 | 2.5 | 371.2 |
| 640 | A70-M-B20 | 1 | 3.35 | 435.3 |
| 641 | A70-M-B21 | 1 | 3.37 | 435.3 |
| 642 | A70-M-B26 | 1 | 3.06 | 399.3 |
| 643 | A70-M-B27 | 1 | 2.61 | 371.2 |
| 644 | A70-M-B7 | 1 | 2.43 | 389.3 |
| 645 | A71-M-B14 | 1 | 2.58 | 369.3 |
| 646 | A71-M-B16 | 1 | 2.84 | 383.3 |
| 647 | A71-M-B20 | 1 | 2.87 | 383.3 |
| 648 | A71-M-B21 | 1 | 2.93 | 383.3 |
| 649 | A71-M-B25 | 1 | 2.11 | 321.3 |
| 650 | A72-M-B14 | 1 | 2.52 | 421.3 |
| 651 | A72-M-B16 | 1 | 2.74 | 435.3 |
| 652 | A72-M-B18 | 1 | 3.06 | 427.3 |
| 653 | A72-M-B20 | 1 | 2.75 | 435.3 |
| 654 | A72-M-B21 | 1 | 2.77 | 435.3 |
| 655 | A72-M-B27 | 1 | 2.07 | 371.3 |
| 656 | A73-M-B12 | 1 | 2.66 | 430.3 |
| 657 | A73-M-B14 | 1 | 3.17 | 436.3 |
| 658 | A73-M-B17 | 1 | 2.17 | 374.3 |
| 659 | A73-M-B20 | 1 | 3.4 | 450.3 |
| 660 | A73-M-B21 | 1 | 3.45 | 450.3 |
| 661 | A73-M-B24 | 1 | 3.38 | 428.3 |
| 662 | A73-M-B26 | 1 | 3.11 | 414.3 |
| 663 | A74-M-B16 | 1 | 2.87 | 453.3 |

TABLE III-continued

| Entry | Compound | HPLC Method | HPLC Rt (min) | [M + H]⁺ |
|---|---|---|---|---|
| 664 | A74-M-B17 | 1 | 2.04 | 377.2 |
| 665 | A75-M-B18 | 1 | 2.95 | 399.3 |
| 666 | A75-M-B19 | 1 | 1.91 | 343.2 |
| 667 | A75-M-B20 | 1 | 2.72 | 407.3 |
| 668 | A75-M-B21 | 1 | 2.75 | 407.3 |
| 669 | A75-M-B22 | 1 | 2.98 | 399.3 |
| 670 | A75-M-B23 | 1 | 2.34 | 359.3 |
| 671 | A75-M-B24 | 1 | 2.68 | 385.3 |
| 672 | A75-M-B25 | 1 | 2.09 | 345.2 |
| 673 | A75-M-B27 | 1 | 1.98 | 343.2 |
| 674 | A76-M-B18 | 1 | 2.69 | 410.3 |
| 675 | A76-M-B19 | 1 | 1.7 | 354.2 |
| 676 | A76-M-B20 | 1 | 2.45 | 418.3 |
| 677 | A76-M-B21 | 1 | 2.5 | 418.3 |
| 678 | A76-M-B22 | 1 | 2.72 | 410.3 |
| 679 | A76-M-B23 | 1 | 2.06 | 370.3 |
| 680 | A76-M-B24 | 1 | 2.4 | 396.3 |
| 681 | A76-M-B25 | 1 | 1.85 | 356.3 |
| 682 | A77-M-B14 | 1 | 2.64 | 421.3 |
| 683 | A77-M-B16 | 1 | 2.9 | 435.3 |
| 684 | A77-M-B18 | 1 | 3.2 | 427.3 |
| 685 | A77-M-B20 | 1 | 2.89 | 435.3 |
| 686 | A77-M-B21 | 1 | 2.92 | 435.3 |
| 687 | A77-M-B27 | 1 | 2.19 | 371.3 |
| 688 | A78-M-B12 | 1 | 2.69 | 442.3 |
| 689 | A78-M-B14 | 1 | 3.16 | 448.3 |
| 690 | A78-M-B15 | 1 | 3.02 | 414.3 |
| 691 | A78-M-B16 | 1 | 3.38 | 462.3 |
| 692 | A78-M-B17 | 1 | 2.57 | 386.3 |
| 693 | A78-M-B18 | 1 | 3.65 | 454.3 |
| 694 | A78-M-B19 | 1 | 2.59 | 398.3 |
| 695 | A78-M-B20 | 1 | 3.38 | 462.3 |
| 696 | A78-M-B21 | 1 | 3.42 | 462.3 |
| 697 | A78-M-B22 | 1 | 3.62 | 454.3 |
| 698 | A78-M-B23 | 1 | 3.07 | 414.3 |
| 699 | A78-M-B24 | 1 | 3.37 | 440.3 |
| 700 | A78-M-B26 | 1 | 3.12 | 426.3 |
| 701 | A78-M-B7 | 1 | 2.51 | 416.3 |
| 702 | A79-M-B14 | 1 | 3.69 | 466.3 |
| 703 | A79-M-B18 | 1 | 4.09 | 472.3 |
| 704 | A79-M-B21 | 1 | 3.9 | 480.3 |
| 705 | A79-M-B22 | 1 | 4.07 | 472.3 |
| 706 | A79-M-B24 | 1 | 3.86 | 458.3 |
| 707 | A79-M-B26 | 1 | 3.65 | 444.3 |
| 708 | A80-M-B14 | 1 | 3.66 | 470.2 |
| 709 | A80-M-B15 | 1 | 3.56 | 436.2 |
| 710 | A80-M-B18 | 1 | 4.06 | 476.3 |
| 711 | A80-M-B19 | 1 | 3.19 | 420.2 |
| 712 | A80-M-B21 | 1 | 3.87 | 484.2 |
| 713 | A80-M-B22 | 1 | 4.04 | 476.3 |
| 714 | A80-M-B24 | 1 | 3.87 | 462.3 |
| 715 | A81-M-B14 | 1 | 3.64 | 466.3 |
| 716 | A81-M-B18 | 1 | 4.06 | 472.3 |
| 717 | A81-M-B19 | 1 | 3.11 | 416.2 |
| 718 | A81-M-B21 | 1 | 3.88 | 480.3 |
| 719 | A81-M-B22 | 1 | 4.06 | 472.3 |
| 720 | A81-M-B24 | 1 | 3.83 | 458.3 |
| 721 | A82-M-B14 | 1 | 3.4 | 446.3 |
| 722 | A82-M-B18 | 1 | 3.86 | 452.4 |
| 723 | A82-M-B19 | 1 | 2.8 | 396.3 |
| 724 | A82-M-B20 | 1 | 3.62 | 460.3 |
| 725 | A82-M-B21 | 1 | 3.66 | 460.3 |
| 726 | A82-M-B22 | 1 | 3.86 | 452.4 |
| 727 | A82-M-B24 | 1 | 3.59 | 438.3 |
| 728 | A83-M-B14 | 1 | 3.45 | 446.3 |
| 729 | A83-M-B18 | 1 | 3.89 | 452.4 |
| 730 | A83-M-B19 | 1 | 2.87 | 396.3 |
| 731 | A83-M-B20 | 1 | 3.65 | 460.3 |
| 732 | A83-M-B22 | 1 | 3.89 | 452.4 |
| 733 | A83-M-B24 | 1 | 3.64 | 438.3 |
| 734 | A84-M-B14 | 1 | 3.03 | 432.3 |
| 735 | A84-M-B18 | 1 | 3.58 | 438.3 |
| 736 | A84-M-B19 | 1 | 2.38 | 382.3 |
| 737 | A84-M-B20 | 1 | 3.27 | 446.3 |
| 738 | A84-M-B21 | 1 | 3.32 | 446.3 |
| 739 | A84-M-B22 | 1 | 3.54 | 438.3 |
| 740 | A85-M-B14 | 1 | 3.56 | 450.3 |
| 741 | A85-M-B17 | 1 | 3.04 | 388.3 |
| 742 | A85-M-B20 | 1 | 3.76 | 464.3 |
| 743 | A85-M-B21 | 1 | 3.79 | 464.3 |
| 744 | A85-M-B22 | 2 | 5.71 | 456.3 |
| 745 | A86-M-B14 | 1 | 3.02 | 410.3 |
| 746 | A86-M-B20 | 1 | 3.27 | 424.3 |
| 747 | A86-M-B21 | 1 | 3.32 | 424.3 |
| 748 | A86-M-B25 | 1 | 2.61 | 362.3 |
| 749 | A87-M-B14 | 1 | 3.33 | 446.3 |
| 750 | A87-M-B20 | 1 | 3.55 | 460.3 |
| 751 | A88-M-B14 | 1 | 3.31 | 454.3 |
| 752 | A88-M-B16 | 1 | 3.49 | 468.3 |
| 753 | A88-M-B17 | 1 | 2.63 | 392.2 |
| 754 | A88-M-B19 | 1 | 2.66 | 404.2 |
| 755 | A88-M-B20 | 1 | 3.53 | 468.3 |
| 756 | A88-M-B21 | 1 | 3.57 | 468.3 |
| 757 | A89-M-B14 | 1 | 2.64 | 422.3 |
| 758 | A89-M-B20 | 1 | 2.91 | 436.3 |
| 759 | A89-M-B21 | 1 | 2.97 | 436.3 |
| 760 | A90-M-B13 | 1 | 1.89 | 349.3 |
| 761 | A90-M-B16 | 1 | 2.56 | 411.3 |
| 762 | A90-M-B20 | 1 | 2.6 | 411.3 |
| 763 | A90-M-B21 | 1 | 2.68 | 411.3 |
| 764 | A91-M-B14 | 1 | 2.4 | 407.3 |
| 765 | A91-M-B16 | 1 | 2.68 | 421.3 |
| 766 | A91-M-B18 | 1 | 2.99 | 413.3 |
| 767 | A91-M-B20 | 1 | 2.65 | 421.3 |
| 768 | A91-M-B21 | 1 | 2.69 | 421.3 |
| 769 | A91-M-B26 | 1 | 2.35 | 385.3 |
| 770 | A92-M-B12 | 1 | 3.15 | 446.3 |
| 771 | A92-M-B14 | 1 | 3.58 | 452.2 |
| 772 | A92-M-B17 | 1 | 3.05 | 390.2 |
| 773 | A92-M-B20 | 1 | 3.78 | 466.3 |
| 774 | A92-M-B21 | 1 | 3.8 | 466.3 |
| 775 | A92-M-B22 | 1 | 3.97 | 458.3 |
| 776 | A92-M-B24 | 1 | 3.78 | 444.3 |
| 777 | A92-M-B26 | 1 | 3.56 | 430.3 |
| 778 | A92-M-B7 | 1 | 2.98 | 420.2 |
| 779 | A93-M-B14 | 1 | 3.41 | 452.2 |
| 780 | A93-M-B16 | 1 | 3.6 | 466.3 |
| 781 | A93-M-B17 | 1 | 2.82 | 390.2 |
| 782 | A93-M-B20 | 1 | 3.63 | 466.3 |
| 783 | A93-M-B21 | 1 | 3.66 | 466.3 |
| 784 | A93-M-B22 | 1 | 3.85 | 458.3 |
| 785 | A93-M-B24 | 1 | 3.63 | 444.3 |
| 786 | A93-M-B26 | 1 | 3.37 | 430.3 |
| 787 | A93-M-B27 | 1 | 2.96 | 402.2 |
| 788 | A93-M-B7 | 1 | 2.76 | 420.2 |
| 789 | A94-M-B14 | 1 | 3.58 | 452.2 |
| 790 | A94-M-B17 | 1 | 3.04 | 390.2 |
| 791 | A94-M-B21 | 1 | 3.81 | 466.3 |
| 792 | A94-M-B24 | 1 | 3.78 | 444.3 |
| 793 | A94-M-B26 | 1 | 3.55 | 430.3 |
| 794 | A95-M-B14 | 1 | 3.16 | 432.3 |
| 795 | A95-M-B20 | 1 | 3.39 | 446.3 |
| 796 | A95-M-B21 | 1 | 3.45 | 446.3 |
| 797 | A95-M-B24 | 1 | 3.37 | 424.3 |
| 798 | A95-M-B26 | 1 | 3.09 | 410.3 |
| 799 | A96-M-B14 | 1 | 3.36 | 432.3 |
| 800 | A96-M-B20 | 1 | 3.58 | 446.3 |
| 801 | A96-M-B21 | 1 | 3.62 | 446.3 |
| 802 | A96-M-B22 | 1 | 3.81 | 438.3 |
| 803 | A96-M-B24 | 1 | 3.57 | 424.3 |
| 804 | A97-M-B12 | 1 | 2.59 | 442.3 |
| 805 | A97-M-B14 | 1 | 3.1 | 448.3 |
| 806 | A97-M-B16 | 1 | 3.26 | 462.3 |
| 807 | A97-M-B17 | 1 | 2.46 | 386.3 |
| 808 | A97-M-B18 | 1 | 3.56 | 454.3 |
| 809 | A97-M-B20 | 1 | 3.29 | 462.3 |
| 810 | A97-M-B22 | 1 | 3.52 | 454.3 |
| 811 | A97-M-B24 | 1 | 3.26 | 440.3 |
| 812 | A97-M-B26 | 1 | 3.02 | 426.3 |
| 813 | A98-M-B14 | 1 | 2.97 | 443.3 |
| 814 | A98-M-B17 | 1 | 2.4 | 381.3 |
| 815 | A98-M-B20 | 1 | 3.2 | 457.3 |
| 816 | A98-M-B22 | 1 | 3.4 | 449.3 |
| 817 | A98-M-B24 | 1 | 3.21 | 435.3 |

TABLE III-continued

| Entry | Compound | HPLC Method | HPLC Rt (min) | [M + H]+ |
|---|---|---|---|---|
| 818 | A98-M-B7 | 1 | 2.35 | 411.3 |
| 819 | A99-M-B14 | 1 | 3.86 | 466.3 |
| 820 | A99-M-B20 | 1 | 3.99 | 480.3 |
| 821 | A99-M-B22 | 1 | 4.17 | 472.3 |
| 822 | A99-M-B24 | 1 | 3.98 | 458.3 |
| 823 | A99-M-B26 | 1 | 3.79 | 444.3 |
| 824 | A100-M-B14 | 1 | 3.65 | 446.3 |
| 825 | A100-M-B22 | 1 | 4.04 | 452.4 |
| 826 | A100-M-B24 | 1 | 3.84 | 438.3 |
| 827 | A100-M-B26 | 1 | 3.62 | 424.3 |
| 828 | A101-M-B14 | 1 | 3.33 | 412.3 |
| 829 | A101-M-B19 | 1 | 2.71 | 362.3 |
| 830 | A101-M-B20 | 1 | 3.54 | 426.3 |
| 831 | A101-M-B21 | 1 | 3.59 | 426.3 |
| 832 | A101-M-B22 | 1 | 3.8 | 418.4 |
| 833 | A102-M-B14 | 1 | 3.29 | 436.3 |
| 834 | A102-M-B17 | 1 | 2.67 | 374.3 |
| 835 | A102-M-B19 | 1 | 2.69 | 386.3 |
| 836 | A102-M-B20 | 1 | 3.51 | 450.3 |
| 837 | A102-M-B21 | 1 | 3.55 | 450.3 |
| 838 | A102-M-B22 | 1 | 3.74 | 442.3 |
| 839 | A103-M-B14 | 1 | 2.95 | 398.3 |
| 840 | A103-M-B20 | 1 | 3.21 | 412.3 |
| 841 | A103-M-B21 | 1 | 3.27 | 412.3 |
| 842 | A103-M-B22 | 1 | 3.5 | 404.4 |
| 843 | A104-M-B16 | 1 | 3.36 | 460.3 |
| 844 | A104-M-B22 | 1 | 3.68 | 452.4 |
| 845 | A105-M-B14 | 1 | 3.65 | 446.3 |
| 846 | A105-M-B20 | 1 | 3.83 | 460.3 |
| 847 | A105-M-B21 | 1 | 3.86 | 460.3 |
| 848 | A105-M-B22 | 1 | 4.05 | 452.4 |
| 849 | A106-M-B14 | 1 | 3.64 | 446.3 |
| 850 | A106-M-B16 | 1 | 3.82 | 460.3 |
| 851 | A106-M-B17 | 1 | 3.12 | 384.3 |
| 852 | A106-M-B20 | 1 | 3.85 | 460.3 |
| 853 | A106-M-B21 | 1 | 3.87 | 460.3 |
| 854 | A106-M-B24 | 1 | 3.84 | 438.3 |
| 855 | A106-M-B26 | 1 | 3.63 | 424.3 |
| 856 | A107-M-B14 | 1 | 3.67 | 466.3 |
| 857 | A107-M-B16 | 1 | 3.83 | 480.3 |
| 858 | A107-M-B24 | 1 | 3.91 | 458.3 |
| 859 | A107-M-B26 | 1 | 3.65 | 444.3 |
| 860 | A108-M-B20 | 1 | 3.81 | 437.3 |
| 861 | A108-M-B25 | 1 | 3.28 | 375.3 |
| 862 | A108-M-B27 | 1 | 3.17 | 373.3 |
| 863 | A109-M-B13 | 1 | 2.47 | 407.2 |
| 864 | A109-M-B16 | 1 | 3.12 | 469.2 |
| 865 | A110-M-B14 | 1 | 3.57 | 450.3 |
| 866 | A110-M-B17 | 1 | 3.03 | 388.3 |
| 867 | A110-M-B20 | 1 | 3.76 | 464.3 |
| 868 | A111-M-B14 | 1 | 3.59 | 454.3 |
| 869 | A111-M-B17 | 1 | 3.05 | 392.2 |
| 870 | A111-M-B22 | 1 | 3.99 | 460.3 |
| 871 | A112-M-B16 | 1 | 2.55 | 369.3 |
| 872 | A112-M-B21 | 1 | 2.64 | 369.3 |
| 873 | A113-M-B16 | 1 | 2.66 | 419.3 |
| 874 | A114-M-B16 | 1 | 2.38 | 405.3 |
| 875 | A115-M-B16 | 1 | 2.59 | 419.3 |
| 876 | A116-M-B20 | 1 | 2.39 | 385.3 |
| 877 | A116-M-B21 | 1 | 2.48 | 385.3 |
| 878 | A117-M-B20 | 1 | 2.59 | 428.3 |
| 879 | A118-M-B20 | 1 | 2.69 | 440.3 |
| 880 | A118-M-B21 | 1 | 2.76 | 440.3 |
| 881 | A119-M-B20 | 1 | 2.87 | 398.3 |
| 882 | A120-M-B21 | 1 | 3.32 | 412.3 |
| 883 | A121-M-B21 | 1 | 2.53 | 414.3 |
| 884 | A122-M-B21 | 1 | 2.03 | 433.3 |
| 885 | A122-M-B22 | 1 | 2.21 | 425.3 |
| 886 | A123-M-B25 | 1 | 2.16 | 345.2 |
| 887 | A20-M-B14 | 1 | 3.92 | 394.2 |
| 888 | A20-M-B17 | 1 | 3.41 | 332.2 |
| 889 | A20-M-B19 | 1 | 3.41 | 344.2 |
| 890 | A20-M-B24 | 1 | 4.09 | 386.3 |
| 891 | A20-M-B25 | 1 | 3.63 | 346.2 |
| 892 | A20-M-B26 | 1 | 3.88 | 372.2 |
| 893 | A20-M-B31 | 1 | 3.31 | 332.2 |
| 894 | A20-M-B32 | 1 | 4.07 | 374.3 |
| 895 | A20-M-B33 | 1 | 2.59 | 450.3 |
| 896 | A20-M-B35 | 1 | 3.24 | 318.2 |
| 897 | A20-M-B36 | 1 | 3.93 | 394.2 |
| 898 | A20-M-B39 | 1 | 2.4 | 395.2 |
| 899 | A20-M-B40 | 1 | 3.67 | 384.2 |
| 900 | A20-M-B42 | 1 | 3.39 | 376.2 |
| 901 | A20-M-B56 | 1 | 2.42 | 387.3 |
| 902 | A20-M-B59 | 1 | 2.44 | 401.3 |
| 903 | A33-M-B14 | 4 | 1.172 | 366.1 |
| 904 | A33-M-B22 | 4 | 1.33 | 372.2 |
| 905 | A33-M-B28 | 4 | 0.929 | 360.1 |
| 906 | A33-M-B29 | 4 | 0.645 | 367.1 |
| 907 | A33-M-B30 | 4 | 1.205 | 384.1 |
| 908 | A124-M-B9 | 4 | 0.655 | 341.2 |
| 909 | A125-M-B9 | 4 | 0.74 | 355.2 |
| 910 | A126-M-B9 | 4 | 1.018 | 356.2 |
| 911 | A127-M-B14 | 4 | 1.29 | 378.2 |
| 912 | A127-M-B19 | 1 | 3.06 | 328.2 |
| 913 | A127-M-B22 | 4 | 1.405 | 384.2 |
| 914 | A127-M-B24 | 1 | 3.79 | 370.3 |
| 915 | A127-M-B25 | 1 | 3.28 | 330.3 |
| 916 | A127-M-B26 | 1 | 3.56 | 356.3 |
| 917 | A127-M-B28 | 4 | 1 | 372.2 |
| 918 | A127-M-B29 | 4 | 0.757 | 379.1 |
| 919 | A127-M-B30 | 4 | 1.279 | 396.1 |
| 920 | A127-M-B31 | 1 | 2.95 | 316.2 |
| 921 | A127-M-B32 | 1 | 3.8 | 358.3 |
| 922 | A127-M-B33 | 1 | 2.28 | 434.3 |
| 923 | A127-M-B36 | 1 | 3.63 | 378.3 |
| 924 | A127-M-B37 | 1 | 3.83 | 378.3 |
| 925 | A127-M-B38 | 1 | 2.1 | 401.3 |
| 926 | A127-M-B39 | 1 | 2.06 | 379.2 |
| 927 | A127-M-B40 | 1 | 3.35 | 368.2 |
| 928 | A127-M-B41 | 1 | 2.68 | 399.3 |
| 929 | A127-M-B42 | 1 | 3.04 | 360.3 |
| 930 | A127-M-B43 | 1 | 3.59 | 344.3 |
| 931 | A127-M-B46 | 1 | 3.38 | 344.3 |
| 932 | A127-M-B47 | 1 | 3.6 | 382.2 |
| 933 | A127-M-B48 | 1 | 3.36 | 342.2 |
| 934 | A127-M-B49 | 1 | 2.26 | 397.3 |
| 935 | A127-M-B50 | 1 | 3.12 | 342.3 |
| 936 | A127-M-B51 | 1 | 2.9 | 358.2 |
| 937 | A127-M-B52 | 1 | 3.62 | 364.2 |
| 938 | A127-M-B53 | 1 | 2.12 | 413.3 |
| 939 | A127-M-B54 | 1 | 3.04 | 410.3 |
| 940 | A127-M-B56 | 1 | 2.08 | 371.3 |
| 941 | A127-M-B57 | 1 | 1.74 | 454.4 |
| 942 | A127-M-B58 | 1 | 2.79 | 435.2 |
| 943 | A127-M-B60 | 1 | 2.09 | 359.3 |
| 944 | A127-M-B7 | 1 | 2.96 | 346.2 |
| 945 | A127-M-B9 | 4 | 1.311 | 358.2 |
| 946 | A128-M-B14 | 4 | 1.23 | 378.2 |
| 947 | A128-M-B14 | 1 | 3.56 | 378.3 |
| 948 | A128-M-B17 | 1 | 2.98 | 316.2 |
| 949 | A128-M-B19 | 1 | 2.98 | 328.2 |
| 950 | A128-M-B22 | 4 | 1.401 | 384.2 |
| 951 | A128-M-B25 | 1 | 3.24 | 330.3 |
| 952 | A128-M-B26 | 1 | 3.5 | 356.3 |
| 953 | A128-M-B28 | 4 | 0.952 | 372.2 |
| 954 | A128-M-B29 | 4 | 0.73 | 379.1 |
| 955 | A128-M-B30 | 4 | 1.268 | 396.1 |
| 956 | A128-M-B31 | 1 | 2.9 | 316.2 |
| 957 | A128-M-B32 | 1 | 3.76 | 358.3 |
| 958 | A128-M-B33 | 1 | 2.26 | 434.3 |
| 959 | A128-M-B34 | 1 | 3.23 | 374.2 |
| 960 | A128-M-B35 | 1 | 2.79 | 302.2 |
| 961 | A128-M-B36 | 1 | 3.56 | 378.3 |
| 962 | A128-M-B37 | 1 | 3.77 | 378.3 |
| 963 | A128-M-B38 | 1 | 2.08 | 401.3 |
| 964 | A128-M-B39 | 1 | 2.03 | 379.2 |
| 965 | A128-M-B40 | 1 | 3.29 | 368.2 |
| 966 | A128-M-B41 | 1 | 2.64 | 399.3 |
| 967 | A128-M-B42 | 1 | 2.98 | 360.3 |
| 968 | A128-M-B43 | 1 | 3.54 | 344.3 |
| 969 | A128-M-B45 | 1 | 3.52 | 370.3 |
| 970 | A128-M-B46 | 1 | 3.35 | 344.3 |
| 971 | A128-M-B47 | 1 | 3.51 | 382.2 |

TABLE III-continued

| Entry | Compound | HPLC Method | HPLC Rt (min) | [M + H]+ |
|---|---|---|---|---|
| 972 | A128-M-B48 | 1 | 3.31 | 342.3 |
| 973 | A128-M-B49 | 1 | 2.21 | 397.3 |
| 974 | A128-M-B50 | 1 | 3.08 | 342.3 |
| 975 | A128-M-B51 | 1 | 2.86 | 358.2 |
| 976 | A128-M-B54 | 1 | 3 | 410.3 |
| 977 | A128-M-B55 | 1 | 3.06 | 438.3 |
| 978 | A128-M-B56 | 1 | 2.1 | 371.3 |
| 979 | A128-M-B57 | 1 | 1.75 | 454.4 |
| 980 | A128-M-B58 | 1 | 2.76 | 435.2 |
| 981 | A128-M-B59 | 1 | 2.1 | 385.3 |
| 982 | A128-M-B60 | 1 | 2.08 | 359.3 |
| 983 | A128-M-B7 | 1 | 2.89 | 346.2 |
| 984 | A128-M-B9 | 4 | 1.304 | 358.2 |
| 985 | A129-M-B14 | 4 | 1.242 | 378.2 |
| 986 | A129-M-B22 | 4 | 1.399 | 384.2 |
| 987 | A129-M-B28 | 4 | 0.96 | 372.2 |
| 988 | A129-M-B29 | 4 | 0.752 | 379.1 |
| 989 | A129-M-B30 | 4 | 1.31 | 396.1 |
| 990 | A129-M-B9 | 4 | 1.303 | 358.2 |
| 991 | A130-M-B9 | 4 | 0.984 | 366.2 |
| 992 | A131-M-B9 | 4 | 1.164 | 382.2 |
| 993 | A132-M-B14 | 4 | 1.16 | 404.2 |
| 994 | A132-M-B22 | 4 | 1.309 | 410.2 |
| 995 | A132-M-B28 | 4 | 0.878 | 398.2 |
| 996 | A132-M-B29 | 4 | 0.693 | 405.1 |
| 997 | A132-M-B30 | 4 | 1.24 | 422.1 |
| 998 | A132-M-B9 | 4 | 1.219 | 384.2 |
| 999 | A133-M-B14 | 4 | 1.406 | 428.2 |
| 1000 | A133-M-B22 | 4 | 1.6 | 434.2 |
| 1001 | A133-M-B28 | 4 | 1.158 | 422.2 |
| 1002 | A133-M-B29 | 4 | 0.95 | 429.1 |
| 1003 | A133-M-B30 | 4 | 1.427 | 446.1 |
| 1004 | A133-M-B9 | 4 | 1.473 | 408.2 |
| 1005 | A134-M-B14 | 4 | 1.45 | 444.1 |
| 1006 | A134-M-B22 | 4 | 1.593 | 450.2 |
| 1007 | A134-M-B28 | 4 | 1.206 | 438.2 |
| 1008 | A134-M-B29 | 4 | 1.002 | 445.1 |
| 1009 | A134-M-B30 | 4 | 1.471 | 462.1 |
| 1010 | A134-M-B9 | 4 | 1.516 | 424.2 |
| 1011 | A135-M-B9 | 4 | 1.526 | 424.2 |
| 1012 | A136-M-B9 | 4 | 0.674 | 355.2 |
| 1013 | A137-M-B14 | 4 | 1.314 | 374.2 |
| 1014 | A137-M-B14 | 1 | 3.76 | 374.3 |
| 1015 | A137-M-B22 | 4 | 1.477 | 380.2 |
| 1016 | A137-M-B24 | 1 | 3.93 | 366.3 |
| 1017 | A137-M-B25 | 1 | 3.45 | 326.3 |
| 1018 | A137-M-B26 | 1 | 3.7 | 352.3 |
| 1019 | A137-M-B28 | 4 | 1.08 | 368.2 |
| 1020 | A137-M-B29 | 4 | 0.808 | 375.2 |
| 1021 | A137-M-B30 | 4 | 1.346 | 392.2 |
| 1022 | A137-M-B32 | 1 | 3.95 | 354.3 |
| 1023 | A137-M-B33 | 1 | 2.4 | 430.3 |
| 1024 | A137-M-B34 | 1 | 3.42 | 370.3 |
| 1025 | A137-M-B35 | 1 | 3.01 | 298.2 |
| 1026 | A137-M-B36 | 1 | 3.77 | 374.3 |
| 1027 | A137-M-B39 | 1 | 2.19 | 375.3 |
| 1028 | A137-M-B40 | 1 | 3.49 | 364.3 |
| 1029 | A137-M-B43 | 1 | 3.73 | 340.3 |
| 1030 | A137-M-B48 | 1 | 3.5 | 338.3 |
| 1031 | A137-M-B49 | 1 | 2.4 | 393.3 |
| 1032 | A137-M-B50 | 1 | 3.27 | 338.3 |
| 1033 | A137-M-B52 | 1 | 3.76 | 360.3 |
| 1034 | A137-M-B54 | 1 | 3.19 | 406.3 |
| 1035 | A137-M-B55 | 1 | 3.24 | 434.3 |
| 1036 | A137-M-B56 | 1 | 2.25 | 367.3 |
| 1037 | A137-M-B58 | 1 | 2.93 | 431.3 |
| 1038 | A137-M-B59 | 1 | 2.25 | 381.3 |
| 1039 | A138-M-B14 | 4 | 1.206 | 390.2 |
| 1040 | A138-M-B22 | 4 | 1.43 | 396.2 |
| 1041 | A138-M-B28 | 4 | 0.926 | 384.2 |
| 1042 | A138-M-B29 | 4 | 0.726 | 391.2 |
| 1043 | A138-M-B30 | 4 | 1.23 | 408.2 |
| 1044 | A139-M-B14 | 1 | 3.75 | 396.2 |
| 1045 | A139-M-B17 | 1 | 3.22 | 334.2 |
| 1046 | A139-M-B19 | 1 | 3.23 | 346.2 |
| 1047 | A139-M-B22 | 4 | 1.441 | 402.2 |
| 1048 | A139-M-B24 | 1 | 3.93 | 388.3 |
| 1049 | A139-M-B25 | 1 | 3.46 | 348.2 |
| 1050 | A139-M-B26 | 1 | 3.71 | 374.3 |
| 1051 | A139-M-B28 | 4 | 1.023 | 390.2 |
| 1052 | A139-M-B29 | 4 | 0.822 | 397.1 |
| 1053 | A139-M-B30 | 4 | 1.32 | 414.1 |
| 1054 | A139-M-B31 | 1 | 3.12 | 334.2 |
| 1055 | A139-M-B32 | 1 | 3.91 | 376.3 |
| 1056 | A139-M-B33 | 1 | 2.45 | 452.3 |
| 1057 | A139-M-B35 | 1 | 3.03 | 320.2 |
| 1058 | A139-M-B36 | 1 | 3.77 | 396.2 |
| 1059 | A139-M-B37 | 1 | 3.95 | 396.2 |
| 1060 | A139-M-B38 | 1 | 2.29 | 419.3 |
| 1061 | A139-M-B39 | 1 | 2.23 | 397.2 |
| 1062 | A139-M-B40 | 1 | 3.51 | 386.2 |
| 1063 | A139-M-B41 | 1 | 2.87 | 417.3 |
| 1064 | A139-M-B42 | 1 | 3.21 | 378.3 |
| 1065 | A139-M-B43 | 1 | 3.71 | 362.3 |
| 1066 | A139-M-B45 | 1 | 3.71 | 388.3 |
| 1067 | A139-M-B46 | 1 | 3.53 | 362.3 |
| 1068 | A139-M-B48 | 1 | 3.51 | 360.2 |
| 1069 | A139-M-B49 | 1 | 2.38 | 415.3 |
| 1070 | A139-M-B50 | 1 | 3.29 | 360.2 |
| 1071 | A139-M-B51 | 1 | 3.08 | 376.2 |
| 1072 | A139-M-B52 | 1 | 3.77 | 382.2 |
| 1073 | A139-M-B53 | 1 | 2.3 | 431.3 |
| 1074 | A139-M-B56 | 1 | 2.28 | 389.3 |
| 1075 | A139-M-B57 | 1 | 1.89 | 472.3 |
| 1076 | A139-M-B58 | 1 | 2.96 | 453.2 |
| 1077 | A139-M-B60 | 1 | 2.24 | 377.3 |
| 1078 | A139-M-B7 | 1 | 3.13 | 364.2 |
| 1079 | A140-M-B14 | 4 | 1.36 | 406.2 |
| 1080 | A140-M-B22 | 4 | 1.474 | 412.2 |
| 1081 | A140-M-B28 | 4 | 1.06 | 400.2 |
| 1082 | A140-M-B29 | 4 | 0.846 | 407.1 |
| 1083 | A140-M-B30 | 4 | 1.352 | 424.1 |
| 1084 | A141-M-B14 | 4 | 1.176 | 418.2 |
| 1085 | A141-M-B22 | 4 | 1.321 | 424.2 |
| 1086 | A141-M-B28 | 4 | 0.932 | 412.2 |
| 1087 | A141-M-B29 | 4 | 0.745 | 419.2 |
| 1088 | A141-M-B30 | 4 | 1.206 | 436.2 |
| 1089 | A142-M-B14 | 4 | 1.197 | 418.2 |
| 1090 | A142-M-B22 | 4 | 1.345 | 424.2 |
| 1091 | A142-M-B28 | 4 | 0.933 | 412.2 |
| 1092 | A142-M-B29 | 4 | 0.756 | 419.2 |
| 1093 | A142-M-B30 | 4 | 1.225 | 436.2 |
| 1094 | A143-M-B14 | 4 | 1.45 | 428.2 |
| 1095 | A143-M-B22 | 4 | 1.562 | 434.2 |
| 1096 | A143-M-B28 | 4 | 1.178 | 422.2 |
| 1097 | A143-M-B29 | 4 | 0.977 | 429.1 |
| 1098 | A143-M-B30 | 4 | 1.443 | 446.1 |
| 1099 | A144-M-B14 | 4 | 0.649 | 350.2 |
| 1100 | A144-M-B22 | 4 | 0.83 | 356.2 |
| 1101 | A144-M-B30 | 4 | 0.686 | 368.1 |
| 1102 | A145-M-B14 | 4 | 1.52 | 477.1 |
| 1103 | A145-M-B22 | 4 | 1.594 | 483.1 |
| 1104 | A146-M-B14 | 1 | 3.6 | 408.3 |
| 1105 | A146-M-B17 | 1 | 3.06 | 346.2 |
| 1106 | A146-M-B19 | 1 | 3.07 | 358.2 |
| 1107 | A146-M-B24 | 1 | 3.77 | 400.3 |
| 1108 | A146-M-B25 | 1 | 3.29 | 360.3 |
| 1109 | A146-M-B26 | 1 | 3.55 | 386.3 |
| 1110 | A146-M-B31 | 1 | 2.97 | 346.2 |
| 1111 | A146-M-B32 | 1 | 3.77 | 388.3 |
| 1112 | A146-M-B33 | 1 | 2.32 | 464.3 |
| 1113 | A146-M-B34 | 1 | 3.27 | 404.2 |
| 1114 | A146-M-B35 | 1 | 2.88 | 332.2 |
| 1115 | A146-M-B36 | 1 | 3.64 | 408.3 |
| 1116 | A146-M-B37 | 1 | 3.83 | 408.3 |
| 1117 | A146-M-B38 | 1 | 2.24 | 431.3 |
| 1118 | A146-M-B39 | 1 | 2.17 | 409.3 |
| 1119 | A146-M-B40 | 1 | 3.34 | 398.2 |
| 1120 | A146-M-B41 | 1 | 2.73 | 429.2 |
| 1121 | A146-M-B42 | 1 | 3.05 | 390.3 |
| 1122 | A146-M-B43 | 1 | 3.57 | 374.3 |
| 1123 | A146-M-B44 | 1 | 2.28 | 415.3 |
| 1124 | A146-M-B45 | 1 | 3.56 | 400.3 |
| 1125 | A146-M-B46 | 1 | 3.38 | 374.3 |

TABLE III-continued

| Entry | Compound | HPLC Method | HPLC Rt (min) | [M + H]+ |
|---|---|---|---|---|
| 1126 | A146-M-B47 | 1 | 3.58 | 412.3 |
| 1127 | A146-M-B48 | 1 | 3.34 | 372.3 |
| 1128 | A146-M-B49 | 1 | 2.33 | 427.3 |
| 1129 | A146-M-B50 | 1 | 3.13 | 372.3 |
| 1130 | A146-M-B51 | 1 | 2.92 | 388.3 |
| 1131 | A146-M-B52 | 1 | 3.63 | 394.2 |
| 1132 | A146-M-B53 | 1 | 2.19 | 443.3 |
| 1133 | A146-M-B54 | 1 | 3.04 | 440.3 |
| 1134 | A146-M-B55 | 1 | 3.11 | 468.3 |
| 1135 | A146-M-B58 | 1 | 2.84 | 465.3 |
| 1136 | A146-M-B7 | 1 | 2.97 | 376.3 |
| 1137 | A147-M-B14 | 1 | 3.76 | 374.3 |
| 1138 | A147-M-B17 | 1 | 3.2 | 312.3 |
| 1139 | A147-M-B24 | 1 | 3.93 | 366.3 |
| 1140 | A147-M-B25 | 1 | 3.46 | 326.3 |
| 1141 | A147-M-B26 | 1 | 3.71 | 352.3 |
| 1142 | A147-M-B31 | 1 | 3.12 | 312.3 |
| 1143 | A147-M-B32 | 1 | 3.95 | 354.3 |
| 1144 | A147-M-B33 | 1 | 2.42 | 430.3 |
| 1145 | A147-M-B34 | 1 | 3.43 | 370.3 |
| 1146 | A147-M-B36 | 1 | 3.76 | 374.3 |
| 1147 | A147-M-B37 | 1 | 3.96 | 374.3 |
| 1148 | A147-M-B39 | 1 | 2.24 | 375.3 |
| 1149 | A147-M-B40 | 1 | 3.5 | 364.3 |
| 1150 | A147-M-B41 | 1 | 2.86 | 395.3 |
| 1151 | A147-M-B42 | 1 | 3.19 | 356.3 |
| 1152 | A147-M-B43 | 1 | 3.75 | 340.3 |
| 1153 | A147-M-B45 | 1 | 3.73 | 366.3 |
| 1154 | A147-M-B46 | 1 | 3.55 | 340.3 |
| 1155 | A147-M-B47 | 1 | 3.74 | 378.3 |
| 1156 | A147-M-B48 | 1 | 3.52 | 338.3 |
| 1157 | A147-M-B50 | 1 | 3.29 | 338.3 |
| 1158 | A147-M-B51 | 1 | 3.08 | 354.3 |
| 1159 | A147-M-B52 | 1 | 3.76 | 360.3 |
| 1160 | A147-M-B54 | 1 | 3.19 | 406.3 |
| 1161 | A147-M-B58 | 1 | 2.95 | 431.3 |
| 1162 | A147-M-B7 | 1 | 3.12 | 342.3 |
| 1163 | A148-M-B14 | 1 | 3.57 | 408.3 |
| 1164 | A148-M-B17 | 1 | 3.01 | 346.2 |
| 1165 | A148-M-B19 | 1 | 3.03 | 358.2 |
| 1166 | A148-M-B24 | 1 | 3.72 | 400.3 |
| 1167 | A148-M-B25 | 1 | 3.24 | 360.3 |
| 1168 | A148-M-B26 | 1 | 3.51 | 386.3 |
| 1169 | A148-M-B31 | 1 | 2.93 | 346.2 |
| 1170 | A148-M-B32 | 1 | 3.74 | 388.3 |
| 1171 | A148-M-B33 | 1 | 2.3 | 464.3 |
| 1172 | A148-M-B34 | 1 | 3.23 | 404.2 |
| 1173 | A148-M-B35 | 1 | 2.85 | 332.2 |
| 1174 | A148-M-B36 | 1 | 3.59 | 408.3 |
| 1175 | A148-M-B37 | 1 | 3.78 | 408.3 |
| 1176 | A148-M-B39 | 1 | 2.13 | 409.3 |
| 1177 | A148-M-B40 | 1 | 3.3 | 398.2 |
| 1178 | A148-M-B41 | 1 | 2.69 | 429.3 |
| 1179 | A148-M-B42 | 1 | 3.02 | 390.3 |
| 1180 | A148-M-B43 | 1 | 3.52 | 374.3 |
| 1181 | A148-M-B45 | 1 | 3.52 | 400.3 |
| 1182 | A148-M-B46 | 1 | 3.35 | 374.3 |
| 1183 | A148-M-B47 | 1 | 3.54 | 412.3 |
| 1184 | A148-M-B48 | 1 | 3.31 | 372.3 |
| 1185 | A148-M-B50 | 1 | 3.11 | 372.3 |
| 1186 | A148-M-B51 | 1 | 2.9 | 388.3 |
| 1187 | A148-M-B52 | 1 | 3.59 | 394.2 |
| 1188 | A148-M-B53 | 1 | 2.17 | 443.3 |
| 1189 | A148-M-B54 | 1 | 3.01 | 440.3 |
| 1190 | A148-M-B55 | 1 | 3.07 | 468.3 |
| 1191 | A148-M-B56 | 1 | 2.2 | 401.3 |
| 1192 | A148-M-B58 | 1 | 2.8 | 465.3 |
| 1193 | A148-M-B7 | 1 | 2.94 | 376.3 |
| 1194 | A149-M-B14 | 1 | 3.83 | 396.2 |
| 1195 | A149-M-B17 | 1 | 3.3 | 334.2 |
| 1196 | A149-M-B19 | 1 | 3.3 | 346.2 |
| 1197 | A149-M-B24 | 1 | 3.99 | 388.3 |
| 1198 | A149-M-B25 | 1 | 3.53 | 348.2 |
| 1199 | A149-M-B26 | 1 | 3.79 | 374.3 |
| 1200 | A149-M-B31 | 1 | 3.2 | 334.2 |
| 1201 | A149-M-B33 | 1 | 2.49 | 452.3 |
| 1202 | A149-M-B34 | 1 | 3.49 | 392.2 |
| 1203 | A149-M-B35 | 1 | 3.09 | 320.2 |
| 1204 | A149-M-B36 | 1 | 3.73 | 396.2 |
| 1205 | A149-M-B38 | 1 | 2.32 | 419.3 |
| 1206 | A149-M-B39 | 1 | 2.29 | 397.2 |
| 1207 | A149-M-B40 | 1 | 3.58 | 386.2 |
| 1208 | A149-M-B41 | 1 | 2.93 | 417.3 |
| 1209 | A149-M-B42 | 1 | 3.29 | 378.3 |
| 1210 | A149-M-B43 | 1 | 3.81 | 362.3 |
| 1211 | A149-M-B44 | 1 | 2.37 | 403.3 |
| 1212 | A149-M-B45 | 1 | 3.78 | 388.3 |
| 1213 | A149-M-B46 | 1 | 3.58 | 362.3 |
| 1214 | A149-M-B47 | 1 | 3.81 | 400.2 |
| 1215 | A149-M-B48 | 1 | 3.59 | 360.2 |
| 1216 | A149-M-B49 | 1 | 2.44 | 415.3 |
| 1217 | A149-M-B50 | 1 | 3.36 | 360.2 |
| 1218 | A149-M-B51 | 1 | 3.15 | 376.2 |
| 1219 | A149-M-B52 | 1 | 3.83 | 382.2 |
| 1220 | A149-M-B53 | 1 | 2.29 | 431.3 |
| 1221 | A149-M-B54 | 1 | 3.26 | 428.3 |
| 1222 | A149-M-B55 | 1 | 3.34 | 456.3 |
| 1223 | A149-M-B56 | 1 | 2.32 | 389.3 |
| 1224 | A149-M-B57 | 1 | 1.92 | 472.3 |
| 1225 | A149-M-B58 | 1 | 3.02 | 453.2 |
| 1226 | A149-M-B60 | 1 | 2.27 | 377.3 |
| 1227 | A150-M-B14 | 1 | 3.88 | 394.2 |
| 1228 | A150-M-B17 | 1 | 3.38 | 332.2 |
| 1229 | A150-M-B19 | 1 | 3.38 | 344.2 |
| 1230 | A150-M-B24 | 1 | 4.05 | 386.3 |
| 1231 | A150-M-B25 | 1 | 3.6 | 346.2 |
| 1232 | A150-M-B26 | 1 | 3.83 | 372.2 |
| 1233 | A150-M-B31 | 1 | 3.29 | 332.2 |
| 1234 | A150-M-B32 | 1 | 4.04 | 374.3 |
| 1235 | A150-M-B33 | 1 | 2.59 | 450.3 |
| 1236 | A150-M-B35 | 1 | 3.2 | 318.2 |
| 1237 | A150-M-B36 | 1 | 3.89 | 394.2 |
| 1238 | A150-M-B37 | 1 | 4.06 | 394.2 |
| 1239 | A150-M-B38 | 1 | 2.39 | 417.3 |
| 1240 | A150-M-B39 | 1 | 2.35 | 395.2 |
| 1241 | A150-M-B40 | 1 | 3.65 | 384.2 |
| 1242 | A150-M-B41 | 1 | 3.04 | 415.2 |
| 1243 | A150-M-B42 | 1 | 3.35 | 376.2 |
| 1244 | A150-M-B43 | 1 | 3.86 | 360.2 |
| 1245 | A150-M-B45 | 1 | 3.85 | 386.3 |
| 1246 | A150-M-B46 | 1 | 3.68 | 360.2 |
| 1247 | A150-M-B48 | 1 | 3.65 | 358.2 |
| 1248 | A150-M-B49 | 1 | 2.51 | 413.3 |
| 1249 | A150-M-B50 | 1 | 3.43 | 358.2 |
| 1250 | A150-M-B51 | 1 | 3.23 | 374.2 |
| 1251 | A150-M-B52 | 1 | 3.89 | 380.2 |
| 1252 | A150-M-B53 | 1 | 2.38 | 429.3 |
| 1253 | A150-M-B54 | 1 | 3.34 | 426.3 |
| 1254 | A150-M-B55 | 1 | 3.39 | 454.3 |
| 1255 | A150-M-B56 | 1 | 2.44 | 387.3 |
| 1256 | A150-M-B57 | 1 | 1.98 | 470.3 |
| 1257 | A150-M-B58 | 1 | 3.11 | 451.2 |
| 1258 | A150-M-B59 | 1 | 2.41 | 401.3 |
| 1259 | A150-M-B7 | 1 | 3.28 | 362.2 |
| 1260 | A151-M-B14 | 1 | 3.72 | 396.2 |
| 1261 | A151-M-B17 | 1 | 3.18 | 334.2 |
| 1262 | A151-M-B19 | 1 | 3.18 | 346.2 |
| 1263 | A151-M-B24 | 1 | 3.89 | 388.3 |
| 1264 | A151-M-B25 | 1 | 3.42 | 348.2 |
| 1265 | A151-M-B26 | 1 | 3.68 | 374.3 |
| 1266 | A151-M-B31 | 1 | 3.09 | 334.2 |
| 1267 | A151-M-B32 | 1 | 3.9 | 376.3 |
| 1268 | A151-M-B33 | 1 | 2.41 | 452.3 |
| 1269 | A151-M-B35 | 1 | 2.99 | 320.2 |
| 1270 | A151-M-B36 | 1 | 3.84 | 396.2 |
| 1271 | A151-M-B37 | 1 | 3.91 | 396.2 |
| 1272 | A151-M-B38 | 1 | 2.23 | 419.3 |
| 1273 | A151-M-B39 | 1 | 2.2 | 397.2 |
| 1274 | A151-M-B41 | 1 | 2.83 | 417.3 |
| 1275 | A151-M-B42 | 1 | 3.17 | 378.3 |
| 1276 | A151-M-B43 | 1 | 3.72 | 362.3 |
| 1277 | A151-M-B45 | 1 | 3.69 | 388.3 |
| 1278 | A151-M-B46 | 1 | 3.51 | 362.3 |
| 1279 | A151-M-B48 | 1 | 3.48 | 360.2 |

TABLE III-continued

| Entry | Compound | HPLC Method | HPLC Rt (min) | [M + H]+ |
|---|---|---|---|---|
| 1280 | A151-M-B49 | 1 | 2.34 | 415.3 |
| 1281 | A151-M-B50 | 1 | 3.25 | 360.2 |
| 1282 | A151-M-B51 | 1 | 3.05 | 376.2 |
| 1283 | A151-M-B52 | 1 | 3.74 | 382.2 |
| 1284 | A151-M-B53 | 1 | 2.23 | 431.3 |
| 1285 | A151-M-B54 | 1 | 3.16 | 428.3 |
| 1286 | A151-M-B56 | 1 | 2.24 | 389.3 |
| 1287 | A151-M-B57 | 1 | 1.86 | 472.3 |
| 1288 | A151-M-B58 | 1 | 2.93 | 453.2 |
| 1289 | A151-M-B59 | 1 | 2.24 | 403.3 |
| 1290 | A151-M-B60 | 1 | 2.21 | 377.3 |
| 1291 | A151-M-B7 | 1 | 3.07 | 364.2 |
| 1292 | A152-M-B14 | 1 | 3.95 | 352.3 |
| 1293 | A152-M-B17 | 1 | 3.42 | 290.3 |
| 1294 | A152-M-B19 | 1 | 3.43 | 302.3 |
| 1295 | A152-M-B24 | 1 | 4.12 | 344.3 |
| 1296 | A152-M-B25 | 1 | 3.66 | 304.3 |
| 1297 | A152-M-B26 | 1 | 3.92 | 330.3 |
| 1298 | A152-M-B31 | 1 | 3.32 | 290.3 |
| 1299 | A152-M-B32 | 1 | 4.13 | 332.3 |
| 1300 | A152-M-B33 | 1 | 2.69 | 408.3 |
| 1301 | A152-M-B34 | 1 | 3.63 | 348.3 |
| 1302 | A152-M-B35 | 1 | 3.23 | 276.3 |
| 1303 | A152-M-B36 | 1 | 3.95 | 352.3 |
| 1304 | A152-M-B37 | 1 | 4.15 | 352.3 |
| 1305 | A152-M-B38 | 1 | 2.42 | 375.3 |
| 1306 | A152-M-B39 | 1 | 2.49 | 353.3 |
| 1307 | A152-M-B40 | 1 | 3.69 | 342.3 |
| 1308 | A152-M-B41 | 1 | 3.04 | 373.3 |
| 1309 | A152-M-B42 | 1 | 3.4 | 334.3 |
| 1310 | A152-M-B43 | 1 | 3.95 | 318.3 |
| 1311 | A152-M-B45 | 1 | 3.91 | 344.3 |
| 1312 | A152-M-B46 | 1 | 3.74 | 318.3 |
| 1313 | A152-M-B47 | 1 | 3.9 | 356.3 |
| 1314 | A152-M-B48 | 1 | 3.72 | 316.3 |
| 1315 | A152-M-B49 | 1 | 2.52 | 371.3 |
| 1316 | A152-M-B50 | 1 | 3.49 | 316.3 |
| 1317 | A152-M-B51 | 1 | 3.28 | 332.3 |
| 1318 | A152-M-B52 | 1 | 3.96 | 338.3 |
| 1319 | A152-M-B53 | 1 | 2.46 | 387.4 |
| 1320 | A152-M-B54 | 1 | 3.38 | 384.3 |
| 1321 | A152-M-B55 | 1 | 3.44 | 412.4 |
| 1322 | A152-M-B56 | 1 | 2.42 | 345.3 |
| 1323 | A152-M-B57 | 1 | 1.99 | 428.4 |
| 1324 | A152-M-B58 | 1 | 3.14 | 409.3 |
| 1325 | A152-M-B7 | 1 | 3.33 | 320.3 |
| 1326 | A153-M-B48 | 1 | 3.64 | 350.3 |
| 1327 | A154-M-B14 | 1 | 3.34 | 324.3 |
| 1328 | A154-M-B17 | 1 | 2.58 | 262.2 |
| 1329 | A154-M-B19 | 1 | 2.6 | 274.2 |
| 1330 | A154-M-B24 | 1 | 3.54 | 316.3 |
| 1331 | A154-M-B25 | 1 | 2.9 | 276.3 |
| 1332 | A154-M-B26 | 1 | 3.25 | 302.3 |
| 1333 | A154-M-B31 | 1 | 2.46 | 262.2 |
| 1334 | A154-M-B32 | 1 | 3.53 | 304.3 |
| 1335 | A154-M-B33 | 1 | 2 | 380.3 |
| 1336 | A154-M-B34 | 1 | 2.88 | 320.2 |
| 1337 | A154-M-B35 | 1 | 2.32 | 248.2 |
| 1338 | A154-M-B36 | 1 | 3.29 | 324.3 |
| 1339 | A154-M-B42 | 1 | 2.63 | 306.3 |
| 1340 | A154-M-B43 | 1 | 3.29 | 290.3 |
| 1341 | A154-M-B45 | 1 | 3.27 | 316.3 |
| 1342 | A154-M-B47 | 1 | 3.25 | 328.3 |
| 1343 | A154-M-B48 | 1 | 2.99 | 288.3 |
| 1344 | A154-M-B49 | 1 | 1.85 | 343.3 |
| 1345 | A154-M-B51 | 1 | 2.45 | 304.3 |
| 1346 | A154-M-B52 | 1 | 3.32 | 310.2 |
| 1347 | A154-M-B53 | 1 | 1.83 | 359.3 |
| 1348 | A154-M-B54 | 1 | 2.65 | 355.2 |
| 1349 | A154-M-B55 | 1 | 2.73 | 384.3 |
| 1350 | A154-M-B58 | 1 | 2.38 | 381.3 |
| 1351 | A154-M-B7 | 1 | 2.49 | 292.3 |
| 1352 | A155-M-B17 | 1 | 2.03 | 323.2 |
| 1353 | A155-M-B19 | 1 | 2.05 | 335.2 |
| 1354 | A155-M-B25 | 1 | 2.28 | 337.3 |
| 1355 | A155-M-B31 | 1 | 2 | 323.2 |
| 1356 | A155-M-B32 | 1 | 2.9 | 365.3 |
| 1357 | A155-M-B33 | 1 | 1.86 | 441.3 |
| 1358 | A155-M-B35 | 1 | 1.87 | 309.2 |
| 1359 | A155-M-B36 | 1 | 2.71 | 385.3 |
| 1360 | A155-M-B39 | 1 | 1.72 | 386.3 |
| 1361 | A155-M-B40 | 1 | 2.37 | 375.2 |
| 1362 | A155-M-B43 | 1 | 2.61 | 351.3 |
| 1363 | A155-M-B45 | 1 | 2.66 | 377.3 |
| 1364 | A155-M-B53 | 1 | 1.74 | 420.3 |
| 1365 | A155-M-B7 | 1 | 2.02 | 353.3 |
| 1366 | A156-M-B24 | 1 | 3.19 | 403.3 |
| 1367 | A156-M-B34 | 1 | 2.59 | 407.2 |
| 1368 | A156-M-B37 | 1 | 3.23 | 411.3 |
| 1369 | A156-M-B45 | 1 | 2.96 | 403.3 |
| 1370 | A156-M-B49 | 1 | 2.01 | 430.3 |
| 1371 | A156-M-B51 | 1 | 2.21 | 391.3 |
| 1372 | A156-M-B52 | 1 | 2.94 | 397.3 |
| 1373 | A156-M-B54 | 1 | 2.4 | 443.3 |

When R1 is a substituent with a chiral center the compounds obtained were mixture of diastereoisomers and they were separated by preparative HPLC.

When the diastereoisomers are resolved, the chirality is to be intended on the 3,4-dihydro-2H-pyrrolo[1,2-a]pyrazin-1-one scaffold.

Working in a parallel manner, the following compounds were prepared:

| Entry | Compound | 1H NMR (400 MHz, DMSO-d6) | HPLC Method | HPLC r.t. min. | [M + H]+ |
|---|---|---|---|---|---|
| 1374 | A157-M-B65 isomer S | δ = 8.50 (d, J = 8.5 Hz, 1H), 8.09 (d, J = 5.4 Hz, 1H), 7.83 (br. s., 1H), 7.44 (d, J = 1.7 Hz, 1H), 7.28 (s, 1H), 5.08-5.17 (m, 1H), 4.61-4.75 (m, 1H), 3.73 (dd, J = 13.1, 4.0 Hz, 1H), 3.36-3.46 (m, 1H), 3.10-3.18 (m, 1H), 2.90-3.04 (m, 1H), 2.68-2.84 (m, 2H). | 4 | 1.196 | 408.2 |
| 1375 | A157-M-B65 isomer R | δ = 8.61 (d, J = 8.5 Hz, 1H), 8.11 (d, J = 5.4 Hz, 1H), 7.68 (d, J = 1.7 Hz, 1H), 5.11 (td, J = 8.9, 4.6 Hz, 1H), 4.63-4.72 (m, 1H), 2.78 (d, J = 6.7 Hz, 2H) | 4 | 1.224 | 408.2 |
| 1376 | A133-M-B61 isomer R | | 4 | 1.373 | 464.2 |
| 1377 | A127-M-B61 isomer R | | 4 | 1.332 | 414.2 |

-continued

| Entry | Compound | ¹H NMR (400 MHz, DMSO-d₆) | HPLC Method | HPLC r.t. min. | [M + H]⁺ |
|---|---|---|---|---|---|
| 1378 | A157-M-B161 isomer R | 8.41-8.60 (m, 1H), 6.90-8.36 (m, 5H), 4.71 (dd, J = 33.3, 3.3 Hz, 2H), 3.56-3.82 (m, 1H), 2.61-2.82 (m, 2H), 1.37-1.75 (m, 2H), 0.80-1.23 (m, 10H) | 4 | 1.052 | 415.2 |
| 1379 | A158-M-B61 isomer R | | 4 | 1.238 | 432.2 |
| 1380 | A133-M-B61 isomer S | 7.54 (t, J = 7.7 Hz, 1H), 7.45 (d, J = 1.8 Hz, 1H), 7.16 (d, J = 1.7 Hz, 1H), 4.69 (sxt, J = 4.2 Hz, 1H), 4.49 (br. s., 1H), 3.72 (dd, J = 13.0, 4.1 Hz, 1H), 3.59 (dq, J = 8.9, 5.8 Hz, 1H), 2.82 (dd, J = 14.9, 8.7 Hz, 1H), 2.57 (dd, J = 14.5, 5.4 Hz, 1H) | 4 | 1.375 | 464.2 |
| 1381 | A127-M-B61 isomer S | 7.68 (d, J = 3.4 Hz, 1H), 7.63 (d, J = 9.2 Hz, 1H), 7.28-7.42 (m, 4H), 7.09 (d, J = 1.8 Hz, 1H), 6.90-6.99 (m, 1H), 4.61-4.72 (m, 1H), 4.50 (t, J = 5.4 Hz, 1H), 3.69 (ddd, J = 13.0, 4.2, 1.2 Hz, 1H), 3.60 (dq, J = 9.2, 5.8 Hz, 1H), 2.79 (dd, J = 14.6, 8.4 Hz, 1H), 2.58 (dd, J = 14.8, 5.8 Hz, 1H) | 4 | 1.363 | 414.2 |
| 1382 | A133-M-B62 isomer R | 7.60 (d, J = 1.7 Hz, 1H), 7.17 (d, J = 1.8 Hz, 1H), 4.89 (dt, J = 7.9, 6.3 Hz, 1H), 4.73-4.95 (m, 1H), 4.59-4.69 (m, 1H), 2.83 (dd, J = 14.8, 6.5 Hz, 1H), 2.74 (dd, J = 14.9, 7.2 Hz, 1H) | 4 | 1.426 | 458.2 |
| 1383 | A127-M-B62 isomer R | 8.49 (d, J = 8.3 Hz, 1H), 7.47 (d, J = 1.8 Hz, 1H), 7.08 (d, J = 1.8 Hz, 1H), 6.91-7.00 (m, 1H), 4.82-4.94 (m, 1H), 4.62 (dd, J = 9.5, 2.8 Hz, 1H), 3.57-3.66 (m, 1H), 3.50 (d, J = 6.0 Hz, 2H), 2.68-2.83 (m, 2H) | 4 | 1.092 | 408.2 |
| 1384 | A157-M-B62 isomer R | 8.51 (d, J = 8.3 Hz, 1H), 8.11 (d, J = 5.4 Hz, 1H), 7.72 (d, J = 1.8 Hz, 1H), 7.18-7.27 (m, 1H), 4.84-4.93 (m, 1H), 4.61-4.72 (m, 1H), 3.64 (d, J = 5.2 Hz, 1H), 3.34 (br. s., 1H), 2.69-2.87 (m, 2H) | 4 | 409.2 | 1.003 |
| 1385 | A158-M-B62 isomer R | 8.45 (d, J = 8.2 Hz, 1H), 7.76 (br. s., 1H), 7.55 (ddd, J = 9.8, 6.3, 3.2 Hz, 1H), 7.45-7.50 (m, 1H), 7.26-7.34 (m, 5H), 7.18-7.25 (m, 1H), 7.13-7.16 (m, 1H), 6.99-7.08 (m, 1H), 4.82-4.90 (m, 1H), 4.79 (br. s., 1H), 4.68 (s, 1H), 3.65 (dd, J = 9.0, 1.8 Hz, 1H), 3.50 (br. s., 2H), 3.37 (d, J = 2.3 Hz, 9H), 2.68-2.85 (m, 2H) | 4 | 1.109 | 426.2 |
| 1386 | A133-M-B62 isomer S | 8.41 (d, J = 8.3 Hz, 1H), 7.41 (d, J = 1.8 Hz, 1H), 7.15-7.18 (m, 1H), 4.79-4.90 (m, 2H), 4.66 (br. s., 1H), 3.68 (d, J = 1.2 Hz, 1H), 3.45-3.61 (m, 1H), 3.34-3.43 (m, 1H), 2.79-2.88 (m, 1H), 2.70 (dd, J = 15.0, 6.8 Hz, 1H) | 4 | 1.332 | 458.2 |
| 1387 | A127-M-B62 isomer S | 8.43 (d, J = 8.3 Hz, 1H), 7.08 (d, J = 1.8 Hz, 1H), 7.03-7.43 (m, 11H), 6.93-7.01 (m, J = 5.1, 4.0, 0.9, 0.9, 0.9 Hz, 1H), 4.88 (q, J = 6.0 Hz, 1H), 4.64 (q, J = 3.3 Hz, 1H), 3.62-3.71 (m, 2H), 3.55 (dd, J = 7.4, 5.5 Hz, 2H), 3.34 (br. s., 2H), 2.65-2.73 (m, 1H) | 4 | 1.121 | 408.2 |
| 1388 | A133-M-B63 Unresolved mixture of diast. | 7.85 (br. s., 1H), 7.65 (br. s., 2H), 7.49 (s, 2H), 7.36 (br. s., 2H), 7.17 (s, 2H), 4.75 (br. s., 1H), 2.18 (s, 1H), 2.07 (s, 1H), 1.96 (s, 1H), 1.75 (s, 1H), 1.63 (s, 7H), 1.23 (br. s., 2H), 0.14-0.34 (m, 2H) | 4 | 1.173 | 497.2 |

| Entry | Compound | ¹H NMR (400 MHz, DMSO-d₆) | HPLC Method | HPLC r.t. min. | [M + H]⁺ |
|---|---|---|---|---|---|
| 1389 | A127-M-B63 unresolved mixture of diast. | 7.59 (d, J = 1.1 Hz, 1H), 7.49 (s, 1H), 7.40 (br. s., 2H), 5.44-6.15 (m, J = 155.3 Hz, 1H), 4.33-5.20 (m, 1H), 4.17 (dd, J = 13.4, 11.8 Hz, 1H), 3.67-3.94 (m, 1H), 2.80 (d, J = 16.4 Hz, 1H), 0.15-0.35 (m, 1H) | 4 | 1.02 | 447.2 |
| 1390 | A157-M-B63 unresolved mixture of diast. | | 4 | 0.782 | 448.2 |
| 1391 | A158-M-B63 P26 unresolved mixture of diast. | 7.13-7.40 (m, 1H), 3.28-3.58 (m, 16H), 3.08-3.28 (m, 1H), 2.41-2.60 (m, 5H) | 4 | 1.031 | 465.2 |
| 1392 | A133-M-B64 isomer R | 7.96 (s, 1H), 7.36-7.90 (m, 1H), 7.12-7.31 (m, 1H), 7.09-7.39 (m, 1H), 4.54 (s, 1H), 3.95 (d, J = 4.9 Hz, 1H), 3.53 (br. s., 1H), 3.33 (s, 13H), 3.15-3.41 (m, 1H), 3.08-3.29 (m, 1H), 2.52-2.90 (m, 1H), 2.41-2.62 (m, 4H) | 4 | 1.44 | 472.2 |
| 1393 | A127-M-B64 isomer R | 8.00 (d, J = 8.4 Hz, 1H), 7.65 (br. s., 1H), 7.39-7.41 (m, 1H), 7.24-7.30 (m, 2H), 7.18-7.22 (m, 2H), 7.08 (d, J = 1.8 Hz, 1H), 6.92-7.00 (m, 1H), 4.53 (s, 1H), 3.93 (br. s., 1H), 3.51 (s, 3H), 2.53-2.93 (m, 4H) | 4 | 1.148 | 422.2 |
| 1394 | A157-M-B64 isomer R | 8.10 (d, J = 5.4 Hz, 1H), 7.94 (d, J = 8.5 Hz, 1H), 7.73 (br. s., 1H), 7.63 (d, J = 1.7 Hz, 1H), 7.44-7.54 (m, 1H), 7.27 (d, J = 1.8 Hz, 1H), 4.56 (br. s., 1H), 3.92 (br. s., 1H), 3.49-3.60 (m, 1H), 3.26-3.38 (m, 1H), 3.23 (br. s., 1H), 3.16 (s, 1H), 2.82 (s, 1H), 2.65 (s, 1H), 2.48-2.56 (m, 4H) | 4 | 0.92 | 423.2 |
| 1395 | A158-M-B64 isomer S | 7.94 (d, J = 8.4 Hz, 1H), 7.56 (d, J = 1.8 Hz, 1H), 7.15-7.16 (m, 1H), 7.14-7.20 (m, 2H), 7.09-7.13 (m, 2H), 7.03-7.08 (m, 1H), 4.77 (t, J = 5.5 Hz, 1H), 4.56 (br. s., 1H), 3.87-3.99 (m, 1H), 3.56-3.63 (m, 1H), 2.54-2.80 (m, 4H) | 4 | 1.331 | 472.2 |
| 1396 | A127-M-B64 isomer S | 6.91-7.00 (m, 1H), 4.50-4.59 (m, J = 7.1, 3.4, 3.4 Hz, 1H), 3.89-3.99 (m, J = 5.9 Hz, 1H), 3.53-3.63 (m, J = 13.6, 3.2 Hz, 1H), 2.76 (dd, J = 13.5, 5.7 Hz, 1H), 2.62-2.70 (m, 1H), 2.52-2.62 (m, 2H) | 4 | 1.181 | 422.2 |
| 1397 | A133-M-B65 isomer S | 8.62 (d, J = 8.5 Hz, 1H), 8.49 (d, J = 8.4 Hz, 1H), 7.81-8.00 (m, 2H), 7.75 (d, J = 7.9 Hz, 2H), 5.00-5.18 (m, J = 2.7 Hz, 1H), 4.60-4.75 (m, J = 4.3 Hz, 1H) | 4 | 1.571 | 457.2 |
| 1398 | A127-M-B65 isomer S | 8.62 (d, J = 8.4 Hz, 1H), 8.50 (d, J = 8.7 Hz, 1H), 7.89 (br. s., 3H), 7.73 (br. s., 1H), 5.05-5.22 (m, J = 3.5 Hz, 1H), 4.58-4.72 (m, J = 6.9, 6.9, 3.3 Hz, 1H) | 4 | 1.44 | 407.2 |
| 1399 | A158-M-B65 isomer S | 8.58 (d, J = 8.3 Hz, 1H), 8.45 (d, J = 8.3 Hz, 1H), 5.02-5.26 (m, J = 9.0, 4.6, 4.6 Hz, 1H), 4.63-4.77 (m, 1H) | 4 | 1.451 | 425.2 |

The invention claimed is:

1. A library of two or more compounds of formula (I):

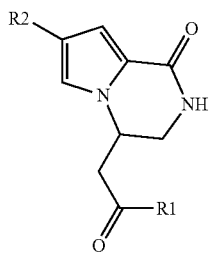

wherein:

R1 is —NR$^a$R$^b$ or —OR$^a$ and

R2 is —NH$_2$, —NHCOR$^c$, —NHCONHR$^c$, —NHSO$_2$R$^c$, —C≡CR$^d$ or R$^d$ wherein R$^a$, R$^b$, R$^c$ and R$^d$ are each independently hydrogen; or a group selected from straight or branched C$_1$-C$_6$ alkyl, C$_2$-C$_6$ alkenyl, C$_2$-C$_6$ alkynyl, C$_3$-C$_6$ cycloalkyl, cycloalkyl C$_1$-C$_6$ alkyl, heterocyclyl, heterocyclyl C$_1$-C$_6$ alkyl, aryl, aryl C$_1$-C$_6$ alkyl, heteroaryl and heteroaryl C$_1$-C$_6$ alkyl, unsubstituted or substituted in a free position with a group selected from halogen, nitro, oxo, carboxy, cyano, C$_1$-C$_6$ alkyl, polyfluorinated alkyl, C$_2$-C$_6$ alkenyl, C$_2$-C$_6$ alkynyl, C$_3$-C$_6$ cycloalkyl, heterocyclyl, aryl, heteroaryl, amino, carbonylamino, hydroxy, a sulfurated derivative selected from the group consisting of alkylthio, arylthio, alkylsulfonyl, arylsulfonyl, alkylsulfinyl, arylsulfinyl, arylsulfonyloxy, aminosulfonyl, alkylaminosulfonyl and dialkylaminosulfonyl; or R$^a$ and R$^b$, taken together with the nitrogen atom to which they are bonded, may form 3- to 7-membered heterocyclyl or heteroaryl, optionally containing one additional heteroatom or heteroatomic group selected from S, O, N or NH, and pharmaceutically acceptable salts thereof.

2. A library according to claim 1 wherein the compound has the formula:

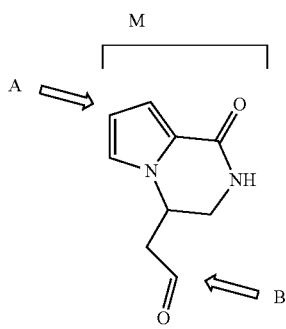

wherein R2 is a fragment denoted by any of codes A1-A22 or A24-A158 and R1 is a fragment denoted by any of codes B1-B65:

| Fragment | CODE |
|---|---|
| 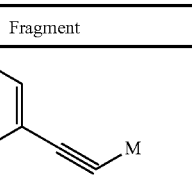 | A1 |
| | A2 |
| | A3 |
| | A4 |
| | A5 |
| | A6 |
| | A7 |
| | A8 |
| | A9 |
| | A10 |
| | A11 |
| | A12 |

-continued

| Fragment | CODE |
|---|---|
| HN-M with CH2-CN and C=O | A13 |
| 2-oxo-2H-pyran-4-carboxamide (M-NH-C(O)-) | A14 |
| 5-methylthiophene-2-carboxamide (M-NH-C(O)-) | A15 |
| M-NH-C(O)-NH-cyclohexyl | A16 |
| 4-methoxyphenyl-NH-C(O)-NH-M | A17 |
| M-CH=CH-C(O)-N(piperidine) | A18 |
| M-CH=CH-C(O)-O-butyl | A19 |
| 4-chlorophenyl-M | A20 |
| 4-nitrophenyl-M | A21 |
| 4-methoxyphenyl-CH=CH-M | A22 |

-continued

| Fragment | CODE |
|---|---|
| pyridin-4-yl-M | A24 |
| cyclopentyl-C≡C-M | A25 |
| 4-methoxyphenyl-C≡C-M | A26 |
| 4-chlorophenyl-C≡C-M | A27 |
| 2,5-dimethylpyrrol-1-yl-(3-ethynylphenyl)-M | A28 |
| CH3-CH=CH-M | A29 |
| cyclohexyl-CH=CH-M | A30 |
| phenyl-CH=CH-M | A31 |
| 4-chlorophenyl-CH=CH-M | A32 |
| thiophen-3-yl-M | A33 |
| phenyl-M | A34 |

-continued
| Fragment | CODE |
|---|---|
| 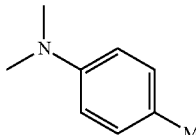 | A35 |
| 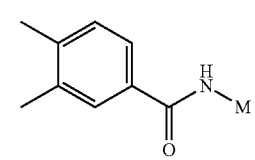 | A36 |
| 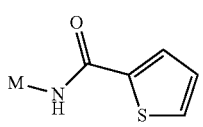 | A37 |
| 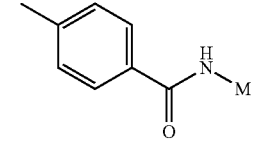 | A38 |
| 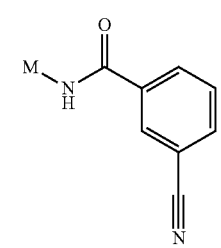 | A39 |
| 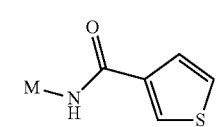 | A40 |
| 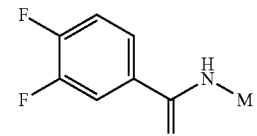 | A41 |
| 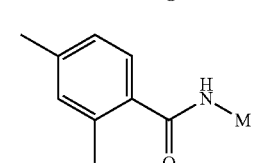 | A42 |
| 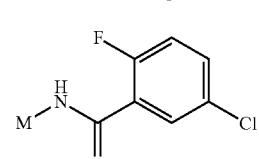 | A43 |
| 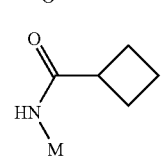 | A44 |
-continued
| Fragment | CODE |
|---|---|
| 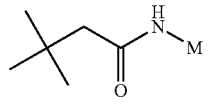 | A45 |
| 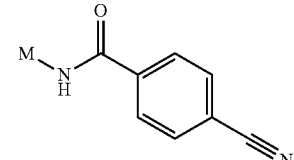 | A46 |
| 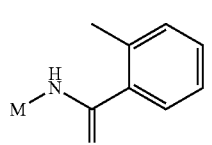 | A47 |
| 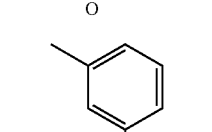 | A48 |
| 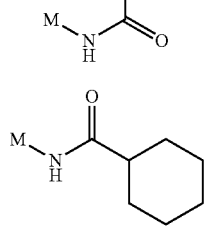 | A49 |
| 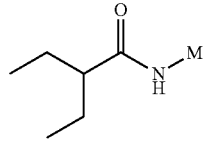 | A50 |
| 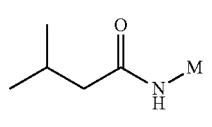 | A51 |
| 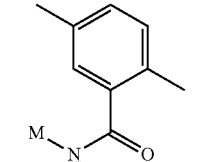 | A52 |
| 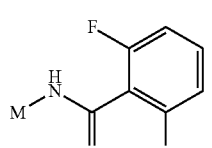 | A53 |
| 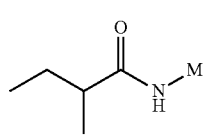 | A54 |

-continued

| Fragment | CODE |
|---|---|
| (2,4-difluorobenzamide) | A55 |
| (3,5-difluorobenzamide) | A56 |
| (3,5-dimethylbenzamide) | A57 |
| (3-methylthiophene-2-carboxamide) | A58 |
| (2-chloro-4-fluorobenzamide) | A59 |
| (pivalamide) | A60 |
| (pentanamide) | A61 |
| (benzamide) | A62 |
| (3-fluoro-4-methylbenzamide) | A63 |

-continued

| Fragment | CODE |
|---|---|
| (2-fluorobenzamide) | A64 |
| (cyclopentanecarboxamide) | A65 |
| (2-chloro-5-fluorobenzamide) | A66 |
| (2,5-difluorobenzamide) | A67 |
| (2-chlorobenzamide) | A68 |
| (butyramide) | A69 |
| (3-fluorobenzamide) | A70 |
| (isobutyramide) | A71 |
| (1-ethyl-1H-pyrazole-3-carboxamide) | A72 |
| (1-(2-fluorophenyl)urea) | A73 |

-continued
| Fragment | CODE |
|---|---|
| 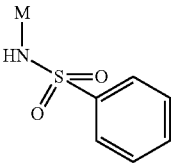 | A74 |
| 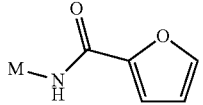 | A75 |
| 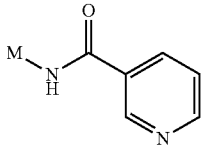 | A76 |
| 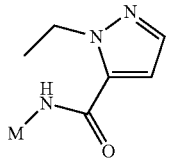 | A77 |
| 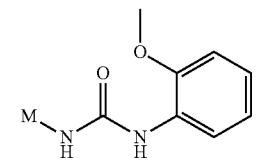 | A78 |
| 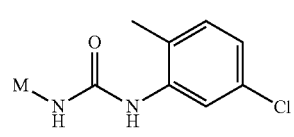 | A79 |
| 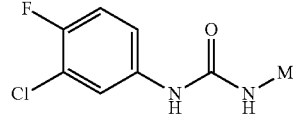 | A80 |
| 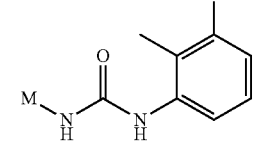 | A81 |
| 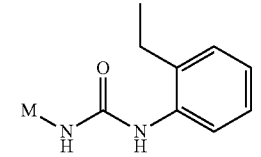 | A82 |
| 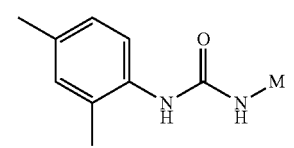 | A83 |
-continued
| Fragment | CODE |
|---|---|
| 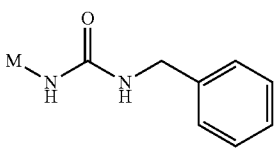 | A84 |
| 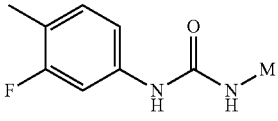 | A85 |
| 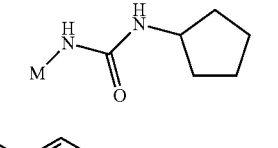 | A86 |
| 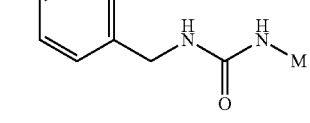 | A87 |
| 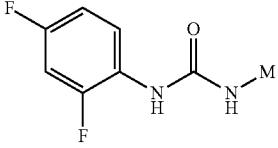 | A88 |
| 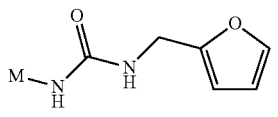 | A89 |
| 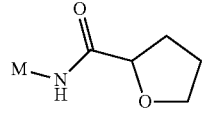 | A90 |
| 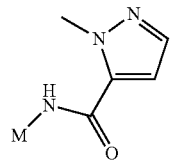 | A91 |
| 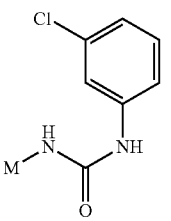 | A92 |
| 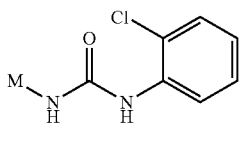 | A93 |

| Fragment | CODE |
|---|---|
| 4-chlorophenyl urea-M | A94 |
| 2-methylphenyl urea-M | A95 |
| 3-methylphenyl urea-M | A96 |
| 3-methoxyphenyl urea-M | A97 |
| 3-cyanophenyl urea-M | A98 |
| 3-chloro-4-methylphenyl urea-M | A99 |
| 3,5-dimethylphenyl urea-M | A100 |
| isopentyl urea-M | A101 |

| Fragment | CODE |
|---|---|
| 3-fluorophenyl urea-M | A102 |
| isobutyl urea-M | A103 |
| 2,6-dimethylphenyl urea-M | A104 |
| 3-ethylphenyl urea-M | A105 |
| 4-ethylphenyl urea-M | A106 |
| 2-chloro-4-methylphenyl urea-M | A107 |
| cyclohexylacetamide-M | A108 |
| 2-chloro-6-fluorobenzamide-M | A109 |
| 3-fluoro-2-methylphenyl urea-M | A110 |

| Fragment | CODE | | Fragment | CODE |
|---|---|---|---|---|
| 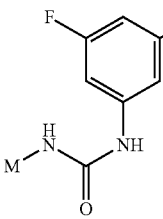 | A111 | | 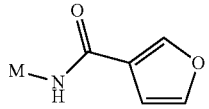 | A123 |
|  | A112 | | 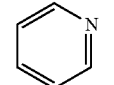 | A124 |
| 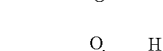 | A113 | | 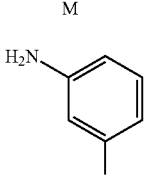 | A125 |
|  | A114 | | 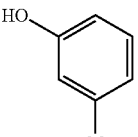 | A126 |
|  | A115 | | 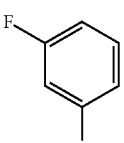 | A127 |
| 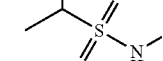 | A116 | | 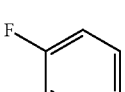 | A128 |
|  | A117 | | 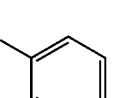 | A129 |
|  | A118 | | 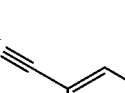 | A130 |
|  | A119 | | | |
| 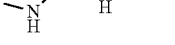 | A120 | | 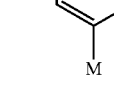 | A131 |
| 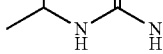 | A121 | | | |
| 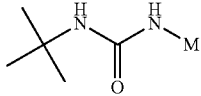 | A122 | | 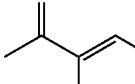 | A132 |

-continued

| Fragment | CODE |
|---|---|
| 3-(trifluoromethyl)phenyl-M | A133 |
| 3-(trifluoromethoxy)phenyl-M | A134 |
| 4-(trifluoromethoxy)phenyl-M | A135 |
| 4-aminophenyl-M | A136 |
| 3-methylphenyl-M | A137 |
| 3-methoxyphenyl-M | A138 |
| 3,4-difluorophenyl-M | A139 |
| 3-(methylthio)phenyl-M | A140 |
| methyl 4-benzoate-M | A141 |
| methyl 3-benzoate-M | A142 |

-continued

| Fragment | CODE |
|---|---|
| 4-(trifluoromethyl)phenyl-M | A143 |
| 1H-pyrazol-4-yl-M | A144 |
| 5-bromo-1H-indol-2-yl-M | A145 |
| 5-fluoro-2-methoxyphenyl-M | A146 |
| 4-methylphenyl-M | A147 |
| 4-fluoro-2-methoxyphenyl-M | A148 |
| 3,5-difluorophenyl-M | A149 |
| 3-chlorophenyl-M | A150 |
| 2,4-difluorophenyl-M | A151 |
| (Z)-but-1-enyl-M | A152 |

-continued

| Fragment | CODE |
|---|---|
| (1-phenylvinyl, M) | A153 |
| (propenyl, M) | A154 |
| (2-pyridyl-ethynyl, M) | A155 |
| (8-quinolinyl, M) | A156 |
| (2-fluoro-4-pyridyl, M) | A157 |
| (2,5-difluorophenyl, M) | A158 |
| (ethoxy, M) | B1 |
| (HO-M) | B2 |
| (butoxy, M) | B3 |
| (2-methyl-6-morpholinyl-methyl, M) | B4 |
| (1-piperidinyl, M) | B5 |
| (phenethylamino, M) | B6 |
| (2-methoxyethylamino, M) | B7 |
| (3-dimethylamino-propylamino, M) | B8 |
| (neopentylamino, M) | B9 |

-continued

| Fragment | CODE |
|---|---|
| (2,6-dimethylmorpholinyl, M) cis | B10 |
| (2,6-dimethylmorpholinyl, M) trans | B11 |
| (tetrahydrofuran-2-ylmethylamino, M) | B12 |
| (isopropylamino, M) | B13 |
| (benzylamino, M) | B14 |
| (sec-butylamino, M) | B15 |
| (1-phenylethylamino, M) | B16 |
| (ethylamino, M) | B17 |
| (4-methylcyclohexylamino, M) | B18 |
| (cyclopropylamino, M) | B19 |
| (2-methylbenzylamino, M) | B20 |
| (4-methylbenzylamino, M) | B21 |
| (cyclohexylmethylamino, M) | B22 |
| (isobutylamino, M) | B23 |
| (cyclohexylamino, M) | B24 |
| (propylamino, M) | B25 |

| Fragment | CODE |
|---|---|
| cyclopentyl-NH-M | B26 |
| allyl-NH-M | B27 |
| tetrahydropyran-4-yl-NH-M | B28 |
| (pyridin-3-yl)methyl-NH-M | B29 |
| (3-fluorophenyl)methyl-NH-M | B30 |
| (CH₃)₂N-M | B31 |
| isopentyl-NH-M | B32 |
| 4-(pyridin-2-yl)piperazin-1-yl-M | B33 |
| thiomorpholin-4-yl-M | B34 |
| CH₃-NH-M | B35 |
| (2-methylphenyl)-NH-M | B36 |
| (3-methylphenyl)-NH-M | B37 |
| 2-(morpholin-4-yl)ethyl-NH-M | B38 |
| (pyridin-4-yl)methyl-NH-M | B39 |
| (furan-2-yl)methyl-NH-M | B40 |

| Fragment | CODE |
|---|---|
| 4-carbamoylpiperidin-1-yl-M | B41 |
| 3-methoxypropyl-NH-M | B42 |
| tert-butyl-NH-M | B43 |
| 2-(pyrrolidin-1-yl)ethyl-NH-M | B44 |
| azepan-1-yl-M | B45 |
| N-methyl-N-propyl-amino-M | B46 |
| (5-methylfuran-2-yl)methyl-NH-M | B47 |
| cyclopropylmethyl-NH-M | B48 |
| 4-allylpiperazin-1-yl-M | B49 |
| pyrrolidin-1-yl-M | B50 |
| morpholin-4-yl-M | B51 |
| phenyl-NH-M | B52 |
| 2-(1-methylpiperidin-4-yl)ethyl-NH-M | B53 |
| (1,3-dimethyl-1H-pyrazol-4-yl)methyl-N(CH₃)-M | B54 |
| 2-(1,3,5-trimethyl-1H-pyrazol-4-yl)ethyl-N(CH₃)-M | B55 |

-continued

| Fragment | CODE |
|---|---|
| (1-methylpiperazine attached via N to M) | B56 |
| (1-methyl-4-(piperazin-1-yl)piperidine attached via N to M) | B57 |
| (4-(methylsulfonyl)piperazine attached via N to M) | B58 |
| (1-methyl-1,4-diazepane attached via N to M) | B59 |
| (N,N-dimethylethylenediamine, NH to M) | B60 |
| (1-cyclohexyl-2-hydroxyethylamine, NH to M) | B61 |
| (2-amino-2-phenyl-1,3-propanediol-like, NH to M) | B62 |
| (1-methyl-3-phenylpiperazine attached via N to M) | B63 |
| (2-amino-3-phenyl-1-propanol, NH to M) | B64 |
| (1-phenylethylamine with NH2, NH to M) | B65 | and wherein the compound is one of those listed herein below:

| Entry | Compound | HPLC Method | HPLC Rt (min) | [M + H]+ |
|---|---|---|---|---|
| 1 | A1-M-B1 | 2 | 5.17 | 323.2 |
| 2 | A1-M-B2 | 2 | 4.49 | 295.2 |
| 3 | A1-M-B6 | 2 | 6.04 | 398.3 |
| 4 | A1-M-B7 | 2 | 5.06 | 352.3 |
| 5 | A1-M-B8 | 2 | 4.27 | 380.3 |
| 6 | A1-M-B9 | 2 | 6.05 | 364.3 |
| 7 | A2-M-B1 | 2 | 4.53 | 329.2 |
| 8 | A2-M-B2 | 2 | 3.06 | 301.2 |
| 9 | A2-M-B3 | 2 | 5.31 | 357.3 |
| 10 | A2-M-B4 | 2 | 4.15 | 398.3 |
| 11 | A3-M-B1 | 2 | 3.92 | 372.2 |
| 12 | A3-M-B2 | 2 | 2.8 | 344.2 |
| 13 | A3-M-B5 | 2 | 3.77 | 411.3 |
| 14 | A4-M-B1 | 2 | 4.08 | 392.2 |
| 15 | A4-M-B10 | 2 | 3.72 | 461.3 |
| 16 | A4-M-B11 | 2 | 3.8 | 461.3 |
| 17 | A4-M-B2 | 2 | 2.86 | 364.2 |
| 18 | A5-M-B1 | 2 | 3.95 | 357.2 |
| 19 | A5-M-B12 | 1 | 2.54 | 412.3 |
| 20 | A5-M-B16 | 1 | 3.19 | 432.3 |
| 21 | A5-M-B17 | 1 | 2.38 | 356.3 |
| 22 | A5-M-B18 | 1 | 3.6 | 424.3 |
| 23 | A5-M-B2 | 2 | 2.72 | 329.2 |
| 24 | A5-M-B21 | 1 | 3.34 | 432.3 |
| 25 | A5-M-B22 | 1 | 3.55 | 424.3 |
| 26 | A5-M-B23 | 1 | 2.94 | 384.3 |
| 27 | A5-M-B24 | 1 | 3.28 | 410.3 |
| 28 | A5-M-B26 | 1 | 2.99 | 396.3 |
| 29 | A5-M-B5 | 2 | 3.74 | 396.3 |
| 30 | A5-M-B7 | 2 | 3.11 | 386.3 |
| 31 | A5-M-B7 | 1 | 2.34 | 386.3 |
| 32 | A5-M-B8 | 2 | 2.72 | 413.3 |
| 33 | A6-M-B1 | 2 | 4.18 | 321.2 |
| 34 | A7-M-B1 | 2 | 3.99 | 360.2 |
| 35 | A7-M-B12 | 1 | 2.62 | 415.3 |
| 36 | A7-M-B13 | 1 | 2.7 | 373.3 |
| 37 | A7-M-B14 | 1 | 3.11 | 421.3 |
| 38 | A7-M-B16 | 1 | 3.33 | 435.3 |
| 39 | A7-M-B17 | 1 | 2.48 | 359.2 |
| 40 | A7-M-B18 | 1 | 3.64 | 427.3 |
| 41 | A7-M-B19 | 1 | 2.49 | 371.2 |
| 42 | A7-M-B2 | 2 | 3.7 | 332.2 |
| 43 | A7-M-B20 | 1 | 3.35 | 435.3 |
| 44 | A7-M-B21 | 1 | 3.38 | 435.3 |
| 45 | A7-M-B22 | 1 | 3.59 | 427.3 |
| 46 | A7-M-B23 | 1 | 3 | 387.3 |
| 47 | A7-M-B24 | 1 | 3.33 | 413.3 |
| 48 | A7-M-B25 | 1 | 2.73 | 373.3 |
| 49 | A7-M-B26 | 1 | 3.06 | 399.3 |
| 50 | A7-M-B27 | 1 | 2.61 | 371.2 |
| 51 | A7-M-B7 | 1 | 2.43 | 389.3 |
| 52 | A8-M-B1 | 2 | 3.96 | 396.3 |
| 53 | A8-M-B2 | 2 | 3.5 | 368.2 |
| 54 | A9-M-B1 | 2 | 4.04 | 375.2 |
| 55 | A9-M-B14 | 1 | 3.19 | 436.3 |
| 56 | A9-M-B15 | 1 | 3.04 | 402.3 |
| 57 | A9-M-B16 | 1 | 3.38 | 450.3 |
| 58 | A9-M-B17 | 1 | 2.53 | 374.3 |
| 59 | A9-M-B18 | 1 | 3.69 | 442.3 |
| 60 | A9-M-B19 | 1 | 2.56 | 386.3 |
| 61 | A9-M-B2 | 2 | 3.68 | 347.2 |
| 62 | A9-M-B20 | 1 | 3.43 | 450.3 |
| 63 | A9-M-B21 | 1 | 3.47 | 450.3 |
| 64 | A9-M-B22 | 1 | 3.66 | 442.3 |
| 65 | A9-M-B23 | 1 | 3.08 | 402.3 |
| 66 | A9-M-B24 | 1 | 3.41 | 428.3 |
| 67 | A9-M-B26 | 1 | 3.13 | 414.3 |
| 68 | A9-M-B27 | 1 | 2.67 | 386.3 |
| 69 | A9-M-B7 | 1 | 2.48 | 404.3 |
| 70 | A10-M-B2 | 2 | 1.34 | 265.2 |
| 71 | A11-M-B6 | 2 | 2.7 | 398.3 |
| 72 | A11-M-B7 | 2 | 1.06 | 352.3 |
| 73 | A11-M-B8 | 2 | 3.32 | 379.3 |
| 74 | A11-M-B9 | 2 | 2.52 | 364.3 |

-continued

| Entry | Compound | HPLC Method | HPLC Rt (min) | [M + H]+ |
|---|---|---|---|---|
| 75 | A12-M-B13 | 1 | 1.99 | 319.3 |
| 76 | A12-M-B14 | 1 | 2.43 | 367.3 |
| 77 | A12-M-B16 | 1 | 2.71 | 381.3 |
| 78 | A12-M-B20 | 1 | 2.73 | 381.3 |
| 79 | A12-M-B21 | 1 | 2.79 | 381.3 |
| 80 | A12-M-B22 | 1 | 3.03 | 373.3 |
| 81 | A12-M-B7 | 2 | 3.29 | 335.3 |
| 82 | A12-M-B8 | 2 | 2.69 | 362.3 |
| 83 | A13-M-B7 | 2 | 2.81 | 334.2 |
| 84 | A13-M-B8 | 2 | 1.26 | 361.3 |
| 85 | A13-M-B9 | 2 | 3.12 | 346.3 |
| 86 | A14-M-B7 | 2 | 3.84 | 389.2 |
| 87 | A14-M-B8 | 2 | 3.03 | 416.3 |
| 88 | A15-M-B12 | 1 | 2.61 | 417.3 |
| 89 | A15-M-B13 | 1 | 2.68 | 375.2 |
| 90 | A15-M-B14 | 1 | 3.07 | 423.2 |
| 91 | A15-M-B15 | 1 | 2.92 | 389.3 |
| 92 | A15-M-B16 | 1 | 3.28 | 437.3 |
| 93 | A15-M-B18 | 1 | 3.59 | 429.3 |
| 94 | A15-M-B19 | 1 | 2.52 | 373.2 |
| 95 | A15-M-B20 | 1 | 3.3 | 437.3 |
| 96 | A15-M-B21 | 1 | 3.32 | 437.3 |
| 97 | A15-M-B22 | 1 | 3.52 | 429.3 |
| 98 | A15-M-B23 | 1 | 2.97 | 389.3 |
| 99 | A15-M-24 | 1 | 3.28 | 415.3 |
| 100 | A15-M-B25 | 1 | 2.72 | 375.2 |
| 101 | A15-M-B26 | 1 | 3.02 | 401.3 |
| 102 | A15-M-B27 | 1 | 2.6 | 373.2 |
| 103 | A15-M-B7 | 1 | 2.44 | 391.2 |
| 104 | A15-M-B8 | 2 | 2.85 | 418.3 |
| 105 | A16-M-B14 | 1 | 3.32 | 424.3 |
| 106 | A16-M-B18 | 1 | 3.83 | 430.4 |
| 107 | A16-M-B20 | 1 | 3.56 | 438.3 |
| 108 | A16-M-B21 | 1 | 3.6 | 438.3 |
| 109 | A16-M-B22 | 1 | 3.81 | 430.4 |
| 110 | A16-M-B23 | 1 | 3.23 | 390.3 |
| 111 | A16-M-B24 | 1 | 3.54 | 416.4 |
| 112 | A16-M-B27 | 1 | 2.82 | 374.3 |
| 113 | A16-M-B8 | 2 | 2.89 | 419.4 |
| 114 | A17-M-B14 | 1 | 2.89 | 448.3 |
| 115 | A17-M-B21 | 1 | 3.17 | 462.3 |
| 116 | A17-M-B24 | 1 | 3.11 | 440.3 |
| 117 | A17-M-B6 | 2 | 4.02 | 462.3 |
| 118 | A17-M-B8 | 2 | 2.72 | 443.3 |
| 119 | A17-M-B9 | 2 | 3.97 | 428.3 |
| 120 | A18-M-B5 | 2 | 3.62 | 399.3 |
| 121 | A19-M-B5 | 2 | 4.38 | 388.3 |
| 122 | A20-M-B1 | 2 | 5.13 | 333.2 |
| 123 | A20-M-B6 | 2 | 5.98 | 408.2 |
| 124 | A20-M-B7 | 2 | 4.99 | 362.2 |
| 125 | A20-M-B8 | 2 | 3.33 | 389.2 |
| 126 | A20-M-B9 | 2 | 5.99 | 374.3 |
| 127 | A21-M-B1 | 2 | 4.61 | 344.2 |
| 128 | A22-M-B1 | 2 | 5.12 | 355.3 |
| 129 | A22-M-B2 | 2 | 4.4 | 327.2 |
| 130 | A22-M-B6 | 2 | 5.87 | 430.3 |
| 131 | A22-M-B7 | 2 | 4.94 | 384.3 |
| 132 | A22-M-B8 | 2 | 4.14 | 411.3 |
| 133 | A22-M-B9 | 2 | 5.88 | 396.3 |
| 135 | A24-M-B6 | 2 | 4.17 | 375.3 |
| 136 | A24-M-B7 | 2 | 2.45 | 329.3 |
| 137 | A24-M-B8 | 2 | 1.97 | 356.3 |
| 138 | A24-M-B9 | 2 | 4.07 | 341.3 |
| 139 | A25-M-B1 | 2 | 6.16 | 315.3 |
| 140 | A25-M-B2 | 2 | 4.58 | 287.2 |
| 141 | A25-M-B6 | 2 | 6.23 | 390.3 |
| 142 | A25-M-B7 | 2 | 5.2 | 344.3 |
| 143 | A25-M-B8 | 2 | 4.3 | 371.3 |
| 144 | A25-M-B9 | 2 | 6.24 | 356.3 |
| 145 | A26-M-B1 | 2 | 5.9 | 353.2 |
| 146 | A26-M-B2 | 2 | 4.48 | 325.2 |
| 147 | A26-M-B6 | 2 | 5.96 | 428.3 |
| 148 | A26-M-B7 | 2 | 5.04 | 382.3 |
| 149 | A26-M-B8 | 2 | 4.22 | 409.3 |
| 150 | A26-M-B9 | 2 | 5.98 | 394.3 |
| 151 | A27-M-B1 | 2 | 6.48 | 357.2 |
| 152 | A27-M-B2 | 2 | 4.98 | 329.2 |
| 153 | A27-M-B6 | 2 | 6.5 | 432.2 |
| 154 | A27-M-B7 | 2 | 5.57 | 386.2 |
| 155 | A27-M-B8 | 2 | 4.72 | 413.3 |
| 156 | A27-M-B9 | 2 | 6.54 | 398.3 |
| 157 | A28-M-B1 | 2 | 6.92 | 416.3 |
| 158 | A28-M-B2 | 2 | 5.52 | 388.3 |
| 159 | A28-M-B6 | 2 | 6.9 | 491.3 |
| 160 | A28-M-B7 | 2 | 6.07 | 445.3 |
| 161 | A28-M-B8 | 2 | 5.16 | 472.4 |
| 162 | A28-M-B9 | 2 | 6.95 | 457.4 |
| 163 | A29-M-B1 | 2 | 5.12 | 263.2 |
| 164 | A29-M-B2 | 2 | 3.51 | 235.2 |
| 165 | A29-M-B6 | 2 | 5.35 | 338.3 |
| 166 | A29-M-B7 | 2 | 4.14 | 292.3 |
| 167 | A29-M-B8 | 2 | 3.35 | 319.3 |
| 168 | A29-M-B9 | 2 | 5.31 | 304.3 |
| 169 | A30-M-B1 | 2 | 6.8 | 331.3 |
| 170 | A30-M-B2 | 2 | 5.11 | 303.3 |
| 171 | A30-M-B6 | 2 | 6.76 | 406.3 |
| 172 | A30-M-B7 | 2 | 5.76 | 360.3 |
| 173 | A30-M-B8 | 2 | 4.78 | 387.4 |
| 174 | A30-M-B9 | 2 | 6.82 | 372.4 |
| 175 | A31-M-B1 | 2 | 5.92 | 325.2 |
| 176 | A31-M-B2 | 2 | 4.45 | 297.2 |
| 177 | A31-M-B6 | 2 | 5.98 | 400.3 |
| 178 | A31-M-B7 | 2 | 5.02 | 354.3 |
| 179 | A31-M-B8 | 2 | 4.17 | 381.3 |
| 180 | A31-M-B9 | 2 | 5.99 | 366.3 |
| 181 | A32-M-B1 | 2 | 6.4 | 359.2 |
| 182 | A32-M-B2 | 2 | 4.92 | 331.2 |
| 183 | A32-M-B6 | 2 | 6.41 | 434.3 |
| 184 | A32-M-B7 | 2 | 5.5 | 388.2 |
| 185 | A32-M-B8 | 2 | 4.7 | 415.3 |
| 186 | A32-M-B9 | 2 | 6.45 | 400.3 |
| 187 | A33-M-B6 | 2 | 5.42 | 380.2 |
| 188 | A33-M-B7 | 2 | 4.33 | 334.2 |
| 189 | A33-M-B8 | 3 | 3.88 | 361.2 |
| 190 | A33-M-B9 | 2 | 5.39 | 346.3 |
| 191 | A34-M-B6 | 2 | 5.55 | 374.3 |
| 192 | A34-M-B7 | 2 | 4.48 | 328.3 |
| 193 | A34-M-B8 | 3 | 4.11 | 355.3 |
| 194 | A34-M-B9 | 2 | 5.49 | 340.3 |
| 195 | A35-M-B7 | 2 | 4.62 | 371.3 |
| 196 | A36-M-B12 | 1 | 3.02 | 425.3 |
| 197 | A36-M-B14 | 1 | 3.44 | 431.3 |
| 198 | A36-M-B15 | 1 | 3.33 | 397.3 |
| 199 | A36-M-B16 | 1 | 3.63 | 445.3 |
| 200 | A36-M-B17 | 1 | 2.91 | 369.3 |
| 201 | A36-M-B20 | 1 | 3.65 | 445.3 |
| 202 | A36-M-B21 | 1 | 3.65 | 445.3 |
| 203 | A36-M-B22 | 1 | 3.85 | 437.3 |
| 204 | A36-M-B26 | 1 | 3.4 | 409.3 |
| 205 | A36-M-B7 | 1 | 2.86 | 399.3 |
| 206 | A37-M-B12 | 1 | 2.3 | 403.2 |
| 207 | A37-M-B13 | 1 | 2.34 | 361.2 |
| 208 | A37-M-B14 | 1 | 2.77 | 409.2 |
| 209 | A37-M-B15 | 1 | 2.61 | 375.2 |
| 210 | A37-M-B16 | 1 | 3 | 423.2 |
| 211 | A37-M-B17 | 1 | 2.14 | 347.2 |
| 212 | A37-M-B18 | 1 | 3.33 | 415.3 |
| 213 | A37-M-B19 | 1 | 2.17 | 359.2 |
| 214 | A37-M-B20 | 1 | 3.02 | 423.2 |
| 215 | A37-M-B21 | 1 | 3.05 | 423.2 |
| 216 | A37-M-B22 | 1 | 3.26 | 415.3 |
| 217 | A37-M-B23 | 1 | 2.65 | 375.2 |
| 218 | A37-M-B24 | 1 | 2.98 | 401.3 |
| 219 | A37-M-B25 | 1 | 2.37 | 361.2 |
| 220 | A37-M-B26 | 1 | 2.7 | 387.2 |
| 221 | A37-M-B27 | 1 | 2.26 | 359.2 |
| 222 | A37-M-B7 | 1 | 2.11 | 377.2 |
| 223 | A38-M-B12 | 1 | 2.75 | 411.3 |
| 224 | A38-M-B13 | 1 | 2.84 | 369.3 |
| 225 | A38-M-B14 | 1 | 3.21 | 417.3 |
| 226 | A38-M-B15 | 1 | 3.07 | 383.3 |
| 227 | A38-M-B16 | 1 | 3.41 | 431.3 |

-continued

| Entry | Compound | HPLC Method | HPLC Rt (min) | [M + H]+ |
|---|---|---|---|---|
| 228 | A38-M-B17 | 1 | 2.63 | 355.3 |
| 229 | A38-M-B18 | 1 | 3.7 | 423.3 |
| 230 | A38-M-B19 | 1 | 2.66 | 367.3 |
| 231 | A38-M-B20 | 1 | 3.43 | 431.3 |
| 232 | A38-M-B21 | 1 | 3.46 | 431.3 |
| 233 | A38-M-B22 | 1 | 3.65 | 423.3 |
| 234 | A38-M-B23 | 1 | 3.1 | 383.3 |
| 235 | A38-M-B24 | 1 | 3.41 | 409.3 |
| 236 | A38-M-B25 | 1 | 2.87 | 369.3 |
| 237 | A38-M-B26 | 1 | 3.16 | 395.3 |
| 238 | A38-M-B27 | 1 | 2.74 | 367.3 |
| 239 | A38-M-B7 | 1 | 2.58 | 385.3 |
| 240 | A39-M-B12 | 1 | 2.33 | 422.3 |
| 241 | A39-M-B13 | 1 | 2.39 | 380.3 |
| 242 | A39-M-B14 | 1 | 2.79 | 428.3 |
| 243 | A39-M-B15 | 1 | 2.64 | 394.3 |
| 244 | A39-M-B16 | 1 | 3.02 | 442.3 |
| 245 | A39-M-B18 | 1 | 3.32 | 434.3 |
| 246 | A39-M-B19 | 1 | 2.22 | 378.2 |
| 247 | A39-M-B20 | 1 | 3.02 | 442.3 |
| 248 | A39-M-B21 | 1 | 3.04 | 442.3 |
| 249 | A39-M-B22 | 1 | 3.24 | 434.3 |
| 250 | A39-M-B23 | 1 | 2.67 | 394.3 |
| 251 | A39-M-B24 | 1 | 2.98 | 420.3 |
| 252 | A39-M-B25 | 1 | 2.42 | 380.3 |
| 253 | A39-M-B26 | 1 | 2.72 | 406.3 |
| 254 | A39-M-B27 | 1 | 2.32 | 378.2 |
| 255 | A39-M-B7 | 1 | 2.18 | 396.3 |
| 256 | A40-M-B12 | 1 | 2.31 | 403.2 |
| 257 | A40-M-B13 | 1 | 2.36 | 361.2 |
| 258 | A40-M-B14 | 1 | 2.8 | 409.2 |
| 259 | A40-M-B15 | 1 | 2.63 | 375.2 |
| 260 | A40-M-B16 | 1 | 3.04 | 423.2 |
| 261 | A40-M-B18 | 1 | 3.38 | 415.3 |
| 262 | A40-M-B19 | 1 | 2.17 | 359.2 |
| 263 | A40-M-B20 | 1 | 3.06 | 423.2 |
| 264 | A40-M-B21 | 1 | 3.1 | 423.2 |
| 265 | A40-M-B22 | 1 | 3.31 | 415.3 |
| 266 | A40-M-B23 | 1 | 2.67 | 375.2 |
| 267 | A40-M-B24 | 1 | 3.03 | 401.3 |
| 268 | A40-M-B25 | 1 | 2.39 | 361.2 |
| 269 | A40-M-B26 | 1 | 2.73 | 387.2 |
| 270 | A40-M-B27 | 1 | 2.27 | 359.2 |
| 271 | A40-M-B7 | 1 | 2.13 | 377.2 |
| 272 | A41-M-B12 | 1 | 2.88 | 433.3 |
| 273 | A41-M-B13 | 1 | 2.97 | 391.3 |
| 274 | A41-M-B14 | 1 | 3.36 | 439.3 |
| 275 | A41-M-B15 | 1 | 3.22 | 405.3 |
| 276 | A41-M-B16 | 1 | 3.56 | 453.3 |
| 277 | A41-M-B18 | 1 | 3.8 | 445.3 |
| 278 | A41-M-B19 | 1 | 2.78 | 389.2 |
| 279 | A41-M-B20 | 1 | 3.59 | 453.3 |
| 280 | A41-M-B21 | 1 | 3.6 | 453.3 |
| 281 | A41-M-B22 | 1 | 3.8 | 445.3 |
| 282 | A41-M-B23 | 1 | 3.26 | 405.3 |
| 283 | A41-M-B24 | 1 | 3.57 | 431.3 |
| 284 | A41-M-B25 | 1 | 3 | 391.3 |
| 285 | A41-M-B26 | 1 | 3.31 | 417.3 |
| 286 | A41-M-B27 | 1 | 2.87 | 389.2 |
| 287 | A41-M-B7 | 1 | 2.68 | 407.2 |
| 288 | A42-M-B12 | 1 | 2.89 | 425.3 |
| 289 | A42-M-B13 | 1 | 2.99 | 383.3 |
| 290 | A42-M-B14 | 1 | 3.38 | 431.3 |
| 291 | A42-M-B15 | 1 | 3.23 | 397.3 |
| 292 | A42-M-B16 | 1 | 3.56 | 445.3 |
| 293 | A42-M-B18 | 1 | 3.84 | 437.3 |
| 294 | A42-M-B19 | 1 | 2.8 | 381.3 |
| 295 | A42-M-B20 | 1 | 3.59 | 445.3 |
| 296 | A42-M-B21 | 1 | 3.63 | 445.3 |
| 297 | A42-M-B22 | 1 | 3.82 | 437.3 |
| 298 | A42-M-B23 | 1 | 3.27 | 397.3 |
| 299 | A42-M-B24 | 1 | 3.57 | 423.3 |
| 300 | A42-M-B25 | 1 | 3.02 | 383.3 |
| 301 | A42-M-B26 | 1 | 3.33 | 409.3 |
| 302 | A42-M-B27 | 1 | 2.9 | 381.3 |
| 303 | A42-M-B7 | 1 | 2.73 | 399.3 |
| 304 | A43-M-B12 | 1 | 2.84 | 449.2 |
| 305 | A43-M-B14 | 1 | 3.3 | 455.2 |
| 306 | A43-M-B15 | 1 | 3.16 | 421.2 |
| 307 | A43-M-B16 | 1 | 3.5 | 469.2 |
| 308 | A43-M-B18 | 1 | 3.76 | 461.3 |
| 309 | A43-M-B19 | 1 | 2.74 | 405.2 |
| 310 | A43-M-B20 | 1 | 3.53 | 469.2 |
| 311 | A43-M-B21 | 1 | 3.55 | 469.2 |
| 312 | A43-M-B22 | 1 | 3.75 | 461.3 |
| 313 | A43-M-B23 | 1 | 3.21 | 421.2 |
| 314 | A43-M-B24 | 1 | 3.5 | 447.3 |
| 315 | A43-M-B25 | 1 | 2.95 | 407.2 |
| 316 | A43-M-B26 | 1 | 3.25 | 433.2 |
| 317 | A43-M-B27 | 1 | 2.83 | 405.2 |
| 318 | A43-M-B7 | 1 | 2.66 | 423.2 |
| 319 | A44-M-B13 | 1 | 2.26 | 429.3 |
| 320 | A44-M-B14 | 1 | 2.74 | 381.3 |
| 321 | A44-M-B15 | 1 | 2.54 | 347.3 |
| 322 | A44-M-B16 | 1 | 2.98 | 395.3 |
| 323 | A44-M-B17 | 1 | 2.04 | 319.3 |
| 324 | A44-M-B20 | 1 | 3.02 | 395.3 |
| 325 | A44-M-B21 | 1 | 3.08 | 395.3 |
| 326 | A44-M-B22 | 1 | 3.3 | 387.3 |
| 327 | A44-M-B25 | 1 | 2.29 | 333.3 |
| 328 | A44-M-B26 | 1 | 2.65 | 359.3 |
| 329 | A45-M-B12 | 1 | 2.66 | 391.3 |
| 330 | A45-M-B13 | 1 | 2.77 | 349.3 |
| 331 | A45-M-B14 | 1 | 3.21 | 397.3 |
| 332 | A45-M-B15 | 1 | 3.05 | 363.3 |
| 333 | A45-M-B17 | 1 | 2.52 | 335.3 |
| 334 | A45-M-B20 | 1 | 3.45 | 411.3 |
| 335 | A45-M-B21 | 1 | 3.5 | 411.3 |
| 336 | A45-M-B22 | 1 | 3.72 | 403.4 |
| 337 | A45-M-B25 | 1 | 2.81 | 349.3 |
| 338 | A45-M-B26 | 1 | 3.15 | 375.3 |
| 339 | A45-M-B7 | 1 | 2.46 | 365.3 |
| 340 | A46-M-B12 | 1 | 2.34 | 422.3 |
| 341 | A46-M-B13 | 1 | 2.4 | 380.3 |
| 342 | A46-M-B14 | 1 | 2.8 | 428.3 |
| 343 | A46-M-B15 | 1 | 2.65 | 394.3 |
| 344 | A46-M-B16 | 1 | 3.03 | 442.3 |
| 345 | A46-M-B17 | 1 | 2.21 | 366.2 |
| 346 | A46-M-B18 | 1 | 3.25 | 434.3 |
| 347 | A46-M-B19 | 1 | 2.23 | 378.2 |
| 348 | A46-M-B20 | 1 | 3.04 | 442.3 |
| 349 | A46-M-B25 | 1 | 2.42 | 380.3 |
| 350 | A46-M-B26 | 1 | 2.73 | 406.3 |
| 351 | A46-M-B27 | 1 | 2.32 | 378.2 |
| 352 | A46-M-B7 | 1 | 2.18 | 396.3 |
| 353 | A47-M-B13 | 1 | 2.61 | 369.3 |
| 354 | A47-M-B14 | 1 | 3.06 | 417.3 |
| 355 | A47-M-B15 | 1 | 2.89 | 383.3 |
| 356 | A47-M-B16 | 1 | 3.26 | 431.3 |
| 357 | A47-M-B17 | 1 | 2.38 | 355.3 |
| 358 | A47-M-B18 | 1 | 3.58 | 423.3 |
| 359 | A47-M-B19 | 1 | 2.4 | 367.3 |
| 360 | A47-M-B20 | 1 | 3.31 | 431.3 |
| 361 | A47-M-B21 | 1 | 3.35 | 431.3 |
| 362 | A47-M-B22 | 1 | 3.55 | 423.3 |
| 363 | A47-M-B23 | 1 | 2.92 | 383.3 |
| 364 | A47-M-B24 | 1 | 3.27 | 409.3 |
| 365 | A47-M-B25 | 1 | 2.64 | 369.3 |
| 366 | A47-M-B26 | 1 | 2.99 | 395.3 |
| 367 | A47-M-B27 | 1 | 2.52 | 367.3 |
| 368 | A47-M-B7 | 1 | 2.35 | 385.3 |
| 369 | A48-M-B12 | 1 | 2.77 | 411.3 |
| 370 | A48-M-B13 | 1 | 2.84 | 369.3 |
| 371 | A48-M-B14 | 1 | 3.23 | 417.3 |
| 372 | A48-M-B15 | 1 | 3.09 | 383.3 |
| 373 | A48-M-B16 | 1 | 3.44 | 431.3 |
| 374 | A48-M-B17 | 1 | 2.64 | 355.3 |
| 375 | A48-M-B19 | 1 | 2.67 | 367.3 |
| 376 | A48-M-B20 | 1 | 3.45 | 431.3 |
| 377 | A48-M-B21 | 1 | 3.48 | 431.3 |
| 378 | A48-M-B22 | 1 | 3.67 | 423.3 |
| 379 | A48-M-B26 | 1 | 3.16 | 395.3 |

| Entry | Compound | HPLC Method | HPLC Rt (min) | [M + H]+ | Entry | Compound | HPLC Method | HPLC Rt (min) | [M + H]+ |
|---|---|---|---|---|---|---|---|---|---|
| 380 | A48-M-B7 | 1 | 2.6 | 385.3 | 456 | A55-M-B18 | 1 | 3.51 | 445.3 |
| 381 | A49-M-B12 | 1 | 2.78 | 403.3 | 457 | A55-M-B19 | 1 | 2.43 | 389.2 |
| 382 | A49-M-B13 | 1 | 2.89 | 361.3 | 458 | A55-M-B20 | 1 | 3.29 | 453.3 |
| 383 | A49-M-B14 | 1 | 3.31 | 409.3 | 459 | A55-M-B21 | 1 | 3.33 | 453.3 |
| 384 | A49-M-B15 | 1 | 3.16 | 375.3 | 460 | A55-M-B22 | 1 | 3.53 | 445.3 |
| 385 | A49-M-B16 | 1 | 3.51 | 423.3 | 461 | A55-M-B23 | 1 | 2.93 | 405.3 |
| 386 | A49-M-B17 | 1 | 2.66 | 347.3 | 462 | A55-M-B25 | 1 | 2.65 | 391.3 |
| 387 | A49-M-B18 | 1 | 3.82 | 415.4 | 463 | A55-M-B26 | 1 | 2.98 | 417.3 |
| 388 | A49-M-B19 | 1 | 2.68 | 359.3 | 464 | A55-M-B27 | 1 | 2.53 | 389.2 |
| 389 | A49-M-B20 | 1 | 3.56 | 423.3 | 465 | A55-M-B7 | 1 | 2.36 | 407.2 |
| 390 | A49-M-B21 | 1 | 3.59 | 423.3 | 466 | A56-M-B13 | 1 | 2.99 | 391.3 |
| 391 | A49-M-B22 | 1 | 3.79 | 415.4 | 467 | A56-M-B14 | 1 | 3.38 | 439.3 |
| 392 | A49-M-B23 | 1 | 3.2 | 375.3 | 468 | A56-M-B15 | 1 | 3.23 | 405.3 |
| 393 | A49-M-B24 | 1 | 3.53 | 401.3 | 469 | A56-M-B16 | 1 | 3.58 | 453.3 |
| 394 | A49-M-B25 | 1 | 2.92 | 361.3 | 470 | A56-M-B18 | 1 | 3.86 | 445.3 |
| 395 | A49-M-B26 | 1 | 3.26 | 387.3 | 471 | A56-M-B19 | 1 | 2.79 | 389.2 |
| 396 | A49-M-B27 | 1 | 2.8 | 359.3 | 472 | A56-M-B20 | 1 | 3.61 | 453.3 |
| 397 | A49-M-B7 | 1 | 2.6 | 377.3 | 473 | A56-M-B21 | 1 | 3.62 | 453.3 |
| 398 | A50-M-B12 | 1 | 2.58 | 391.3 | 474 | A56-M-B22 | 1 | 3.81 | 445.3 |
| 399 | A50-M-B13 | 1 | 2.66 | 349.3 | 475 | A56-M-B23 | 1 | 3.28 | 405.3 |
| 400 | A50-M-B14 | 1 | 3.15 | 397.3 | 476 | A56-M-B24 | 1 | 3.59 | 431.3 |
| 401 | A50-M-B15 | 1 | 2.95 | 363.3 | 477 | A56-M-B25 | 1 | 3.01 | 391.3 |
| 402 | A50-M-B16 | 1 | 3.33 | 411.3 | 478 | A56-M-B26 | 1 | 3.33 | 417.3 |
| 403 | A50-M-B17 | 1 | 2.4 | 335.3 | 479 | A56-M-B27 | 1 | 2.89 | 389.2 |
| 404 | A50-M-B20 | 1 | 3.39 | 411.3 | 480 | A56-M-B7 | 1 | 2.7 | 407.2 |
| 405 | A50-M-B21 | 1 | 3.44 | 411.3 | 481 | A57-M-B12 | 1 | 3.09 | 425.3 |
| 406 | A50-M-B22 | 1 | 3.66 | 403.4 | 482 | A57-M-B13 | 1 | 3.2 | 383.3 |
| 407 | A50-M-B25 | 1 | 2.72 | 349.3 | 483 | A57-M-B14 | 1 | 3.53 | 431.3 |
| 408 | A50-M-B26 | 1 | 3.06 | 375.3 | 484 | A57-M-B15 | 1 | 3.42 | 397.3 |
| 409 | A51-M-B12 | 1 | 2.37 | 377.3 | 485 | A57-M-B16 | 1 | 3.71 | 445.3 |
| 410 | A51-M-B13 | 1 | 2.44 | 335.3 | 486 | A57-M-B18 | 1 | 3.97 | 437.3 |
| 411 | A51-M-B14 | 1 | 2.91 | 383.3 | 487 | A57-M-B19 | 1 | 3.05 | 381.3 |
| 412 | A51-M-B15 | 1 | 2.73 | 349.3 | 488 | A57-M-B20 | 1 | 3.73 | 445.3 |
| 413 | A51-M-B16 | 1 | 3.15 | 397.3 | 489 | A57-M-B21 | 1 | 3.74 | 445.3 |
| 414 | A51-M-B17 | 1 | 2.2 | 321.3 | 490 | A57-M-B22 | 2 | 5.77 | 437.3 |
| 415 | A51-M-B22 | 1 | 3.48 | 389.3 | 491 | A57-M-B23 | 1 | 3.45 | 397.3 |
| 416 | A51-M-B25 | 1 | 2.47 | 335.3 | 492 | A57-M-B24 | 1 | 3.72 | 423.3 |
| 417 | A51-M-B26 | 1 | 2.83 | 361.3 | 493 | A57-M-B25 | 1 | 3.23 | 383.3 |
| 418 | A51-M-B27 | 1 | 2.34 | 333.3 | 494 | A57-M-B26 | 1 | 3.49 | 409.3 |
| 419 | A52-M-B12 | 1 | 2.89 | 425.3 | 495 | A57-M-B27 | 1 | 3.13 | 381.3 |
| 420 | A52-M-B13 | 1 | 2.99 | 383.3 | 496 | A57-M-B7 | 1 | 2.95 | 399.3 |
| 421 | A52-M-B14 | 1 | 3.38 | 431.3 | 497 | A58-M-B13 | 1 | 2.53 | 375.2 |
| 422 | A52-M-B15 | 1 | 3.24 | 397.3 | 498 | A58-M-B15 | 1 | 2.8 | 389.3 |
| 423 | A52-M-B16 | 1 | 3.56 | 445.3 | 499 | A58-M-B16 | 1 | 3.16 | 437.3 |
| 424 | A52-M-B18 | 1 | 3.83 | 437.3 | 500 | A58-M-B17 | 1 | 2.32 | 361.2 |
| 425 | A52-M-B19 | 1 | 2.8 | 381.3 | 501 | A58-M-B20 | 1 | 3.19 | 437.3 |
| 426 | A52-M-B20 | 1 | 3.59 | 445.3 | 502 | A58-M-B21 | 1 | 3.21 | 437.3 |
| 427 | A52-M-B21 | 1 | 3.62 | 445.3 | 503 | A58-M-B25 | 1 | 2.56 | 375.2 |
| 428 | A52-M-B22 | 1 | 3.82 | 437.3 | 504 | A58-M-B26 | 1 | 2.88 | 401.3 |
| 429 | A52-M-B23 | 1 | 3.28 | 397.3 | 505 | A59-M-B12 | 1 | 2.67 | 449.2 |
| 430 | A52-M-B24 | 1 | 3.57 | 423.3 | 506 | A59-M-B13 | 1 | 2.75 | 407.2 |
| 431 | A52-M-B25 | 1 | 3.03 | 383.3 | 507 | A59-M-B14 | 1 | 3.19 | 455.2 |
| 432 | A52-M-B26 | 1 | 3.33 | 409.3 | 508 | A59-M-B15 | 1 | 3.01 | 421.2 |
| 433 | A52-M-B27 | 1 | 2.91 | 381.3 | 509 | A59-M-B16 | 1 | 3.38 | 469.2 |
| 434 | A52-M-B7 | 1 | 2.72 | 399.3 | 510 | A59-M-B18 | 1 | 3.69 | 461.3 |
| 435 | A53-M-B12 | 1 | 2.26 | 433.3 | 511 | A59-M-B19 | 1 | 2.55 | 405.2 |
| 436 | A53-M-B13 | 1 | 2.31 | 391.3 | 512 | A59-M-B20 | 1 | 3.41 | 469.2 |
| 437 | A53-M-B14 | 1 | 2.75 | 439.3 | 513 | A59-M-B21 | 1 | 3.46 | 469.2 |
| 438 | A53-M-B15 | 1 | 2.57 | 405.3 | 514 | A59-M-B22 | 1 | 3.65 | 461.3 |
| 439 | A53-M-B16 | 1 | 2.98 | 453.3 | 515 | A59-M-B23 | 1 | 3.06 | 421.2 |
| 440 | A53-M-B20 | 1 | 3.01 | 453.3 | 516 | A59-M-B25 | 1 | 2.78 | 407.2 |
| 441 | A53-M-B21 | 1 | 3 | 453.3 | 517 | A59-M-B26 | 1 | 3.12 | 433.2 |
| 442 | A53-M-B26 | 1 | 2.65 | 417.3 | 518 | A59-M-B27 | 1 | 2.65 | 405.2 |
| 443 | A53-M-B7 | 1 | 2.08 | 407.2 | 519 | A59-M-B7 | 1 | 2.47 | 423.2 |
| 444 | A54-M-B13 | 1 | 2.38 | 335.3 | 520 | A60-M-B12 | 1 | 2.34 | 377.3 |
| 445 | A54-M-B14 | 1 | 2.88 | 383.3 | 521 | A60-M-B13 | 1 | 2.4 | 335.3 |
| 446 | A54-M-B15 | 1 | 2.67 | 349.3 | 522 | A60-M-B14 | 1 | 2.88 | 383.3 |
| 447 | A54-M-B20 | 1 | 3.15 | 397.3 | 523 | A60-M-B15 | 1 | 2.69 | 349.3 |
| 448 | A54-M-B21 | 1 | 3.2 | 397.3 | 524 | A60-M-B16 | 1 | 3.1 | 397.3 |
| 449 | A54-M-B26 | 1 | 2.78 | 361.3 | 525 | A60-M-B20 | 1 | 3.15 | 397.3 |
| 450 | A55-M-B12 | 1 | 2.55 | 433.3 | 526 | A60-M-B21 | 1 | 3.21 | 397.3 |
| 451 | A55-M-B13 | 1 | 2.62 | 391.3 | 527 | A60-M-B22 | 1 | 3.44 | 389.3 |
| 452 | A55-M-B14 | 1 | 3.06 | 439.3 | 528 | A60-M-B23 | 1 | 2.73 | 349.3 |
| 453 | A55-M-B15 | 1 | 2.88 | 405.3 | 529 | A60-M-B25 | 1 | 2.43 | 335.3 |
| 454 | A55-M-B16 | 1 | 3.26 | 453.3 | 530 | A60-M-B26 | 1 | 2.81 | 361.3 |
| 455 | A55-M-B17 | 1 | 2.4 | 377.2 | 531 | A60-M-B27 | 1 | 2.3 | 333.3 |

-continued

| Entry | Compound | HPLC Method | HPLC Rt (min) | [M + H]⁺ |
|---|---|---|---|---|
| 532 | A61-M-B13 | 1 | 2.52 | 335.3 |
| 533 | A61-M-B14 | 1 | 2.98 | 383.3 |
| 534 | A61-M-B15 | 1 | 2.8 | 349.3 |
| 535 | A61-M-B16 | 1 | 3.2 | 397.3 |
| 536 | A61-M-B17 | 1 | 2.27 | 321.3 |
| 537 | A61-M-B19 | 1 | 2.31 | 333.3 |
| 538 | A61-M-B20 | 1 | 3.25 | 397.3 |
| 539 | A61-M-B21 | 1 | 3.3 | 397.3 |
| 540 | A61-M-B26 | 1 | 2.9 | 361.3 |
| 541 | A62-M-B12 | 1 | 2.42 | 397.3 |
| 542 | A62-M-B13 | 1 | 2.49 | 355.3 |
| 543 | A62-M-B14 | 1 | 2.91 | 403.3 |
| 544 | A62-M-B15 | 1 | 2.75 | 369.3 |
| 545 | A62-M-B16 | 1 | 3.13 | 417.3 |
| 546 | A62-M-B17 | 1 | 2.26 | 341.3 |
| 547 | A62-M-B18 | 1 | 3.46 | 409.3 |
| 548 | A62-M-B19 | 1 | 2.29 | 353.3 |
| 549 | A62-M-B20 | 1 | 3.16 | 417.3 |
| 550 | A62-M-B21 | 1 | 3.2 | 417.3 |
| 551 | A62-M-B22 | 1 | 3.39 | 409.3 |
| 552 | A62-M-B23 | 1 | 2.78 | 369.3 |
| 553 | A62-M-B24 | 1 | 3.12 | 395.3 |
| 554 | A62-M-B25 | 1 | 2.51 | 355.3 |
| 555 | A62-M-B26 | 1 | 2.83 | 381.3 |
| 556 | A62-M-B27 | 1 | 2.38 | 353.3 |
| 557 | A62-M-B7 | 1 | 2.24 | 371.3 |
| 558 | A63-M-B12 | 1 | 2.96 | 429.3 |
| 559 | A63-M-B13 | 1 | 3.07 | 387.3 |
| 560 | A63-M-B14 | 1 | 3.41 | 435.3 |
| 561 | A63-M-B15 | 1 | 3.3 | 401.3 |
| 562 | A63-M-B16 | 1 | 3.6 | 449.3 |
| 563 | A63-M-B17 | 1 | 2.86 | 373.3 |
| 564 | A63-M-B18 | 1 | 3.88 | 441.3 |
| 565 | A63-M-B19 | 1 | 2.89 | 385.3 |
| 566 | A63-M-B20 | 1 | 3.63 | 449.3 |
| 567 | A63-M-B21 | 1 | 3.64 | 449.3 |
| 568 | A63-M-B22 | 1 | 3.83 | 441.3 |
| 569 | A63-M-B26 | 1 | 3.38 | 413.3 |
| 570 | A63-M-B27 | 1 | 2.99 | 385.3 |
| 571 | A63-M-B7 | 1 | 2.82 | 403.3 |
| 572 | A64-M-B12 | 1 | 2.34 | 415.3 |
| 573 | A64-M-B14 | 1 | 2.84 | 421.3 |
| 574 | A64-M-B15 | 1 | 2.67 | 387.3 |
| 575 | A64-M-B16 | 1 | 3.06 | 435.3 |
| 576 | A64-M-B17 | 1 | 2.22 | 359.2 |
| 577 | A64-M-B20 | 1 | 3.09 | 435.3 |
| 578 | A64-M-B21 | 1 | 3.13 | 435.3 |
| 579 | A64-M-B22 | 1 | 3.33 | 427.3 |
| 580 | A64-M-B26 | 1 | 2.75 | 399.3 |
| 581 | A64-M-B27 | 1 | 2.34 | 371.2 |
| 582 | A64-M-B7 | 1 | 2.19 | 389.3 |
| 583 | A65-M-B12 | 1 | 2.51 | 389.3 |
| 584 | A65-M-B14 | 1 | 3.05 | 395.3 |
| 585 | A65-M-B15 | 1 | 2.86 | 361.3 |
| 586 | A65-M-B16 | 1 | 3.26 | 409.3 |
| 587 | A65-M-B17 | 1 | 2.34 | 333.3 |
| 588 | A65-M-B18 | 1 | 3.59 | 401.3 |
| 589 | A65-M-B19 | 1 | 2.37 | 345.3 |
| 590 | A65-M-B20 | 1 | 3.3 | 409.3 |
| 591 | A65-M-B21 | 1 | 3.34 | 409.3 |
| 592 | A65-M-B22 | 1 | 3.57 | 401.3 |
| 593 | A65-M-B26 | 1 | 2.97 | 373.3 |
| 594 | A65-M-B7 | 1 | 2.3 | 363.3 |
| 595 | A66-M-B12 | 1 | 2.56 | 449.2 |
| 596 | A66-M-B14 | 1 | 3.08 | 455.2 |
| 597 | A66-M-B15 | 1 | 2.9 | 421.2 |
| 598 | A66-M-B16 | 1 | 3.29 | 469.2 |
| 599 | A66-M-B20 | 1 | 3.32 | 469.2 |
| 600 | A66-M-B21 | 1 | 3.35 | 469.2 |
| 601 | A66-M-B25 | 1 | 2.66 | 407.2 |
| 602 | A66-M-B26 | 1 | 3.02 | 433.2 |
| 603 | A67-M-B12 | 1 | 2.5 | 433.3 |
| 604 | A67-M-B14 | 1 | 3 | 439.3 |
| 605 | A67-M-B15 | 1 | 2.84 | 405.3 |
| 606 | A67-M-B16 | 1 | 3.21 | 453.3 |
| 607 | A67-M-B18 | 1 | 3.45 | 445.3 |
| 608 | A67-M-B19 | 1 | 2.37 | 389.2 |
| 609 | A67-M-B20 | 1 | 3.24 | 453.3 |
| 610 | A67-M-B21 | 1 | 3.28 | 453.3 |
| 611 | A67-M-B26 | 1 | 2.92 | 417.3 |
| 612 | A67-M-B27 | 1 | 2.49 | 389.2 |
| 613 | A67-M-B7 | 1 | 2.32 | 407.2 |
| 614 | A68-M-B12 | 1 | 2.43 | 431.2 |
| 615 | A68-M-B14 | 1 | 2.95 | 437.2 |
| 616 | A68-M-B15 | 1 | 2.78 | 403.2 |
| 617 | A68-M-B16 | 1 | 3.17 | 451.2 |
| 618 | A68-M-B17 | 1 | 2.29 | 375.2 |
| 619 | A68-M-B18 | 1 | 3.47 | 443.3 |
| 620 | A68-M-B19 | 1 | 2.31 | 387.2 |
| 621 | A68-M-B20 | 1 | 3.19 | 451.2 |
| 622 | A68-M-B21 | 1 | 3.24 | 451.2 |
| 623 | A68-M-B26 | 1 | 2.87 | 415.2 |
| 624 | A68-M-B27 | 1 | 2.41 | 387.2 |
| 625 | A68-M-B7 | 1 | 2.25 | 405.2 |
| 626 | A69-M-B14 | 1 | 2.61 | 369.3 |
| 627 | A69-M-B15 | 1 | 2.38 | 335.3 |
| 628 | A69-M-B16 | 1 | 2.85 | 383.3 |
| 629 | A69-M-B20 | 1 | 2.9 | 383.3 |
| 630 | A69-M-B21 | 1 | 2.95 | 383.3 |
| 631 | A69-M-B25 | 1 | 2.15 | 321.3 |
| 632 | A69-M-B26 | 1 | 2.5 | 347.3 |
| 633 | A70-M-B12 | 1 | 2.62 | 415.3 |
| 634 | A70-M-B14 | 1 | 3.12 | 421.3 |
| 635 | A70-M-B15 | 1 | 2.97 | 387.3 |
| 636 | A70-M-B16 | 1 | 3.33 | 435.3 |
| 637 | A70-M-B17 | 1 | 2.48 | 359.2 |
| 638 | A70-M-B18 | 1 | 3.63 | 427.3 |
| 639 | A70-M-B19 | 1 | 2.5 | 371.2 |
| 640 | A70-M-B20 | 1 | 3.35 | 435.3 |
| 641 | A70-M-B21 | 1 | 3.37 | 435.3 |
| 642 | A70-M-B26 | 1 | 3.06 | 399.3 |
| 643 | A70-M-B27 | 1 | 2.61 | 371.2 |
| 644 | A70-M-B7 | 1 | 2.43 | 389.3 |
| 645 | A71-M-B14 | 1 | 2.58 | 369.3 |
| 646 | A71-M-B16 | 1 | 2.84 | 383.3 |
| 647 | A71-M-B20 | 1 | 2.87 | 383.3 |
| 648 | A71-M-B21 | 1 | 2.93 | 383.3 |
| 649 | A71-M-B25 | 1 | 2.11 | 321.3 |
| 650 | A72-M-B14 | 1 | 2.52 | 421.3 |
| 651 | A72-M-B16 | 1 | 2.74 | 435.3 |
| 652 | A72-M-B18 | 1 | 3.06 | 427.3 |
| 653 | A72-M-B20 | 1 | 2.75 | 435.3 |
| 654 | A72-M-B21 | 1 | 2.77 | 435.3 |
| 655 | A72-M-B27 | 1 | 2.07 | 371.2 |
| 656 | A73-M-B12 | 1 | 2.66 | 430.3 |
| 657 | A73-M-B14 | 1 | 3.17 | 436.3 |
| 658 | A73-M-B17 | 1 | 2.17 | 374.3 |
| 659 | A73-M-B20 | 1 | 3.4 | 450.3 |
| 660 | A73-M-B21 | 1 | 3.45 | 450.3 |
| 661 | A73-M-B24 | 1 | 3.38 | 428.3 |
| 662 | A73-M-B26 | 1 | 3.11 | 414.3 |
| 663 | A74-M-B16 | 1 | 2.87 | 453.3 |
| 664 | A74-M-B17 | 1 | 2.04 | 377.2 |
| 665 | A75-M-B18 | 1 | 2.95 | 399.3 |
| 666 | A75-M-B19 | 1 | 1.91 | 343.2 |
| 667 | A75-M-B20 | 1 | 2.72 | 407.3 |
| 668 | A75-M-B21 | 1 | 2.75 | 407.3 |
| 669 | A75-M-B22 | 1 | 2.98 | 399.3 |
| 670 | A75-M-B23 | 1 | 2.34 | 359.3 |
| 671 | A75-M-B24 | 1 | 2.68 | 385.3 |
| 672 | A75-M-B25 | 1 | 2.09 | 345.2 |
| 673 | A75-M-B27 | 1 | 1.98 | 343.2 |
| 674 | A76-M-B18 | 1 | 2.69 | 410.3 |
| 675 | A76-M-B19 | 1 | 1.7 | 354.2 |
| 676 | A76-M-B20 | 1 | 2.45 | 418.3 |
| 677 | A76-M-B21 | 1 | 2.5 | 418.3 |
| 678 | A76-M-B22 | 1 | 2.72 | 410.3 |
| 679 | A76-M-B23 | 1 | 2.06 | 370.3 |
| 680 | A76-M-B24 | 1 | 2.4 | 396.3 |
| 681 | A76-M-B25 | 1 | 1.85 | 356.3 |
| 682 | A77-M-B14 | 1 | 2.64 | 421.3 |
| 683 | A77-M-B16 | 1 | 2.9 | 435.3 |

-continued

| Entry | Compound | HPLC Method | HPLC Rt (min) | [M + H]+ |
|---|---|---|---|---|
| 684 | A77-M-B18 | 1 | 3.2 | 427.3 |
| 685 | A77-M-B20 | 1 | 2.89 | 435.3 |
| 686 | A77-M-B21 | 1 | 2.92 | 435.3 |
| 687 | A77-M-B27 | 1 | 2.19 | 371.3 |
| 688 | A78-M-B12 | 1 | 2.69 | 442.3 |
| 689 | A78-M-B14 | 1 | 3.16 | 448.3 |
| 690 | A78-M-B15 | 1 | 3.02 | 414.3 |
| 691 | A78-M-B16 | 1 | 3.38 | 462.3 |
| 692 | A78-M-B17 | 1 | 2.57 | 386.3 |
| 693 | A78-M-B18 | 1 | 3.65 | 454.3 |
| 694 | A78-M-B19 | 1 | 2.59 | 398.3 |
| 695 | A78-M-B20 | 1 | 3.38 | 462.3 |
| 696 | A78-M-B21 | 1 | 3.42 | 462.3 |
| 697 | A78-M-B22 | 1 | 3.62 | 454.3 |
| 698 | A78-M-B23 | 1 | 3.07 | 414.3 |
| 699 | A78-M-B24 | 1 | 3.37 | 440.3 |
| 700 | A78-M-B26 | 1 | 3.12 | 426.3 |
| 701 | A78-M-B7 | 1 | 2.51 | 416.3 |
| 702 | A79-M-B14 | 1 | 3.69 | 466.3 |
| 703 | A79-M-B18 | 1 | 4.09 | 472.3 |
| 704 | A79-M-B21 | 1 | 3.9 | 480.3 |
| 705 | A79-M-B22 | 1 | 4.07 | 472.3 |
| 706 | A79-M-B24 | 1 | 3.86 | 458.3 |
| 707 | A79-M-B26 | 1 | 3.65 | 444.3 |
| 708 | A80-M-B14 | 1 | 3.66 | 470.2 |
| 709 | A80-M-B15 | 1 | 3.56 | 436.2 |
| 710 | A80-M-B18 | 1 | 4.06 | 476.3 |
| 711 | A80-M-B19 | 1 | 3.19 | 420.2 |
| 712 | A80-M-B21 | 1 | 3.87 | 484.2 |
| 713 | A80-M-B22 | 1 | 4.04 | 476.3 |
| 714 | A80-M-B24 | 1 | 3.87 | 462.3 |
| 715 | A81-M-B14 | 1 | 3.64 | 466.3 |
| 716 | A81-M-B18 | 1 | 4.06 | 472.3 |
| 717 | A81-M-B19 | 1 | 3.11 | 416.2 |
| 718 | A81-M-B21 | 1 | 3.88 | 480.3 |
| 719 | A81-M-B22 | 1 | 4.06 | 472.3 |
| 720 | A81-M-B24 | 1 | 3.83 | 458.3 |
| 721 | A82-M-B14 | 1 | 3.4 | 446.3 |
| 722 | A82-M-B18 | 1 | 3.86 | 452.4 |
| 723 | A82-M-B19 | 1 | 2.8 | 396.3 |
| 724 | A82-M-B20 | 1 | 3.62 | 460.3 |
| 725 | A82-M-B21 | 1 | 3.66 | 460.3 |
| 726 | A82-M-B22 | 1 | 3.86 | 452.4 |
| 727 | A82-M-B24 | 1 | 3.59 | 438.3 |
| 728 | A83-M-B14 | 1 | 3.45 | 446.3 |
| 729 | A83-M-B18 | 1 | 3.89 | 452.4 |
| 730 | A83-M-B19 | 1 | 2.87 | 396.3 |
| 731 | A83-M-B20 | 1 | 3.65 | 460.3 |
| 732 | A83-M-B22 | 1 | 3.89 | 452.4 |
| 733 | A83-M-B24 | 1 | 3.64 | 438.3 |
| 734 | A84-M-B14 | 1 | 3.03 | 432.3 |
| 735 | A84-M-B18 | 1 | 3.58 | 438.3 |
| 736 | A84-M-B19 | 1 | 2.38 | 382.3 |
| 737 | A84-M-B20 | 1 | 3.27 | 446.3 |
| 738 | A84-M-B21 | 1 | 3.32 | 446.3 |
| 739 | A84-M-B22 | 1 | 3.54 | 438.3 |
| 740 | A85-M-B14 | 1 | 3.56 | 450.3 |
| 741 | A85-M-B17 | 1 | 3.04 | 388.3 |
| 742 | A85-M-B20 | 1 | 3.76 | 464.3 |
| 743 | A85-M-B21 | 1 | 3.79 | 464.3 |
| 744 | A85-M-B22 | 2 | 5.71 | 456.3 |
| 745 | A86-M-B14 | 1 | 3.02 | 410.3 |
| 746 | A86-M-B20 | 1 | 3.27 | 424.3 |
| 747 | A86-M-B21 | 1 | 3.32 | 424.3 |
| 748 | A86-M-B25 | 1 | 2.61 | 362.3 |
| 749 | A87-M-B14 | 1 | 3.33 | 446.3 |
| 750 | A87-M-B20 | 1 | 3.55 | 460.3 |
| 751 | A88-M-B14 | 1 | 3.31 | 454.3 |
| 752 | A88-M-B16 | 1 | 3.49 | 468.3 |
| 753 | A88-M-B17 | 1 | 2.63 | 392.2 |
| 754 | A88-M-B19 | 1 | 2.66 | 404.2 |
| 755 | A88-M-B20 | 1 | 3.53 | 468.3 |
| 756 | A88-M-B21 | 1 | 3.57 | 468.3 |
| 757 | A89-M-B14 | 1 | 2.64 | 422.3 |
| 758 | A89-M-B20 | 1 | 2.91 | 436.3 |
| 759 | A89-M-B21 | 1 | 2.97 | 436.3 |

-continued

| Entry | Compound | HPLC Method | HPLC Rt (min) | [M + H]+ |
|---|---|---|---|---|
| 760 | A90-M-B13 | 1 | 1.89 | 349.3 |
| 761 | A90-M-B16 | 1 | 2.56 | 411.3 |
| 762 | A90-M-B20 | 1 | 2.6 | 411.3 |
| 763 | A90-M-B21 | 1 | 2.68 | 411.3 |
| 764 | A91-M-B14 | 1 | 2.4 | 407.3 |
| 765 | A91-M-B16 | 1 | 2.68 | 421.3 |
| 766 | A91-M-B18 | 1 | 2.99 | 413.3 |
| 767 | A91-M-B20 | 1 | 2.65 | 421.3 |
| 768 | A91-M-B21 | 1 | 2.69 | 421.3 |
| 769 | A91-M-B26 | 1 | 2.35 | 385.3 |
| 770 | A92-M-B12 | 1 | 3.15 | 446.3 |
| 771 | A92-M-B14 | 1 | 3.58 | 452.2 |
| 772 | A92-M-B17 | 1 | 3.05 | 390.2 |
| 773 | A92-M-B20 | 1 | 3.78 | 466.3 |
| 774 | A92-M-B21 | 1 | 3.8 | 466.3 |
| 775 | A92-M-B22 | 1 | 3.97 | 458.3 |
| 776 | A92-M-B24 | 1 | 3.78 | 444.3 |
| 777 | A92-M-B26 | 1 | 3.56 | 430.3 |
| 778 | A92-M-B7 | 1 | 2.98 | 420.2 |
| 779 | A93-M-B14 | 1 | 3.41 | 452.2 |
| 780 | A93-M-B16 | 1 | 3.6 | 466.3 |
| 781 | A93-M-B17 | 1 | 2.82 | 390.2 |
| 782 | A93-M-B20 | 1 | 3.63 | 466.3 |
| 783 | A93-M-B21 | 1 | 3.66 | 466.3 |
| 784 | A93-M-B22 | 1 | 3.85 | 458.3 |
| 785 | A93-M-B24 | 1 | 3.63 | 444.3 |
| 786 | A93-M-B26 | 1 | 3.37 | 430.3 |
| 787 | A93-M-B27 | 1 | 2.96 | 402.2 |
| 788 | A93-M-B7 | 1 | 2.76 | 420.2 |
| 789 | A94-M-B14 | 1 | 3.58 | 452.2 |
| 790 | A94-M-B17 | 1 | 3.04 | 390.2 |
| 791 | A94-M-B21 | 1 | 3.81 | 466.3 |
| 792 | A94-M-B24 | 1 | 3.78 | 444.3 |
| 793 | A94-M-B26 | 1 | 3.55 | 430.3 |
| 794 | A95-M-B14 | 1 | 3.16 | 432.3 |
| 795 | A95-M-B20 | 1 | 3.39 | 446.3 |
| 796 | A95-M-B21 | 1 | 3.45 | 446.3 |
| 797 | A95-M-B24 | 1 | 3.37 | 424.3 |
| 798 | A95-M-B26 | 1 | 3.09 | 410.3 |
| 799 | A96-M-B14 | 1 | 3.36 | 432.3 |
| 800 | A96-M-B20 | 1 | 3.58 | 446.3 |
| 801 | A96-M-B21 | 1 | 3.62 | 446.3 |
| 802 | A96-M-B22 | 1 | 3.81 | 438.3 |
| 803 | A96-M-B24 | 1 | 3.57 | 424.3 |
| 804 | A97-M-B12 | 1 | 2.59 | 442.3 |
| 805 | A97-M-B14 | 1 | 3.1 | 448.3 |
| 806 | A97-M-B16 | 1 | 3.26 | 462.3 |
| 807 | A97-M-B17 | 1 | 2.46 | 386.3 |
| 808 | A97-M-B18 | 1 | 3.56 | 454.3 |
| 809 | A97-M-B20 | 1 | 3.29 | 462.3 |
| 810 | A97-M-B22 | 1 | 3.52 | 454.3 |
| 811 | A97-M-B24 | 1 | 3.26 | 440.3 |
| 812 | A97-M-B26 | 1 | 3.02 | 426.3 |
| 813 | A98-M-B14 | 1 | 2.97 | 443.3 |
| 814 | A98-M-B17 | 1 | 2.4 | 381.3 |
| 815 | A98-M-B20 | 1 | 3.2 | 457.3 |
| 816 | A98-M-B22 | 1 | 3.4 | 449.3 |
| 817 | A98-M-B24 | 1 | 3.21 | 435.3 |
| 818 | A98-M-B7 | 1 | 2.35 | 411.3 |
| 819 | A99-M-B14 | 1 | 3.86 | 466.3 |
| 820 | A99-M-B20 | 1 | 3.99 | 480.3 |
| 821 | A99-M-B22 | 1 | 4.17 | 472.3 |
| 822 | A99-M-B24 | 1 | 3.98 | 458.3 |
| 823 | A99-M-B26 | 1 | 3.79 | 444.3 |
| 824 | A100-M-B14 | 1 | 3.65 | 446.3 |
| 825 | A100-M-B22 | 1 | 4.04 | 452.4 |
| 826 | A100-M-B24 | 1 | 3.84 | 438.3 |
| 827 | A100-M-B26 | 1 | 3.62 | 424.3 |
| 828 | A101-M-B14 | 1 | 3.33 | 412.3 |
| 829 | A101-M-B19 | 1 | 2.71 | 362.3 |
| 830 | A101-M-B20 | 1 | 3.54 | 426.3 |
| 831 | A101-M-B21 | 1 | 3.59 | 426.3 |
| 832 | A101-M-B22 | 1 | 3.8 | 418.4 |
| 833 | A102-M-B14 | 1 | 3.29 | 436.3 |
| 834 | A102-M-B17 | 1 | 2.67 | 374.3 |
| 835 | A102-M-B19 | 1 | 2.69 | 386.3 |

-continued

| Entry | Compound | HPLC Method | HPLC Rt (min) | [M + H]+ |
|---|---|---|---|---|
| 836 | A102-M-B20 | 1 | 3.51 | 450.3 |
| 837 | A102-M-B21 | 1 | 3.55 | 450.3 |
| 838 | A102-M-B22 | 1 | 3.74 | 442.3 |
| 839 | A103-M-B14 | 1 | 2.95 | 398.3 |
| 840 | A103-M-B20 | 1 | 3.21 | 412.3 |
| 841 | A103-M-B21 | 1 | 3.27 | 412.3 |
| 842 | A103-M-B22 | 1 | 3.5 | 404.4 |
| 843 | A104-M-B16 | 1 | 3.36 | 460.3 |
| 844 | A104-M-B22 | 1 | 3.68 | 452.4 |
| 845 | A105-M-B14 | 1 | 3.65 | 446.3 |
| 846 | A105-M-B20 | 1 | 3.83 | 460.3 |
| 847 | A105-M-B21 | 1 | 3.86 | 460.3 |
| 848 | A105-M-B22 | 1 | 4.05 | 452.4 |
| 849 | A106-M-B14 | 1 | 3.64 | 446.3 |
| 850 | A106-M-B16 | 1 | 3.82 | 460.3 |
| 851 | A106-M-B17 | 1 | 3.12 | 384.3 |
| 852 | A106-M-B20 | 1 | 3.85 | 460.3 |
| 853 | A106-M-B21 | 1 | 3.87 | 460.3 |
| 854 | A106-M-B24 | 1 | 3.84 | 438.3 |
| 855 | A106-M-B26 | 1 | 3.63 | 424.3 |
| 856 | A107-M-B14 | 1 | 3.67 | 466.3 |
| 857 | A107-M-B16 | 1 | 3.83 | 480.3 |
| 858 | A107-M-B24 | 1 | 3.91 | 458.3 |
| 859 | A107-M-B26 | 1 | 3.65 | 444.3 |
| 860 | A108-M-B20 | 1 | 3.81 | 437.3 |
| 861 | A108-M-B25 | 1 | 3.28 | 375.3 |
| 862 | A108-M-B27 | 1 | 3.17 | 373.3 |
| 863 | A109-M-B13 | 1 | 2.47 | 407.2 |
| 864 | A109-M-B16 | 1 | 3.12 | 469.2 |
| 865 | A110-M-B14 | 1 | 3.57 | 450.3 |
| 866 | A110-M-B17 | 1 | 3.03 | 388.3 |
| 867 | A110-M-B20 | 1 | 3.76 | 464.3 |
| 868 | A111-M-B14 | 1 | 3.59 | 454.3 |
| 869 | A111-M-B17 | 1 | 3.05 | 392.2 |
| 870 | A111-M-B22 | 1 | 3.99 | 460.3 |
| 871 | A112-M-B16 | 1 | 2.55 | 369.3 |
| 872 | A112-M-B21 | 1 | 2.64 | 369.3 |
| 873 | A113-M-B16 | 1 | 2.66 | 419.3 |
| 874 | A114-M-B16 | 1 | 2.38 | 405.3 |
| 875 | A115-M-B16 | 1 | 2.59 | 419.3 |
| 876 | A116-M-B20 | 1 | 2.39 | 385.3 |
| 877 | A116-M-B21 | 1 | 2.48 | 385.3 |
| 878 | A117-M-B20 | 1 | 2.59 | 428.3 |
| 879 | A118-M-B20 | 1 | 2.69 | 440.3 |
| 880 | A118-M-B21 | 1 | 2.76 | 440.3 |
| 881 | A119-M-B20 | 1 | 2.87 | 398.3 |
| 882 | A120-M-B21 | 1 | 3.32 | 412.3 |
| 883 | A121-M-B21 | 1 | 2.53 | 414.3 |
| 884 | A122-M-B21 | 1 | 2.03 | 433.3 |
| 885 | A122-M-B22 | 1 | 2.21 | 425.3 |
| 886 | A123-M-B25 | 1 | 2.16 | 345.2 |
| 887 | A20-M-B14 | 1 | 3.92 | 394.2 |
| 888 | A20-M-B17 | 1 | 3.41 | 332.2 |
| 889 | A20-M-B19 | 1 | 3.41 | 344.2 |
| 890 | A20-M-B24 | 1 | 4.09 | 386.3 |
| 891 | A20-M-B25 | 1 | 3.63 | 346.2 |
| 892 | A20-M-B26 | 1 | 3.88 | 372.2 |
| 893 | A20-M-B31 | 1 | 3.31 | 332.2 |
| 894 | A20-M-B32 | 1 | 4.07 | 374.3 |
| 895 | A20-M-B33 | 1 | 2.59 | 450.3 |
| 896 | A20-M-B35 | 1 | 3.24 | 318.2 |
| 897 | A20-M-B36 | 1 | 3.93 | 394.2 |
| 898 | A20-M-B39 | 1 | 2.4 | 395.2 |
| 899 | A20-M-B40 | 1 | 3.67 | 384.2 |
| 900 | A20-M-B42 | 1 | 3.39 | 376.2 |
| 901 | A20-M-B56 | 1 | 2.42 | 387.3 |
| 902 | A20-M-B59 | 1 | 2.44 | 401.3 |
| 903 | A33-M-B14 | 4 | 1.172 | 366.1 |
| 904 | A33-M-B22 | 4 | 1.33 | 372.2 |
| 905 | A33-M-B28 | 4 | 0.929 | 360.1 |
| 906 | A33-M-B29 | 4 | 0.645 | 367.1 |
| 907 | A33-M-B30 | 4 | 1.205 | 384.1 |
| 908 | A124-M-B9 | 4 | 0.655 | 341.2 |
| 909 | A125-M-B9 | 4 | 0.74 | 355.2 |
| 910 | A126-M-B9 | 4 | 1.018 | 356.2 |
| 911 | A127-M-B14 | 4 | 1.29 | 378.2 |
| 912 | A127-M-B19 | 1 | 3.06 | 328.2 |
| 913 | A127-M-B22 | 4 | 1.405 | 384.2 |
| 914 | A127-M-B24 | 1 | 3.79 | 370.3 |
| 915 | A127-M-B25 | 1 | 3.28 | 330.3 |
| 916 | A127-M-B26 | 1 | 3.56 | 356.3 |
| 917 | A127-M-B28 | 4 | 1 | 372.2 |
| 918 | A127-M-B29 | 4 | 0.757 | 379.1 |
| 919 | A127-M-B30 | 4 | 1.279 | 396.1 |
| 920 | A127-M-B31 | 1 | 2.95 | 316.2 |
| 921 | A127-M-B32 | 1 | 3.8 | 358.3 |
| 922 | A127-M-B33 | 1 | 2.28 | 434.3 |
| 923 | A127-M-B36 | 1 | 3.63 | 378.3 |
| 924 | A127-M-B37 | 1 | 3.83 | 378.3 |
| 925 | A127-M-B38 | 1 | 2.1 | 401.3 |
| 926 | A127-M-B39 | 1 | 2.06 | 379.2 |
| 927 | A127-M-B40 | 1 | 3.35 | 368.2 |
| 928 | A127-M-B41 | 1 | 2.68 | 399.3 |
| 929 | A127-M-B42 | 1 | 3.04 | 360.3 |
| 930 | A127-M-B43 | 1 | 3.59 | 344.3 |
| 931 | A127-M-B46 | 1 | 3.38 | 344.3 |
| 932 | A127-M-B47 | 1 | 3.6 | 382.2 |
| 933 | A127-M-B48 | 1 | 3.36 | 342.3 |
| 934 | A127-M-B49 | 1 | 2.26 | 397.3 |
| 935 | A127-M-B50 | 1 | 3.12 | 342.3 |
| 936 | A127-M-B51 | 1 | 2.9 | 358.2 |
| 937 | A127-M-B52 | 1 | 3.62 | 364.2 |
| 938 | A127-M-B53 | 1 | 2.12 | 413.3 |
| 939 | A127-M-B54 | 1 | 3.04 | 410.3 |
| 940 | A127-M-B56 | 1 | 2.08 | 371.3 |
| 941 | A127-M-B57 | 1 | 1.74 | 454.4 |
| 942 | A127-M-B58 | 1 | 2.79 | 435.2 |
| 943 | A127-M-B60 | 1 | 2.09 | 359.3 |
| 944 | A127-M-B7 | 1 | 2.96 | 346.2 |
| 945 | A127-M-B9 | 4 | 1.311 | 358.2 |
| 946 | A128-M-B14 | 4 | 1.23 | 378.2 |
| 947 | A128-M-B14 | 1 | 3.56 | 378.3 |
| 948 | A128-M-B17 | 1 | 2.98 | 316.2 |
| 949 | A128-M-B19 | 1 | 2.98 | 328.2 |
| 950 | A128-M-B22 | 4 | 1.401 | 384.2 |
| 951 | A128-M-B25 | 1 | 3.24 | 330.3 |
| 952 | A128-M-B26 | 1 | 3.5 | 356.3 |
| 953 | A128-M-B28 | 4 | 0.952 | 372.2 |
| 954 | A128-M-B29 | 4 | 0.73 | 379.1 |
| 955 | A128-M-B30 | 4 | 1.268 | 396.1 |
| 956 | A128-M-B31 | 1 | 2.9 | 316.2 |
| 957 | A128-M-B32 | 1 | 3.76 | 358.3 |
| 958 | A128-M-B33 | 1 | 2.26 | 434.3 |
| 959 | A128-M-B34 | 1 | 3.23 | 374.2 |
| 960 | A128-M-B35 | 1 | 2.79 | 302.2 |
| 961 | A128-M-B36 | 1 | 3.56 | 378.3 |
| 962 | A128-M-B37 | 1 | 3.77 | 378.3 |
| 963 | A128-M-B38 | 1 | 2.08 | 401.3 |
| 964 | A128-M-B39 | 1 | 2.03 | 379.2 |
| 965 | A128-M-B40 | 1 | 3.29 | 368.2 |
| 966 | A128-M-B41 | 1 | 2.64 | 399.3 |
| 967 | A128-M-B42 | 1 | 2.98 | 360.3 |
| 968 | A128-M-B43 | 1 | 3.54 | 344.3 |
| 969 | A128-M-B45 | 1 | 3.52 | 370.3 |
| 970 | A128-M-B46 | 1 | 3.35 | 344.3 |
| 971 | A128-M-B47 | 1 | 3.51 | 382.2 |
| 972 | A128-M-B48 | 1 | 3.31 | 342.3 |
| 973 | A128-M-B49 | 1 | 2.21 | 397.3 |
| 974 | A128-M-B50 | 1 | 3.08 | 342.3 |
| 975 | A128-M-B51 | 1 | 2.86 | 358.2 |
| 976 | A128-M-B54 | 1 | 3 | 410.3 |
| 977 | A128-M-B55 | 1 | 3.06 | 438.3 |
| 978 | A128-M-B56 | 1 | 2.1 | 371.3 |
| 979 | A128-M-B57 | 1 | 1.75 | 454.4 |
| 980 | A128-M-B58 | 1 | 2.76 | 435.2 |
| 981 | A128-M-B59 | 1 | 2.1 | 385.3 |
| 982 | A128-M-B60 | 1 | 2.08 | 359.3 |
| 983 | A128-M-B7 | 1 | 2.89 | 346.2 |
| 984 | A128-M-B9 | 4 | 1.304 | 358.2 |
| 985 | A129-M-B14 | 4 | 1.242 | 378.2 |
| 986 | A129-M-B22 | 4 | 1.399 | 384.2 |
| 987 | A129-M-B28 | 4 | 0.96 | 372.2 |

| Entry | Compound | HPLC Method | HPLC Rt (min) | [M + H]+ | Entry | Compound | HPLC Method | HPLC Rt (min) | [M + H]+ |
|---|---|---|---|---|---|---|---|---|---|
| 988 | A129-M-B29 | 4 | 0.752 | 379.1 | 1064 | A139-M-B42 | 1 | 3.21 | 378.3 |
| 989 | A129-M-B30 | 4 | 1.31 | 396.1 | 1065 | A139-M-B43 | 1 | 3.71 | 362.3 |
| 990 | A129-M-B9 | 4 | 1.303 | 358.2 | 1066 | A139-M-B45 | 1 | 3.71 | 388.3 |
| 991 | A130-M-B9 | 4 | 0.984 | 366.2 | 1067 | A139-M-B46 | 1 | 3.53 | 362.3 |
| 992 | A131-M-B9 | 4 | 1.164 | 382.2 | 1068 | A139-M-B48 | 1 | 3.51 | 360.2 |
| 993 | A132-M-B14 | 4 | 1.16 | 404.2 | 1069 | A139-M-B49 | 1 | 2.38 | 415.3 |
| 994 | A132-M-B22 | 4 | 1.309 | 410.2 | 1070 | A139-M-B50 | 1 | 3.29 | 360.2 |
| 995 | A132-M-B28 | 4 | 0.878 | 398.2 | 1071 | A139-M-B51 | 1 | 3.08 | 376.2 |
| 996 | A132-M-B29 | 4 | 0.693 | 405.1 | 1072 | A139-M-B52 | 1 | 3.77 | 382.2 |
| 997 | A132-M-B30 | 4 | 1.24 | 422.1 | 1073 | A139-M-B53 | 1 | 2.3 | 431.3 |
| 998 | A132-M-B9 | 4 | 1.219 | 384.2 | 1074 | A139-M-B56 | 1 | 2.28 | 389.3 |
| 999 | A133-M-B14 | 4 | 1.406 | 428.2 | 1075 | A139-M-B57 | 1 | 1.89 | 472.3 |
| 1000 | A133-M-B22 | 4 | 1.6 | 434.2 | 1076 | A139-M-B58 | 1 | 2.96 | 453.2 |
| 1001 | A133-M-B28 | 4 | 1.158 | 422.2 | 1077 | A139-M-B60 | 1 | 2.24 | 377.3 |
| 1002 | A133-M-B29 | 4 | 0.95 | 429.1 | 1078 | A139-M-B7 | 1 | 3.13 | 364.2 |
| 1003 | A133-M-B30 | 4 | 1.427 | 446.1 | 1079 | A140-M-B14 | 4 | 1.36 | 406.2 |
| 1004 | A133-M-B9 | 4 | 1.473 | 408.2 | 1080 | A140-M-B22 | 4 | 1.474 | 412.2 |
| 1005 | A134-M-B14 | 4 | 1.45 | 444.1 | 1081 | A140-M-B28 | 4 | 1.06 | 400.2 |
| 1006 | A134-M-B22 | 4 | 1.593 | 450.2 | 1082 | A140-M-B29 | 4 | 0.846 | 407.1 |
| 1007 | A134-M-B28 | 4 | 1.206 | 438.2 | 1083 | A140-M-B30 | 4 | 1.352 | 424.1 |
| 1008 | A134-M-B29 | 4 | 1.002 | 445.1 | 1084 | A141-M-B14 | 4 | 1.176 | 418.2 |
| 1009 | A134-M-B30 | 4 | 1.471 | 462.1 | 1085 | A141-M-B22 | 4 | 1.321 | 424.2 |
| 1010 | A134-M-B9 | 4 | 1.516 | 424.2 | 1086 | A141-M-B28 | 4 | 0.932 | 412.2 |
| 1011 | A135-M-B9 | 4 | 1.526 | 424.2 | 1087 | A141-M-B29 | 4 | 0.745 | 419.2 |
| 1012 | A136-M-B9 | 4 | 0.674 | 355.2 | 1088 | A141-M-B30 | 4 | 1.206 | 436.2 |
| 1013 | A137-M-B14 | 4 | 1.314 | 374.2 | 1089 | A142-M-B14 | 4 | 1.197 | 418.2 |
| 1014 | A137-M-B14 | 1 | 3.76 | 374.3 | 1090 | A142-M-B22 | 4 | 1.345 | 424.2 |
| 1015 | A137-M-B22 | 4 | 1.477 | 380.2 | 1091 | A142-M-B28 | 4 | 0.933 | 412.2 |
| 1016 | A137-M-B24 | 1 | 3.93 | 366.3 | 1092 | A142-M-B29 | 4 | 0.756 | 419.2 |
| 1017 | A137-M-B25 | 1 | 3.45 | 326.3 | 1093 | A142-M-B30 | 4 | 1.225 | 436.2 |
| 1018 | A137-M-B26 | 1 | 3.7 | 352.3 | 1094 | A143-M-B14 | 4 | 1.45 | 428.2 |
| 1019 | A137-M-B28 | 4 | 1.08 | 368.2 | 1095 | A143-M-B22 | 4 | 1.562 | 434.2 |
| 1020 | A137-M-B29 | 4 | 0.808 | 375.2 | 1096 | A143-M-B28 | 4 | 1.178 | 422.2 |
| 1021 | A137-M-B30 | 4 | 1.346 | 392.2 | 1097 | A143-M-B29 | 4 | 0.977 | 429.1 |
| 1022 | A137-M-B32 | 1 | 3.95 | 354.3 | 1098 | A143-M-B30 | 4 | 1.443 | 446.1 |
| 1023 | A137-M-B33 | 1 | 2.4 | 430.3 | 1099 | A144-M-B14 | 4 | 0.649 | 350.2 |
| 1024 | A137-M-B34 | 1 | 3.42 | 370.3 | 1100 | A144-M-B22 | 4 | 0.83 | 356.2 |
| 1025 | A137-M-B35 | 1 | 3.01 | 298.2 | 1101 | A144-M-B30 | 4 | 0.686 | 368.1 |
| 1026 | A137-M-B36 | 1 | 3.77 | 374.3 | 1102 | A145-M-B14 | 4 | 1.52 | 477.1 |
| 1027 | A137-M-B39 | 1 | 2.19 | 375.3 | 1103 | A145-M-B22 | 4 | 1.594 | 483.1 |
| 1028 | A137-M-B40 | 1 | 3.49 | 364.3 | 1104 | A146-M-B14 | 1 | 3.6 | 408.3 |
| 1029 | A137-M-B43 | 1 | 3.73 | 340.3 | 1105 | A146-M-B17 | 1 | 3.06 | 346.2 |
| 1030 | A137-M-B48 | 1 | 3.5 | 338.3 | 1106 | A146-M-B19 | 1 | 3.07 | 358.2 |
| 1031 | A137-M-B49 | 1 | 2.4 | 393.3 | 1107 | A146-M-B24 | 1 | 3.77 | 400.3 |
| 1032 | A137-M-B50 | 1 | 3.27 | 338.3 | 1108 | A146-M-B25 | 1 | 3.29 | 360.3 |
| 1033 | A137-M-B52 | 1 | 3.76 | 360.3 | 1109 | A146-M-B26 | 1 | 3.55 | 386.3 |
| 1034 | A137-M-B54 | 1 | 3.19 | 406.3 | 1110 | A146-M-B31 | 1 | 2.97 | 346.2 |
| 1035 | A137-M-B55 | 1 | 3.24 | 434.3 | 1111 | A146-M-B32 | 1 | 3.77 | 388.3 |
| 1036 | A137-M-B56 | 1 | 2.25 | 367.3 | 1112 | A146-M-B33 | 1 | 2.32 | 464.3 |
| 1037 | A137-M-B58 | 1 | 2.93 | 431.3 | 1113 | A146-M-B34 | 1 | 3.27 | 404.2 |
| 1038 | A137-M-B59 | 1 | 2.25 | 381.3 | 1114 | A146-M-B35 | 1 | 2.88 | 332.2 |
| 1039 | A138-M-B14 | 4 | 1.206 | 390.2 | 1115 | A146-M-B36 | 1 | 3.64 | 408.3 |
| 1040 | A138-M-B22 | 4 | 1.43 | 396.2 | 1116 | A146-M-B37 | 1 | 3.83 | 408.3 |
| 1041 | A138-M-B28 | 4 | 0.926 | 384.2 | 1117 | A146-M-B38 | 1 | 2.24 | 431.3 |
| 1042 | A138-M-B29 | 4 | 0.726 | 391.2 | 1118 | A146-M-B39 | 1 | 2.17 | 409.3 |
| 1043 | A138-M-B30 | 4 | 1.23 | 408.2 | 1119 | A146-M-B40 | 1 | 3.34 | 398.2 |
| 1044 | A139-M-B14 | 1 | 3.75 | 396.2 | 1120 | A146-M-B41 | 1 | 2.73 | 429.3 |
| 1045 | A139-M-B17 | 1 | 3.22 | 334.2 | 1121 | A146-M-B42 | 1 | 3.05 | 390.3 |
| 1046 | A139-M-B19 | 1 | 3.23 | 346.2 | 1122 | A146-M-B43 | 1 | 3.57 | 374.3 |
| 1047 | A139-M-B22 | 4 | 1.441 | 402.2 | 1123 | A146-M-B44 | 1 | 2.28 | 415.3 |
| 1048 | A139-M-B24 | 1 | 3.93 | 388.3 | 1124 | A146-M-B45 | 1 | 3.56 | 400.3 |
| 1049 | A139-M-B25 | 1 | 3.46 | 348.2 | 1125 | A146-M-B46 | 1 | 3.38 | 374.3 |
| 1050 | A139-M-B26 | 1 | 3.71 | 374.3 | 1126 | A146-M-B47 | 1 | 3.58 | 412.3 |
| 1051 | A139-M-B28 | 4 | 1.023 | 390.2 | 1127 | A146-M-B48 | 1 | 3.34 | 372.3 |
| 1052 | A139-M-B29 | 4 | 0.822 | 397.1 | 1128 | A146-M-B49 | 1 | 2.33 | 427.3 |
| 1053 | A139-M-B30 | 4 | 1.32 | 414.1 | 1129 | A146-M-B50 | 1 | 3.13 | 372.3 |
| 1054 | A139-M-B31 | 1 | 3.12 | 334.2 | 1130 | A146-M-B51 | 1 | 2.92 | 388.3 |
| 1055 | A139-M-B32 | 1 | 3.91 | 376.3 | 1131 | A146-M-B52 | 1 | 3.63 | 394.2 |
| 1056 | A139-M-B33 | 1 | 2.45 | 452.3 | 1132 | A146-M-B53 | 1 | 2.19 | 443.3 |
| 1057 | A139-M-B35 | 1 | 3.03 | 320.2 | 1133 | A146-M-B54 | 1 | 3.04 | 440.3 |
| 1058 | A139-M-B36 | 1 | 3.77 | 396.2 | 1134 | A146-M-B55 | 1 | 3.11 | 468.3 |
| 1059 | A139-M-B37 | 1 | 3.95 | 396.2 | 1135 | A146-M-B58 | 1 | 2.84 | 465.3 |
| 1060 | A139-M-B38 | 1 | 2.29 | 419.3 | 1136 | A146-M-B7 | 1 | 2.97 | 376.3 |
| 1061 | A139-M-B39 | 1 | 2.23 | 397.2 | 1137 | A147-M-B14 | 1 | 3.76 | 374.3 |
| 1062 | A139-M-B40 | 1 | 3.51 | 386.2 | 1138 | A147-M-B17 | 1 | 3.2 | 312.3 |
| 1063 | A139-M-B41 | 1 | 2.87 | 417.3 | 1139 | A147-M-B24 | 1 | 3.93 | 366.3 |

-continued

| Entry | Compound | HPLC Method | HPLC Rt (min) | [M + H]+ |
|---|---|---|---|---|
| 1140 | A147-M-B25 | 1 | 3.46 | 326.3 |
| 1141 | A147-M-B26 | 1 | 3.71 | 352.3 |
| 1142 | A147-M-B31 | 1 | 3.12 | 312.3 |
| 1143 | A147-M-B32 | 1 | 3.95 | 354.3 |
| 1144 | A147-M-B33 | 1 | 2.42 | 430.3 |
| 1145 | A147-M-B34 | 1 | 3.43 | 370.3 |
| 1146 | A147-M-B36 | 1 | 3.76 | 374.3 |
| 1147 | A147-M-B37 | 1 | 3.96 | 374.3 |
| 1148 | A147-M-B39 | 1 | 2.24 | 375.3 |
| 1149 | A147-M-B40 | 1 | 3.5 | 364.3 |
| 1150 | A147-M-B41 | 1 | 2.86 | 395.3 |
| 1151 | A147-M-B42 | 1 | 3.19 | 356.3 |
| 1152 | A147-M-B43 | 1 | 3.75 | 340.3 |
| 1153 | A147-M-B45 | 1 | 3.73 | 366.3 |
| 1154 | A147-M-B46 | 1 | 3.55 | 340.3 |
| 1155 | A147-M-B47 | 1 | 3.74 | 378.3 |
| 1156 | A147-M-B48 | 1 | 3.52 | 338.3 |
| 1157 | A147-M-B50 | 1 | 3.29 | 338.3 |
| 1158 | A147-M-B51 | 1 | 3.08 | 354.3 |
| 1159 | A147-M-B52 | 1 | 3.76 | 360.3 |
| 1160 | A147-M-B54 | 1 | 3.19 | 406.3 |
| 1161 | A147-M-B58 | 1 | 2.95 | 431.3 |
| 1162 | A147-M-B7 | 1 | 3.12 | 342.3 |
| 1163 | A148-M-B14 | 1 | 3.57 | 408.3 |
| 1164 | A148-M-B17 | 1 | 3.01 | 346.2 |
| 1165 | A148-M-B19 | 1 | 3.03 | 358.2 |
| 1166 | A148-M-B24 | 1 | 3.72 | 400.3 |
| 1167 | A148-M-B25 | 1 | 3.24 | 360.3 |
| 1168 | A148-M-B26 | 1 | 3.51 | 386.3 |
| 1169 | A148-M-B31 | 1 | 2.93 | 346.2 |
| 1170 | A148-M-B32 | 1 | 3.74 | 388.3 |
| 1171 | A148-M-B33 | 1 | 2.3 | 464.3 |
| 1172 | A148-M-B34 | 1 | 3.23 | 404.2 |
| 1173 | A148-M-B35 | 1 | 2.85 | 332.2 |
| 1174 | A148-M-B36 | 1 | 3.59 | 408.3 |
| 1175 | A148-M-B37 | 1 | 3.78 | 408.3 |
| 1176 | A148-M-B39 | 1 | 2.13 | 409.3 |
| 1177 | A148-M-B40 | 1 | 3.3 | 398.2 |
| 1178 | A148-M-B41 | 1 | 2.69 | 429.3 |
| 1179 | A148-M-B42 | 1 | 3.02 | 390.3 |
| 1180 | A148-M-B43 | 1 | 3.52 | 374.3 |
| 1181 | A148-M-B45 | 1 | 3.52 | 400.3 |
| 1182 | A148-M-B46 | 1 | 3.35 | 374.3 |
| 1183 | A148-M-B47 | 1 | 3.54 | 412.3 |
| 1184 | A148-M-B48 | 1 | 3.31 | 372.3 |
| 1185 | A148-M-B50 | 1 | 3.11 | 372.3 |
| 1186 | A148-M-B51 | 1 | 2.9 | 388.3 |
| 1187 | A148-M-B52 | 1 | 3.59 | 394.2 |
| 1188 | A148-M-B53 | 1 | 2.17 | 443.3 |
| 1189 | A148-M-B54 | 1 | 3.01 | 440.3 |
| 1190 | A148-M-B55 | 1 | 3.07 | 468.3 |
| 1191 | A148-M-B56 | 1 | 2.2 | 401.3 |
| 1192 | A148-M-B58 | 1 | 2.8 | 465.3 |
| 1193 | A148-M-B7 | 1 | 2.94 | 376.3 |
| 1194 | A149-M-B14 | 1 | 3.83 | 396.2 |
| 1195 | A149-M-B17 | 1 | 3.3 | 334.2 |
| 1196 | A149-M-B19 | 1 | 3.3 | 346.2 |
| 1197 | A149-M-B24 | 1 | 3.99 | 388.3 |
| 1198 | A149-M-B25 | 1 | 3.53 | 348.2 |
| 1199 | A149-M-B26 | 1 | 3.79 | 374.3 |
| 1200 | A149-M-B31 | 1 | 3.2 | 334.2 |
| 1201 | A149-M-B33 | 1 | 2.49 | 452.3 |
| 1202 | A149-M-B34 | 1 | 3.49 | 392.2 |
| 1203 | A149-M-B35 | 1 | 3.09 | 320.2 |
| 1204 | A149-M-B36 | 1 | 3.73 | 396.2 |
| 1205 | A149-M-B38 | 1 | 2.32 | 419.3 |
| 1206 | A149-M-B39 | 1 | 2.29 | 397.2 |
| 1207 | A149-M-B40 | 1 | 3.58 | 386.2 |
| 1208 | A149-M-B41 | 1 | 2.93 | 417.3 |
| 1209 | A149-M-B42 | 1 | 3.29 | 378.3 |
| 1210 | A149-M-B43 | 1 | 3.81 | 362.3 |
| 1211 | A149-M-B44 | 1 | 2.37 | 403.3 |
| 1212 | A149-M-B45 | 1 | 3.78 | 388.3 |
| 1213 | A149-M-B46 | 1 | 3.58 | 362.3 |
| 1214 | A149-M-B47 | 1 | 3.81 | 400.2 |
| 1215 | A149-M-B48 | 1 | 3.59 | 360.2 |
| 1216 | A149-M-B49 | 1 | 2.44 | 415.3 |
| 1217 | A149-M-B50 | 1 | 3.36 | 360.2 |
| 1218 | A149-M-B51 | 1 | 3.15 | 376.2 |
| 1219 | A149-M-B52 | 1 | 3.83 | 382.2 |
| 1220 | A149-M-B53 | 1 | 2.29 | 431.3 |
| 1221 | A149-M-B54 | 1 | 3.26 | 428.3 |
| 1222 | A149-M-B55 | 1 | 3.34 | 456.3 |
| 1223 | A149-M-B56 | 1 | 2.32 | 389.3 |
| 1224 | A149-M-B57 | 1 | 1.92 | 472.3 |
| 1225 | A149-M-B58 | 1 | 3.02 | 453.2 |
| 1226 | A149-M-B60 | 1 | 2.27 | 377.3 |
| 1227 | A150-M-B14 | 1 | 3.88 | 394.2 |
| 1228 | A150-M-B17 | 1 | 3.38 | 332.2 |
| 1229 | A150-M-B19 | 1 | 3.38 | 344.2 |
| 1230 | A150-M-B24 | 1 | 4.05 | 386.3 |
| 1231 | A150-M-B25 | 1 | 3.6 | 346.2 |
| 1232 | A150-M-B26 | 1 | 3.83 | 372.2 |
| 1233 | A150-M-B31 | 1 | 3.29 | 332.2 |
| 1234 | A150-M-B32 | 1 | 4.04 | 374.3 |
| 1235 | A150-M-B33 | 1 | 2.59 | 450.3 |
| 1236 | A150-M-B35 | 1 | 3.2 | 318.2 |
| 1237 | A150-M-B36 | 1 | 3.89 | 394.2 |
| 1238 | A150-M-B37 | 1 | 4.06 | 394.2 |
| 1239 | A150-M-B38 | 1 | 2.39 | 417.3 |
| 1240 | A150-M-B39 | 1 | 2.35 | 395.2 |
| 1241 | A150-M-B40 | 1 | 3.65 | 384.2 |
| 1242 | A150-M-B41 | 1 | 3.04 | 415.2 |
| 1243 | A150-M-B42 | 1 | 3.35 | 376.2 |
| 1244 | A150-M-B43 | 1 | 3.86 | 360.2 |
| 1245 | A150-M-B45 | 1 | 3.85 | 386.3 |
| 1246 | A150-M-B46 | 1 | 3.68 | 360.2 |
| 1247 | A150-M-B48 | 1 | 3.65 | 358.2 |
| 1248 | A150-M-B49 | 1 | 2.51 | 413.3 |
| 1249 | A150-M-B50 | 1 | 3.43 | 358.2 |
| 1250 | A150-M-B51 | 1 | 3.23 | 374.2 |
| 1251 | A150-M-B52 | 1 | 3.89 | 380.2 |
| 1252 | A150-M-B53 | 1 | 2.38 | 429.3 |
| 1253 | A150-M-B54 | 1 | 3.34 | 426.3 |
| 1254 | A150-M-B55 | 1 | 3.39 | 454.3 |
| 1255 | A150-M-B56 | 1 | 2.44 | 387.3 |
| 1256 | A150-M-B57 | 1 | 1.98 | 470.3 |
| 1257 | A150-M-B58 | 1 | 3.11 | 451.2 |
| 1258 | A150-M-B59 | 1 | 2.41 | 401.3 |
| 1259 | A150-M-B7 | 1 | 3.28 | 362.2 |
| 1260 | A151-M-B14 | 1 | 3.72 | 396.2 |
| 1261 | A151-M-B17 | 1 | 3.18 | 334.2 |
| 1262 | A151-M-B19 | 1 | 3.18 | 346.2 |
| 1263 | A151-M-B24 | 1 | 3.89 | 388.3 |
| 1264 | A151-M-B25 | 1 | 3.42 | 348.2 |
| 1265 | A151-M-B26 | 1 | 3.68 | 374.3 |
| 1266 | A151-M-B31 | 1 | 3.09 | 334.2 |
| 1267 | A151-M-B32 | 1 | 3.9 | 376.3 |
| 1268 | A151-M-B33 | 1 | 2.41 | 452.3 |
| 1269 | A151-M-B35 | 1 | 2.99 | 320.2 |
| 1270 | A151-M-B36 | 1 | 3.84 | 396.2 |
| 1271 | A151-M-B37 | 1 | 3.91 | 396.2 |
| 1272 | A151-M-B38 | 1 | 2.23 | 419.3 |
| 1273 | A151-M-B39 | 1 | 2.2 | 397.2 |
| 1274 | A151-M-B41 | 1 | 2.83 | 417.3 |
| 1275 | A151-M-B42 | 1 | 3.17 | 378.3 |
| 1276 | A151-M-B43 | 1 | 3.72 | 362.3 |
| 1277 | A151-M-B45 | 1 | 3.69 | 388.3 |
| 1278 | A151-M-B46 | 1 | 3.51 | 362.3 |
| 1279 | A151-M-B48 | 1 | 3.48 | 360.2 |
| 1280 | A151-M-B49 | 1 | 2.34 | 415.3 |
| 1281 | A151-M-B50 | 1 | 3.25 | 360.2 |
| 1282 | A151-M-B51 | 1 | 3.05 | 376.2 |
| 1283 | A151-M-B52 | 1 | 3.74 | 382.2 |
| 1284 | A151-M-B53 | 1 | 2.23 | 431.3 |
| 1285 | A151-M-B54 | 1 | 3.16 | 428.3 |
| 1286 | A151-M-B56 | 1 | 2.24 | 389.3 |
| 1287 | A151-M-B57 | 1 | 1.86 | 472.3 |
| 1288 | A151-M-B58 | 1 | 2.93 | 453.2 |
| 1289 | A151-M-B59 | 1 | 2.24 | 403.3 |
| 1290 | A151-M-B60 | 1 | 2.21 | 377.3 |
| 1291 | A151-M-B7 | 1 | 3.07 | 364.2 |

-continued

| Entry | Compound | HPLC Method | HPLC Rt (min) | [M + H]+ |
|---|---|---|---|---|
| 1292 | A152-M-B14 | 1 | 3.95 | 352.3 |
| 1293 | A152-M-B17 | 1 | 3.42 | 290.3 |
| 1294 | A152-M-B19 | 1 | 3.43 | 302.3 |
| 1295 | A152-M-B24 | 1 | 4.12 | 344.3 |
| 1296 | A152-M-B25 | 1 | 3.66 | 304.3 |
| 1297 | A152-M-B26 | 1 | 3.92 | 330.3 |
| 1298 | A152-M-B31 | 1 | 3.32 | 290.3 |
| 1299 | A152-M-B32 | 1 | 4.13 | 332.3 |
| 1300 | A152-M-B33 | 1 | 2.69 | 408.3 |
| 1301 | A152-M-B34 | 1 | 3.63 | 348.3 |
| 1302 | A152-M-B35 | 1 | 3.23 | 276.3 |
| 1303 | A152-M-B36 | 1 | 3.95 | 352.3 |
| 1304 | A152-M-B37 | 1 | 4.15 | 352.3 |
| 1305 | A152-M-B38 | 1 | 2.42 | 375.3 |
| 1306 | A152-M-B39 | 1 | 2.49 | 353.3 |
| 1307 | A152-M-B40 | 1 | 3.69 | 342.3 |
| 1308 | A152-M-B41 | 1 | 3.04 | 373.3 |
| 1309 | A152-M-B42 | 1 | 3.4 | 334.3 |
| 1310 | A152-M-B43 | 1 | 3.95 | 318.3 |
| 1311 | A152-M-B45 | 1 | 3.91 | 344.3 |
| 1312 | A152-M-B46 | 1 | 3.74 | 318.3 |
| 1313 | A152-M-B47 | 1 | 3.9 | 356.3 |
| 1314 | A152-M-B48 | 1 | 3.72 | 316.3 |
| 1315 | A152-M-B49 | 1 | 2.52 | 371.3 |
| 1316 | A152-M-B50 | 1 | 3.49 | 316.3 |
| 1317 | A152-M-B51 | 1 | 3.28 | 332.3 |
| 1318 | A152-M-B52 | 1 | 3.96 | 338.3 |
| 1319 | A152-M-B53 | 1 | 2.46 | 387.4 |
| 1320 | A152-M-B54 | 1 | 3.38 | 384.3 |
| 1321 | A152-M-B55 | 1 | 3.44 | 412.4 |
| 1322 | A152-M-B56 | 1 | 2.42 | 345.3 |
| 1323 | A152-M-B57 | 1 | 1.99 | 428.4 |
| 1324 | A152-M-B58 | 1 | 3.14 | 409.3 |
| 1325 | A152-M-B7 | 1 | 3.33 | 320.3 |
| 1326 | A153-M-B48 | 1 | 3.64 | 350.3 |
| 1327 | A154-M-B14 | 1 | 3.34 | 324.3 |
| 1328 | A154-M-B17 | 1 | 2.58 | 262.2 |
| 1329 | A154-M-B19 | 1 | 2.6 | 274.2 |
| 1330 | A154-M-B24 | 1 | 3.54 | 316.3 |
| 1331 | A154-M-B25 | 1 | 2.9 | 276.3 |
| 1332 | A154-M-B26 | 1 | 3.25 | 302.3 |
| 1333 | A154-M-B31 | 1 | 2.46 | 262.2 |
| 1334 | A154-M-B32 | 1 | 3.53 | 304.3 |
| 1335 | A154-M-B33 | 1 | 2 | 380.3 |
| 1336 | A154-M-B34 | 1 | 2.88 | 320.2 |
| 1337 | A154-M-B35 | 1 | 2.32 | 248.2 |
| 1338 | A154-M-B36 | 1 | 3.29 | 324.3 |
| 1339 | A154-M-B42 | 1 | 2.63 | 306.3 |
| 1340 | A154-M-B43 | 1 | 3.29 | 290.3 |
| 1341 | A154-M-B45 | 1 | 3.27 | 316.3 |
| 1342 | A154-M-B47 | 1 | 3.25 | 328.3 |
| 1343 | A154-M-B48 | 1 | 2.99 | 288.3 |
| 1344 | A154-M-B49 | 1 | 1.85 | 343.3 |
| 1345 | A154-M-B51 | 1 | 2.45 | 304.3 |
| 1346 | A154-M-B52 | 1 | 3.32 | 310.2 |
| 1347 | A154-M-B53 | 1 | 1.83 | 359.3 |
| 1348 | A154-M-B54 | 1 | 2.65 | 355.2 |
| 1349 | A154-M-B55 | 1 | 2.73 | 384.3 |
| 1350 | A154-M-B58 | 1 | 2.38 | 381.3 |
| 1351 | A154-M-B7 | 1 | 2.49 | 292.3 |
| 1352 | A155-M-B17 | 1 | 2.03 | 323.2 |
| 1353 | A155-M-B19 | 1 | 2.05 | 335.2 |
| 1354 | A155-M-B25 | 1 | 2.28 | 337.3 |
| 1355 | A155-M-B31 | 1 | 2 | 323.2 |
| 1356 | A155-M-B32 | 1 | 2.9 | 365.3 |
| 1357 | A155-M-B33 | 1 | 1.86 | 441.3 |
| 1358 | A155-M-B35 | 1 | 1.87 | 309.2 |
| 1359 | A155-M-B36 | 1 | 2.71 | 385.3 |
| 1360 | A155-M-B39 | 1 | 1.72 | 386.3 |
| 1361 | A155-M-B40 | 1 | 2.37 | 375.2 |
| 1362 | A155-M-B43 | 1 | 2.61 | 351.3 |
| 1363 | A155-M-B45 | 1 | 2.66 | 377.3 |
| 1364 | A155-M-B53 | 1 | 1.74 | 420.3 |
| 1365 | A155-M-B7 | 1 | 2.02 | 353.3 |
| 1366 | A156-M-B24 | 1 | 3.19 | 403.3 |
| 1367 | A156-M-B34 | 1 | 2.59 | 407.2 |
| 1368 | A156-M-B37 | 1 | 3.23 | 411.3 |
| 1369 | A156-M-B45 | 1 | 2.96 | 403.3 |
| 1370 | A156-M-B49 | 1 | 2.01 | 430.3 |
| 1371 | A156-M-B51 | 1 | 2.21 | 391.3 |
| 1372 | A156-M-B52 | 1 | 2.94 | 397.3 |
| 1373 | A156-M-B54 | 1 | 2.4 | 443.3. |

3. A method for inhibiting protein kinase activity in a mammal, which comprises contacting the kinase in said mammal with an effective amount of a compound of formula (I) as defined in claim 1, wherein the protein kinase is selected from the group consisting of PIM-1 and PIM-2.

4. A process for preparing a compound of formula (I) characterized in that the process comprises:

9d) reacting a compound of formula (I):

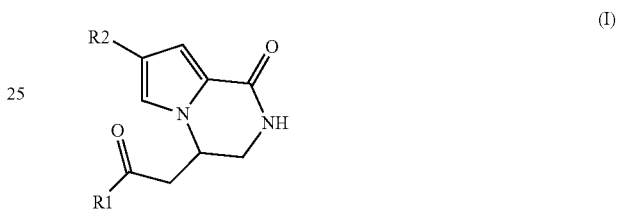

wherein R1 is —OR$^a$ and R$^a$ is $C_1$-$C_6$ alkyl, and R2 is NH$_2$ according to any one of the alternative steps:

d.1) with an acid or an acyl halide of formula (VI):

$R^c$COZ (VI)

wherein R$^c$ is hydrogen or a group selected from straight or branched $C_1$-$C_6$ alkyl, $C_2$-$C_6$ alkenyl or $C_2$-$C_6$ alkynyl, $C_3$-$C_6$ cycloalkyl, cycloalkyl $C_1$-$C_6$ alkyl, heterocyclyl, heterocyclyl $C_1$-$C_6$ alkyl, aryl, aryl $C_1$-$C_6$ alkyl, heteroaryl and heteroaryl $C_1$-$C_6$ alkyl, and wherein R$^c$ is optionally further substituted by halogen, nitro, oxo, cyano, $C_1$-$C_6$ alkyl, $C_3$-$C_6$ cycloalkyl, heterocyclyl, aryl, heteroaryl, dialkylamino or alkoxy and Z is a halogen or a group —OH, to give a compound of formula (I):

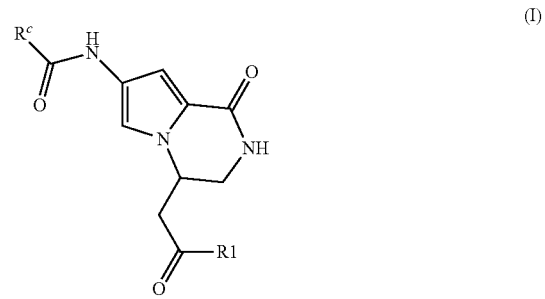

wherein R1 is —OR$^a$ and R$^a$ is $C_1$-$C_6$ alkyl and R$^c$ is as defined above; or d.2) with an isocyanate of formula (VII):

$R^c$NCO (VII)

wherein $R^c$ is as defined above, to give a compound of formula (I):

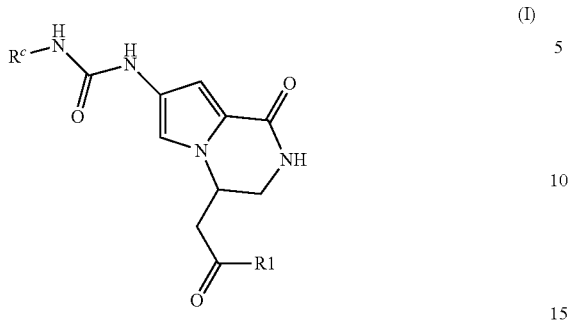

(I)

wherein R1 is —OR$^a$ and R$^a$ is $C_1$-$C_6$ alkyl and R$^c$ is as defined above; or d.3) with a sulphonyl halide of formula (VIII):

$R^cSO_2Z^1$ (VIII)

wherein R$^c$ is as defined above and Z' is a halogen, to give a compound of formula (I):

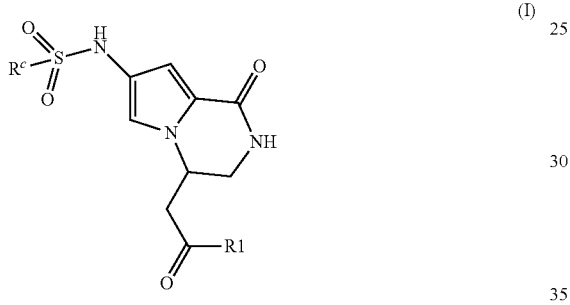

(I)

wherein R1 is —OR$^a$ and R$^a$ is $C_1$-$C_6$ alkyl and R$^c$ is as defined above; or h) reacting a compound of formula (XI):

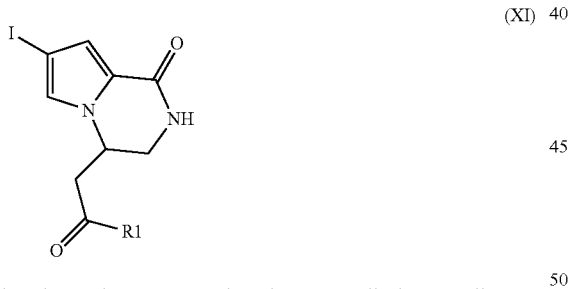

(XI)

wherein R1 is —OR$^a$ and R$^a$ is $C_1$-$C_6$ alkyl, according to any one of the alternative steps:

h.1) with a boronic acid or ester of formula (XII):

$R2'B(OZ'')(OZ''')$ (XII)

wherein R2' is R$^d$ and R$^d$ is hydrogen or a group selected from straight or branched $C_1$-$C_6$ alkyl, $C_2$-$C_6$ alkenyl or $C_2$-$C_6$ alkynyl, $C_3$-$C_6$ cycloalkyl, cycloalkyl $C_1$-$C_6$ alkyl, heterocyclyl, heterocyclyl $C_1$-$C_6$ alkyl, aryl, aryl $C_1$-$C_6$ alkyl, heteroaryl and heteroaryl $C_1$-$C_6$ alkyl, and wherein R$^d$ is optionally substituted by halogen, nitro, carboxy, cyano, $C_1$-$C_6$ alkyl, polyfluorinated alkyl, $C_3$-$C_6$ cycloalkyl, aryl, heteroaryl, amino, dialkylamino, hydroxy, alkoxy, polyfluorinated alkoxy, alkylcarbonyl, alkoxycarbonyl or alkylthio and Z'' and Z''' are either H, alkyl or, taken together with the oxygen atoms to which they are bonded, may form a 5 to 6 membered heterocycle, to give a compound of formula (I):

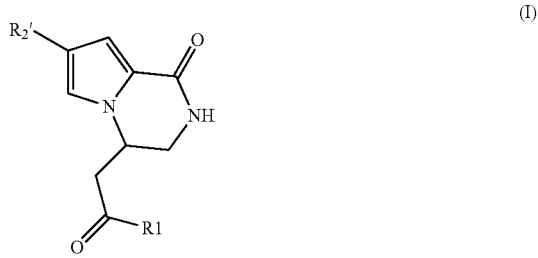

(I)

wherein R1 is —OR$^a$ and R$^a$ is $C_1$-$C_6$ alkyl and R2' is as defined above; or h.2) with a terminal alkyne of formula (XIII):

$R^dC{\equiv}CH$ (XIII)

wherein R$^d$ is as defined above, to give a compound of formula (I):

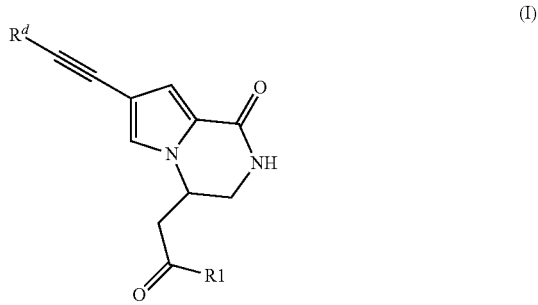

(I)

wherein R1 is —OR$^a$ and R$^a$ is $C_1$-$C_6$ alkyl and R$^d$ is as defined above.

5. A process according to claim 4, characterized in that the compound of formula (I) wherein R1 is —OR$^a$ and R$^a$ is $C_1$-$C_6$ alkyl, and R2 is NH$_2$, is prepared according to the following steps:

a) nitrating under acidic conditions the compound of formula (II):

(II)

b) reacting the resultant compound of formula (III):

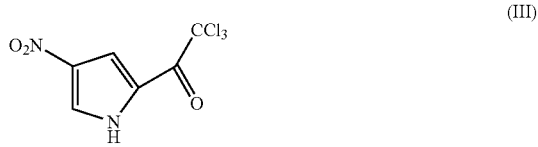

(III)

with an ammonium salt of formula (IV):

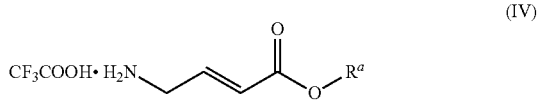

(IV)

wherein $R^a$ is $C_1$-$C_6$ alkyl to form a resultant compound of formula (V):
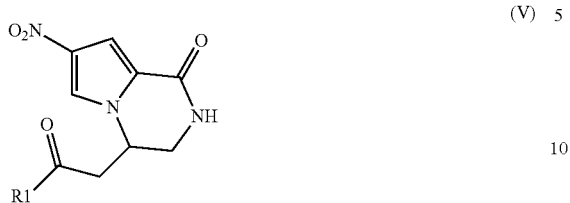
(V)
wherein R1 is —$OR^a$ and $R^a$ is $C_1$-$C_6$ alkyl,
c) reducing said compound of formula (V) to give a compound of formula (I):
(I)
wherein R2 is $NH_2$.
* * * * *